US007255862B1

(12) United States Patent
Tartaglia et al.

(10) Patent No.: US 7,255,862 B1
(45) Date of Patent: Aug. 14, 2007

(54) ALVAC/FIV CONSTRUCTS

(75) Inventors: James Tartaglia, Schenectady, NY (US); Enzo Paoletti, Delmar, NY (US)

(73) Assignee: Connaught Technology Corporation, Greenville, DE (US)

( * ) Notice: Subject to any disclaimer, the term of this patent is extended or adjusted under 35 U.S.C. 154(b) by 0 days.

(21) Appl. No.: 08/746,668

(22) Filed: Nov. 14, 1996

(51) Int. Cl.
 *A61K 39/21* (2006.01)
(52) U.S. Cl. ............................... 424/188.1; 424/208.1; 424/199.1; 424/232.1
(58) Field of Classification Search ................ 435/236, 435/237, 320.1; 424/199.1, 188.1, 208.1, 424/232.1
See application file for complete search history.

(56) References Cited

U.S. PATENT DOCUMENTS

| 5,275,813 | A | | 1/1994 | Yamamoto et al. | |
| 5,413,927 | A | | 5/1995 | Tompkins et al. | |
| 5,736,378 | A | * | 4/1998 | Elder et al. | 435/235.1 |
| 5,756,103 | A | * | 5/1998 | Paoletti et al. | 424/199.1 |
| 5,766,598 | A | * | 6/1998 | Paoletti et al. | 424/199.1 |
| 5,863,542 | A | * | 1/1999 | Paoletti et al. | 424/199.1 |

FOREIGN PATENT DOCUMENTS

WO           9530019           11/1995

OTHER PUBLICATIONS

Cox, W. I., et al., 1993, "Induction of Cytotoxic T Lymphocytes by Recombinant Canarypox (ALVAC) and Attenuated Vaccinia (NYVAC) Viruses Expressing the HIV-1 Envelope Glycoprotein", Virol. 195:845-850.*
Verschoor, E.J., et al., 1993, "Expression of Feline Immunodeficiency Virus gag and env Precursor Proteins in Spodoptera frugiperda Cells and Their Use in Immunodiagnosis", J. Clin. Microbiol. 31(9):2350-2355.*
Lutz, H., et al., 1995, "FIV Vaccine Studies. I. Immune response to recombinant FIV env gene products and outcome after challenge infection", Vet. Immunol. Immunopath. 46:103-113.*
Pialoux, G., et al., 1995, "A Prime-Boost Approach to HIV Preventative Vaccine Using a Recombinant Canarypox Virus Expressing Glycoprotein 160 (MN) followed by a Recombinant Glycoprotein 160 (MN/LAI)", AIDS Res. Human Retrovir. 11(3):373-381.*
Talbott, R. L., et al., 1989, "Nucleotide sequence and genomic organization of feline immunodeficiency virus", Proc. Natl. Acad. Sci. USA 86(15):5743-5747.*
Maki, N., et al., 1992, "Molecular characterization and heterogeneity of feline immunodeficiency virus isolates", Arch. Virol. 123(1-2):29-45.*
Miyazawa, T., et al., 1994, "The genome of feline immunodeficiency virus", Arch. Virol. 134(3-4):221-234.*
Tartaglia, J., et al., 1993, "Protection of Cats against Feline Leukemia Virus by Vaccination with a Canarypox Virus Recombinant, ALVAC-FL", J. Virol. 67(4):23702375.*

Abimiku, A., Franchini, G., Tartaglia, J. Aldrich, K., Myagkikh, M., Markham, P.D., Chong, P., Klein, M., Kieny, M.P., Paoletti, E., Gallo, R.C., and Guroff, M.R., Nature Medicine 1, 321-329 (1995).
Altenburger, W., C-P. Suter and J. Altenburger, Archives Virol. 105, 15-27 (1989).
Behbehani, A.M., Microbiological Reviews 47, 455-509 (1983).
Bergoin, M., and Dales, S., In Comparative Virology, eds. K. Maramorosch and E. Kurstak, (Academic Press, NY) pp. 169-205 (1971).
Berman, P., Gregory, T., Riddle, L., Nakamura, G., Champe, M., Porter, J., Wurm, F., Hershberg, R., Cobb, E. and Eichberg, J., Nature 345, 622-625 (1990).
Bocchia, M. et al., Blood 85, 2680-2684.
Buller, R.M.L., G.L. Smith, Cremer, K., Notkins, A.L., and Moss, B., Nature 317, 813-815 (1985).
Cadoz, M., A. Strady, B. Meignier, J. Taylor, J. Tartaglia, E. Paoletti and S. Plotkin, The Lancet, 339, 1429-1432 (1992).
Child, S.J., Palumbo, G.J., Buller, R.M.L., and Hruby, D.E. Virology 174, 625-629 (1990).
Clements, M.L., Weinhold, K., Siliciano, R., Schwartz, D., Matthews, T., Graham, B., Keefer, M., McElrath, J., Gorse, G., Hsieh, R., Duliege, A.M., Excler, J., Meignier, B., Tartaglia, J., and Paoletti, E., HIV immunity induced by carnarypox (ALVAC)-MN gl160, -SF-2, rgp120 or both. XI International Conference on AIDS/Vancover 1996/Mo.A.281 (1996).

(Continued)

*Primary Examiner*—Jeffrey S. Parkin
(74) *Attorney, Agent, or Firm*—Thomas J. Kowalski; Judy Jarecki-Black; Frommer Lawrence & Haug, LLP

(57) ABSTRACT

Recombinants containing and expressing lentivirus, retrovirus or immunodeficiency virus DNA and methods for making and using the same are disclosed and claimed. In an exemplified embodiment, attenuated recombinant viruses containing DNA encoding a feline immunodeficiency virus epitope such as an antigen, as well as methods and compositions employing the viruses, expression products therefrom, and antibodies generated from the viruses or expression products, are disclosed and claimed. The recombinants can be NYVAC or ALVAC recombinants. The DNA can encode at least one of: Env, Gag, Pol, or combinations thereof such as Gag and Pol or protease or Env, Gag and Pol or protease. The recombinants and gene products therefrom and antibodies generated by them have several preventive, therapeutic and diagnostic uses. DNA from the recombinants are useful as probes or, for generating PCR primers or for immunization. The immunogenicity and protective efficacy of immunization protocols involving ALVAC-FIV and priming with a recombinant canarypox virus ALVAC-FIV vaccine followed by a booster immunization with inactivated FIV-infected celled vaccine (ICV) was evaluated against FIV challenge in cats and the protocol was shown to effectively induce FIV-specific protective immune responses. Further, it was found that immunized cats were fully protected from an initial challenge with a slightly heterologous FIV strain ($50CID_{50}$) and were partially protected from a second challenge with a distinctly heterologous FIV strain ($75CID_{50}$) given eight months after the initial challenge without any intervening booster.

2 Claims, 11 Drawing Sheets

OTHER PUBLICATIONS

Clewell, D.B. and D.R. Helinski, Proc. Natl. Acad. Sci. USA 62, 1159-1166 (1969).
Clewell, D.B., J. Bacteriol 110, 667-676 (1972).
Cox, W.I., Tartaglia, J., and E. Paoletti. Virology 195, 845-850 (1993).
Daniel, M.D., Kirchhoff, F., Czajak, S.C., Sehgal, P.K., and Descssers, R., Science 258, 1938-1941 (1992).
Drillien et al., Virology 111, 488-499 (1981).
Edbauer, C., R. Weinberg, J. Taylor, A., Rey-Senelonge, J.F. Bouquet, P. Desmettre, and E. Paoletti, Virology 179, 901-904 (1990).
Eldridge, J.H., et al., Current Topics in Microbiology and Immunology, 146:59-66 (1989).
Emini, E., Schleif, W., Nunberg, J., Conley, A., Eda, Y., Tokiyoshi, S., Putney, S., Matsushita, S., Cobb, K., Jett, C., Eichberg, J., and K. Murthy, Nature 355, 728-730 (1992).
Engelke, D.R., Hoener, P.A., and Collins, F.S., Proc. Natl. Acad. Sci. USA 85, 544-548 (1988).
Englehard, V.H., Ann. Rev. Immunol. 12:181 (1994).
Franchini, G., Tartaglia, J., Markham, P., Benson, J., Fullen, J., Wills, M., Arp, J., Dekaban, G., Paoletti, E., and Gallo, R.C., AIDS Res. Hum. Retroviruses 11, 307-313 (1995).
Francini, G. Guroff, M.R. Tartaglia, J., Aggarwal, A., Abimiku, A., Benson, J., Markham, P., Limbach, K., Hurteau, G., Fullen, J., Aldrich, K., Miller, N., Sadoff, J., Paoletti, E., and Gallo, R.C., AIDS Res. Hum. Retroviruses 11, 909-920 (1995).
Fries et al., 32nd Interscience Conference on Antimicrobial Agents and Chemotherapy, Anaheim, CA (Oct. 1992).
Fries, L.F., Tartaglia, J., Taylor, J., Kauffman, E. K., Meignier, B., Paoletti, E., and Plotkin, S., Vaccine 14, 428-434 (1996).
Fultz, P., Nara, P., Barre-Sinoussi, F., Chaput, A., Greenberg, M., Muchmore, E., Kieny, M.-P and Girard, M. Science 256, 1687-1689 (1992).
Funahashi, S., T. Sato and H. Shida, J. Gen. Virol. 69, 35-47 (1988).
Gillard, S., Spehner, D., Drillien, R., and Kirn, A., Proc. Natl. Acad. Sci. USA 83, 5573-5577 (1986).
Girard, M., Kieny, M.-P., Pinter, A., Barre-Sinoussi, F., Nara, P., Kolbe, H., Kusui, K., Chaput, A., Reinhart, T., Muchmore, E., Ronco, J., Kaczorek, M., Gomard, E., Gluckman, J.-C. and Fultz, P., Proc. Natl. Acad. Sci. USA 88, 542-546 (1991).
Goebel, S.J., G.P. Johnson, M.E. Perkus, S.W. Davis, J.P. Winslow and E. Paoletti, Virology 179, 247-266 (1990b).
Goebel, S.J., Johnson, G.P., Perkus, M.E., Davis, S.W., Winslow, J.P., Paoletti, E., Virology 179, 247-266 (1990a).
Goldstein, D.J. and S.K. Weller, Virology 166, 41-51 (1988).
Goodman-Snitoff et al., J. Immunol. 147:410-415 (1991).
Guo, P., Goebel, S., Davis, S., Perkus, M.E., Languet, B., Desmettre, P., Allen, G., and Paoletti, E., J. Virol. 63, 4189-4198 (1989).
Guo et al., J. Virol. 64, 2399-2406 (1990).
Hardy, Jr., W.D. in Retrovirus Biology and Human Disease, Gallo, R.C. and Wong-Staal, eds., Marcel Dekker, New York, pp. 33-86, 1990.
Heeney, J.L., Holterman, L., ten Hoaft, P., et al., AIDS Res. Human. Retrovir. 10 Suppl. 2, S117-S121 (1994).
Hoise, M.J., Osborne, R. Yamamoto, J.K., Neil, J.C., and Jarrett, O. J. Virol. 69, 1253-1255 (1995).
Hruby, D.E. and L.A. Ball, J. Virol. 43, 403-409 (1982).
Hruby, D.E., R.A. Maki, D.B. Miller and L.A. Ball, Proc. Natl. Acad. Sci. USA 80, 3411-3415 (1983).
Hu, S.-L, Polacino, P., Klaniecki, J., Travis, B., Wrey, T., Pennathur, S., Stallard, V., Kornas, H., Langlois, A.J., and Benveniste, R.E. (1995) AIDS Research and Human Retrovirus 11:5136.
Hu, S.-L., Polacino, P. Stallard, V., Klaniecki, J., Pennathur, S., Travis, B.M., Misher, L., Kornas, H., Langlois, A.J., Morton, W.R., and Benveniste, R. Retroviruses of Human AIDS and Related Animal Diseases Nuviéme Colloque des Cent Gardeś; pp. 275-281, (1994).
Hu, S.-L., Abrams, K., Barber, G., Morn, P., Zarling, J., Langlois, A., Kuller, L., Morton, W. and Benveniste, R., Science 255, 456-459 (1992).

Lawrence, C., Weinhold, K., McElrath, J., Excler, J.L. Duliege, A.M., Clements, M.L., Belche, R., Dolin, R., and Graham, B., AVUE 022: safety and immunogenicity of live recombinant canarypox vector containing the envelope, gag and protease genes of HIV-1 in seronegative adult volunteers. XI International Conference on AIDS/Vancouver 1996/Mo.A.282 (1996).
Mandecki, W., Proc. Natl. Acad. Sci. USA 83, 7177-7182 (1986).
Naniatis, T., Fritsch, E.F., and Sambrook, J. In Molecular cloning: a laboratory manual, (Cold Spring Harbor Laboratory, Cold Spring Harbor, NY) (1982).
Matthews, R.E.F., Intervirology 17, 42-44 (1982).
Miller et al., J. Exp. Med. 176, 1739-1744 (1992).
Milstein, C., Scientific American 243, 66, 70 (1980).
Morgan, A.J., M. Mackett, S. Finerty, J.R. Arrand, F.T. Scullion and M.A. Epstein, J. Med. Virol. 25, 189-195 (1988).
Morikawa, S. and Bishop, D., Virol. 186, 389-397 (1992).
Moss, B., E. Winters and J. A. Cooper, J. Virol. 40, 387-395 (1981).
Nabel et al., Tibtech, May, 11, 211-215 (1993).
Okada, S. Ruiyu, P., Young, E., Stoffa, W.V., and Yamamoto, J.K., AIDS Res. and Human Retrovir. 10, 1739-1746 (1994).
Paez et al., PNAS USA 82, 3365-3369 (1985); see also Paez et al., Virology 169, 418-426 (1985).
Palumbo, G.J., Pickup, D.J., Fredrickson, T.N., Mcintyre, L.J., and Buller, R.M.L., Virology 172, 262-273 (1989).
Panicali, D., Davis, S.W., Mercer, S.R., and Paoletti, E., J. Virol. 37, 1000-1010 (1981).
Panicali, D. and E. Paoletti, Proc. Natl. Acad. Sci. USA 79, 4927-4931 (1982).
Patel, D.D. and Pickup, D.J., EMBO 6, 3787-3794 (1987).
Patel, D.D., Ray, C.A., Drucker, R.P., and Pickup, D.J., Proc. Natl. Acad. Sci. USA 85, 9431-9435 (1988).
Pederson, N.C., Ho, E.W., Brown, M.L., and Yamamoto, J.K., Science 235, 790-793 (1987).
Perkus, M.E., S.J. Goebel, S.W. Davis, G.P. Johnson, E.K. Norton and E. Paoletti, Virology 180, 406-410 (1991).
Perkus, M.E., Goebel, S.J., Davis, S.W., Johnson, G.P., Limbach, K., Norton, E.K., and Paoletti, E., Virology 179, 276-286 (1990).
Perkus, M.E., A. Piccini, B.R. Lipinskas and E. Paoletti, Science 229, 981-984 (1985).
Perkus, M.E., Limbach, K., and Paoletti, E., J. Virol. 63, 3829-3836 (1989).
Perkus, M. E., D. Panicali, S. Mercer and E. Paoletti, Virology 152, 285-297 (1986).
Pialoux et al., Aids Research and Human Retroviruses, 11(3):373-81 (1995).
Piccini, A., M.E. Perkus, and E. Paoletti, Methods in Enzymology 153, 545-563 (1987).
Pickup, D.J., B.S. Ink, B.L. Parsons, W. Hu and W.K. Joklik, Proc. Natl. Acad. Sci. USA 81, 6817-6821 (1984).
Pickup, D.J., B.S. Ink, W. Hu, C.A. Ray and W.K. Joklik, Proc. Natl. Acad. Sci. USA 83, 7698-7702 (1986).
Sadora, D.L., Shapaer, E.G., Kitchell, B.E., Dow, S.W., Hoover, E.A., and Mullins, J.I., J. Virol. 68 (1994).
Sanger, F., Nickel, S. Coulson, A.R., Proc. Natl. Acad. Sci. 74, 5463-5467 (1977).
Schmidtt, J.F.C. and H.G. Stunnenberg, J. Virol. 62, 1889-1897 (1988).
Shida, H., Virology 150, 451-462 (1986).
Shida, H., T. Tochikura, T. Sato, T. Konno, K. Hirayoshi, M. Seki, Y. Ito, M. Hatanaka, Y. Hinuma, M. Sugimoto, F. Takahashi-Nishimaki, T. Maruyama, K. Miki, K. Suzuki, M. Morita, H. Sashiyama and M. Hayami, EMBO 6, 3379-3384 (1987).
Shida, H., Hinuma, Y., Hatanaka, M., Morita, M., Kidokoro, M., Suzuki, K., Maruyzam, T., Takahashi-Nishimaki, F., Sugimoto, M., Kitamura, R., Miyazawa, T., and Hayami, M., J. Virol. 62, 4474-4480 (1988).
Slabaugh, M., N. Roseman, R. Davis and C. Mathews, J. Virol. 62, 519-527 (1988).
Song, W., Collison, E.W., Billingsley, P., and Brown, W.C. J. Virol. 66, 5409-5417 (1992).
Stanberry, L. R., S. Kit and M. G. Myers, J. Virol. 55, 322-328 (1985).

Tabor, S. and C. C. Richardson, Proc. Natl. Acad. Sci. USA 84, 4767-4771 (1987).

Tartaglia, J., Jarrett, O., Desmettre, P., Paoletti, E., J. Virol. 67, 2370-2375 (1993b).

Tartaglia, J., Perkus, M.E., Taylor, J., Norton, E.K., Audonnet, J.-C., Cox, W.I., Davis, S.W., Van Der Hoeven, J., Meignier, B., Riviere, M., Languet, B., Paoletti, E., Virology 188, 217-232 (1992).

Tartaglia, J., Pincus, S., Paoletti, E., Critical Reviews in Immunology 10, 13-30 (1990a).

Tartaglia, J., J. Taylor, W.I. Cox, J.-C. Audonnet, M.E. Perkus, A. Radaelli, C. de Giuli Morghen, B. Meignier, M. Riviere, K. Weinhold & E. Paoletti, In AIDS Research Reviews, W. Koff, F. Wong-Staal & R.C. Kenedy, Eds., vol. 3, Marcel Dekker, NY, pp. 361-378 (1993a).

Tartaglia, J. & E. Paoletti, In Immunochemistry of Viruses, II. The Basis for Serodiagnosis and Vaccines. M.H.V. van Regenmortel & A.R. Neurath, Eds. 125-151. Elsevier Science Publishers, Amsterdam (1990b).

Taylor, J., R. Weinberg, J. Tartaglia, C. Richardson, G. Alkhatib, D. Briedis, M. Appel, E. Norton & E. Paoletti, Virology 187, 321-328 (1992).

Taylor, J., Edbauer, C., Rey-Senelonge, A., Bouquet, J.-F., Norton, E., Goebel, S., Desmettre, P., Paoletti, E., J. Virol. 64, 1441-1450 (1990).

Taylor, J., Weinberg, R., Kawaoka, Y. Webster, R.G., and Paoletti, E., Vaccine 6, 504-508 (1988a).

Taylor, J., R. Weinberg, B. Lanquet, P. Desmettre, and E. Paoletti, Vaccine 6, 497-503 (1988b).

Taylor, G., E. J. Stott, G. Wertz and A. Ball, J. Gen. Virol. 72, 125-130 (1991a).

Taylor, J., C. Trimarchi, R. Weinberg, B. Languet, F. Guillemin, P. Desmettre and E. Paoletti, Vaccine 9, 190-193 (1991b).

Van der Ryst, E., Fultz, P.N., Tartaglia, J., Barre-Sinnousi, F., Paoletti, E., Nara, P., Meignier, B., Blondeau, C., Muchmore, E., and Girard, M., Protection from HIV-1 challenge in chimpanzees by immunization with a canarypox virus recombinant. XI International conference on AIDS/Vancouver/1996, We.A.280 (1996).

Verschoor, E.J., Willlemse, M.J., Stam, J.G., van A.L. W., Pouweis, H., Chalmers, S.K., Horzinek, M.C., Sandermeijer, P.J.A., Hesselink, W., and de Ronde, A., Vaccine 14, 285-289 (1996).

Vos, J. and Stunnenberg, H., EMBO J. 7, 3487-3492 (1988).

Wang, R-F and Mullins, J. I., Gene 153, 197-202 (1995).

Webster et al., Vaccine, 12(16), 1495-1498 (1994).

Weir, J.P. and B. Moss, J. Virol. 46, 530-537 (1983).

Yamamoto, J.K., Hohdatsu, T., Olmstead, R.A., Pu, R., Lowe, H. Zochlinski, H., Acevedo, V., Johnson, H.M., Soulds, G.A., and Gardner, M.B., J. Virol. 67, 601-605 (1993).

Yamamoto, J.K., Okuda, T., Ackley, C.D., Lowe, H. Zochlinski, H., Pembroke, E., and Gardner, M.B., AIDS Res. Human Retrovir. 7, 911-922 (1991).

Yuen, L., and Moss, B., Proc. Natl. Acad. Sci. USA 84, 6417-6421 (1987).

Zhou, J., L. Crawford, L. McLean, X. Sun, M. Stanley, N. Almond and G.L. Smith, J. Gen. Virol. 71, 2185-2190 (1990).

Hosie, M.J. "The Development of a Vaccine Against Feline Immunodeficiency Virus", Br. Vet. J. Jan.-Feb. (1994), 150(1), pp. 25-39.

Gotch et al. "High Frequency of Memory and Effector Gag Specific Cytotoxic T Lymphocytes in HIV Seropositive Individuals". Int. Immunol. (1990) 2(8), pp. 707-712.

Bryson, Y. J. "HIV Clearance In Infants—A Continuing Saga". AIDS. (1995) 9, pp. 1373-1375.

Pu et al. "Protection of Neonatal Kittens Against Feline Immunodeficiency Virus Infection with Passive Maternal Antiviral Antibodies". AIDS. Mar. (1995) 9(3), pp. 235-242.

Newell et al. "Vertical Transmission of HIV-1: Maternal Immune Status and Obstetric Factors. The European Collaborative Study." AIDS. (1996) 10(14), pp. 1675-1681.

Verschoor, et al. "Evaluation of Subunit Vaccines Against Feline Immunodeficiency Virus Infection." Vaccine. Mar. (1996), 1B(4), pp. 285-289.

Siebelink et al. "Neutralization of Feline Immunodeficiency Virus by Polyclonal Feline Antibody: Simultaneous Involvement of Hypervariable Regions 4 and 5 of the Surface Glycoprotein", J. Virol. Aug. (1995)69(8), pp. 5124-5127.

Siebelink et al. "Enhancement of Feline Immunodeficiency Virus Infection After Immunization with Envelope Glycoprotein Subunit Vaccines". J. Virol. Jun. 1995 69(6), pp. 3704-3711.

Gonin et al. "Immunization Trial of Cats With a Replication-Defective Adenovirus Type 5 Expressing the ENV Gene of Feline Immunodeficiency Virus". Vet. Microbiol. Aug. (1995) 45(4), pp. 393-401.

Siebelink et al. "Two Different Mutations in the Envelope Protein of Feline Immunodeficiency Virus Allow the Virus to Escape from Neutralization by Feline Serum Antibodies". Vet. Immunol. Immunopathol. May (1995) 46(1-2), pp. 51-59.

Gallimore et al. "Early Suppression of SIV Replication by CD8+nef-specific Cytotoxic T Cells in Vaccinated Macaques". Nat. Med. Nov. (1995) 1(11), pp. 1167-1173.

Rowland-Jones et al. "HIV-specific Cytotoxic T-cells in HIV-exposed but Uninfected Gambian Women", Curr. Opin. Immunol. Aug. (1995) 7(4), pp. 448-455

Osterhaus et al. "Accelerated Viremia in Cats Vaccinated with Recombinant Vaccinia Virus Expressing Envelope Glycoprotein of Feline Immunodeficiency Virus". AIDS Res. Human Retroviruses. Mar. (1996) 20, 12(5), pp. 437-441.

Flynn et al. "Involvement of gag- and env-Specific Cytotoxic T Lymphocytes in Protective Immunity to Feline Immunodeficiency Virus". AIDS Res. Hum. Retroviruses. Sep. (1995) 11(9), pp. 1107-1113.

Kent et al. "Analysis of Cytotoxic T Lymphocyte Response to SIV Proteins in SIV-Infected Macaques Using Antigen-Specific Stimulation with Recombinant Vaccinia and Fowl Poxviruses". AIDS Res. Hum. Retroviruses. May (1994) 10(5), pp. 551-560

Kent et al. "Passive Immunization of Cynomolgus Macaques with Immune Sera or a Pool of Neutralizing Antibodies Failed to Protect Against Challenge with SIV mac251". AIDS Res. Hum. Retroviruses. Feb. (1994) (2), pp. 189-194.

Rowland-Jones and McMichael. "Immune Responses in HIV-Exposed Seronegatives: Have They Repelled the Virus?" Cur. Opin. Immunol. Aug. (1995) 7(4), pp. 448-455.

Hosie, M. J. "Suppression of Virus Burden by Immunization with Feline Immunodeficiency Virus Env Protein". Apr. 14 (1996) (5), pp. 405-411.

Matteucci et al. "Vaccination Protexts Against In Vivo-Grown Feline Immunodeficiency Virus even in the absence of Detectable Neutralizing Antibodies". J. Virol. Jan. (1996) 70(1), pp. 617-622.

Lombardi et al. "A Neutralizing Antibody-Inducing Peptide of the V3 Domain of Feline Immunodficiency Virus Envelope Glycoprotein Does Not Induce Protective Immunity". J. Virol. Dec. (1994) 68(12), pp. 8374-8379.

Hohdatsu et al. "Passive Antibody Protection of Cats Against Feline Immunodeficiency Virus Infection". J. Virol. Apr. (1993) 67(4), pp. 2344-2348.

Bryson et al. "A child found to be HIV positive shortly after birth appears now to be clear of the infection". Nurs. Times. Apr. 12-18 (1995), 91(15), p. 11.

Prince et al. "Chimpanzees and AIDS Research". Nature. Jun. 9 (1988), 333, p. 513

Newell et al. "Detection of Virus in Vertically Exposed HIV-antibody-negative children".Lancet. Jan. 27 (1996), 347, pp. 213-215.

Rowland-Jones et al. "HIV-Specific Cytotoxic T-Cell Activity in an HIV-Exposed but Uninfected Infant". Lancet. Apr. (1993) 3, 341, pp. 860-861.

Hosie and Flynn. "Feline Immunodeficiency Virus Vaccination: Characterization of the Immune Correlates of Protection". J. Virol. Nov. (1996) 70(11), pp. 7561-7568.

Bryson et al. "Clearance of HIV Infection in a Perinatally Infected Infant". N. Engl. J. Med. Mar. (1995) 30, 332(13), pp. 833-838

Prince et al. "Failure of a Human Immunodeficiency Virus (HIV) Immune Globulin to Protect Chimpanzees Against Experimental Challenge with HIV". Proc. Natl. Acad. Sci. USA. Sep. (1988) 85(18), pp. 6944-6948.

Cheynier et al. "Cytotoxic T Lymphocyte Responses in the Peripheral Blood of Children Born to Human Immunodeficiency Virus-1-Infected Mothers". *Eur. J. Immunol.* Sep. (1992) 22(9), pp. 2211-2217.

Hosie et al. "Enhancement After Feline Immunodeficiency Virus Vaccination". *Vet. Immunol. Immunopathol.* Dec. (1992) 35(1-2), pp. 191-197.

Pincus et al., "Poxvirus-based vectors as vaccine candidates", Biologicals, 1995, vol. 23, pp. 159-164.

Olmsted et al., "Molecular cloning of feline immunodeficiency virus", Proc. Natl. Acad. Sci. USA, Apr. 1989, vol. 86, pp. 2448-2452.

Wardley et al., "The use of feline herpesvirus and baculovirus as vaccine vectors for the gag and env genes of feline leukaemia virus", J. Gen. Virol., 1992, vol. 73, pp. 1811-1818.

Beatty et al., "A longitudinal study of feline immunodeficiency virus-specific cytotoxic T lymphocytes in experimentally infected cats using antigen-specific induction", Journal of Virology, Sep. 1996, pp. 6199-6206.

J. Wojcik, "Expressionof feline immunodeficiency virus (FIV) gag gene in vaccinia virus vector", Acta Microbiologica Polonica, 1995, vol. 44, No.

Okuda et al., "Induction of potent humoral and cell-mediated immune responses following direct injection of DNA encoding the HIV type 1 env and rev gene products", AIDS Res. Human Retro., 1995, vol. 11, No. 8, pp. 933-943.

Gonda et al., "Bovine immunodeficiency virus: molecular biology and virus-host interaction", Virus Res., 1994, vol. 132, pp. 155-181.

Whetter et al., "Equine infectious anemia virus derived from a moelcular clone persistently infects horses", J. Virol., Dec. 1990, vol. 64, No. 12, pp. 5750-5756.

Andresson et al., "Nucleotide sequence and biological properties of a pathogenic proviral molecular clone of neurovirulent visna virus", 1993, vol. 193, pp. 89-105.

Saltarelli et al., "Nucleotide sequence and transcriptional analysis of molecular clones of CAEV which generate infectious virus", Virol., 1990, vol. 179, pp. 347-364.

Ichihashi, Y. and Dales, S., Virology 46, 533-543 (1971).

Issel, C.J., Horohov, D.W., Lea, D.F. et al., J. Virology 66, 3398-3408 (1992).

Itamura, S., H. Iinuma, H. Shida, Y. Morikawa, K. Nerome and A. Oya, J. Gen. Virol. 71, 2859-2865 (1990).

Jacobson, J.G., D.A. Leib, D.J. Goldstein, C.L. Bogard, P.A. Schaffer, S.K. Weller and D.M. Coen, Virology 173, 276-283 (1989).

Jamieson, A.T., G.A. Gentry and J.H. Subak-Sharpe, J. Gen. Virol. 24, 465-480 (1974).

Johnson, C.A., Torres, B.A., Koyama, H., and Yamamoto, J.K. AIDS Res. and Human. Retrovir. 10, 225-228 (1994).

Kato, S., M. Takahashi, S. Kameyama and J. Kamahora, Biken's 2, 353-363 (1959).

Kendrew, *In the Encyclopedia of Molecular Biology* (Blackwell Science Ltd.) (1995).

Konishi et al., Virology 190, 454-458 (1992).

Kotwal, G.J. and B. Moss, Virology 167, 524-537 (1988b).

Kotwal, G.J. and Moss, B., Nature (Lond.) 335, 176-178 (1988a).

Kotwal, G.J., S.N. Isaacs, R. McKenzie, M.M. Frank and B. Moss, Science 250, 827-830 (1990).

Kotwal, G.J., A.W. Hugin and B. Moss, Virology 171, 579-587 (1989a).

Kotwal, G.J. and B. Moss, J. Virol. 63, 600-606 (1989b).

Kuby, Janis, Immunology, pp. 79-81 (1992).

Lai et al., Virus Res. 12, 239-250 (1989).

\* cited by examiner

FIG. 2  Nucleotide sequence of FIV env from Rhone Merieux. The FIV env start codon is at position 1 and the stop codon is at position 2569. Plasmid ptg6184, containing the FIV env coding sequence, was from Rhone Merieux. The FIV env coding sequence in ptg6184 was sequenced and the following differences with the sequence below were observed: position 1218 T is G in ptg6184 changing phe to leu; position 1220 G to A changes gly to glu; and position 2201 C to A change ala to glu.

```
   1 ATGGCAGAAGGATTTGCAGCCAATAGACAATGGATAGGACCAGAAGAAGCTGAAGAGTTA
  61 TTAGATTTTGATATAGCAACACAAATGAGTGAAGAAGGACCACTAAATCCAGGAGTAAAC
 121 CCATTTAGGGTACCTGGAATAACAGAAAAAGAAAAGCAAAACTACTGTAACATATTACAA
 181 CCTAAGTTACAAGATCTAAGGAACGAAATTCAAGAGGTAAAACTGGAAGAAGGAAATGCA
 241 GGTAAGTTTAGAAGAGCAAGATTTTTAAGGTATTCTGATGAACAAGTATTGTCCCTGGTT
 301 CATGCGTTCATAGGATATTGTATATATTTAGGTAATCGAAATAAGTTAGGATCTTTAAGA
 361 CATGACATTGATATAGAAGCACCCCAAGAAGAGTGTTATAATAATAGAGAGAAGGGTACA
 421 ACTGACAATATAAAATATGGTAGACGATGTTGCCTAGGAACGGTGACTTTGTACCTGATT
 481 TTATTTATAGGATTAATAATATATTCACAGACAACCAACGCTCAGGTAGTATGGAGACTT
 541 CCACCATTAGTAGTCCCAGTAGAAGAATCAGAAATAATTTTTTGGGACTGTTGGGCACCA
 601 GAAGAACCCGCCTGTCAGGACTTTCTTGGGGCAATGATACATCTAAAAGCTAAGACAAAT
 661 ATAAGTATACGAGAGGGACCTACCTTGGGGAATTGGACTAGAGAAATATGGGCAACATTA
 721 TTCAAAAAGGCTACTAGACAATGTAGAAGAGGCAGAATATGGAAAGATGGAATGAGACT
 781 ATAACAGGACCATCAGGATGTGCTAATAACACATGTTATAATGTTTCAGTAATAGTACCT
 841 GATTATCAGTGTTATTTAGATAGAGTAGATACTTGGTTACAAGGGAAAATAAATATATCA
 901 TTATGTCTAACAGGAGGAAAAATGTTGTACAATAAAGTTACAAAACAATTAAGCTATTGT
 961 ACAGACCCATTACAAATCCCACTGATCAATTATACATTTGGACCTAATCAAACATGTATG
1021 TGGAATACTTCACAAATTCAGGACCCTGAAATACCAAAATGTGGATGGTGGAATCAAATG
1081 GCCTATTATAACAGTTGTAAATGGGAAGAGGCAAAGGTAAAGTTTCATTGTCAAAGAACA
1141 CAGAGTCAGCCTGGATCATGGCGTAGAGCAATCTCGTCATGGAAACAAAGAAATAGATGG
1201 GAGTGGAGACCAGATTTTGGAAGTAAAAAGGTGAAAATATCTCTACAGTGCAATAGCACA
1261 AAAAACCTAACCTTTGCAATGAGAAGTTCAGGAGATTATGGAGAAGTAACGGGAGCTTGG
1321 ATAGAGTTTGGATGTCATAGAAATAAATCAAAACATCATTCTGAAGCAAGGTTTAGAATT
1381 AGATGTAGATGGAATGTAGGATCCGATACCTCGCTCATTGATACATGTGGAAACACTCGA
1441 GATGTTTCAGGTGCGAATCCTGTAGATTGTACCATGTATTCAAATAAAATGTACAATTGT
1501 TCTTTACAAAATGGGTTTACTATGAAGGTAGATGACCTTATTGTGCATTTCAATATGACA
1561 AAAGCTGTAGAAATGTATAATATTGCTGGAAATTGGTCTTGTACATCTGACTTGCCATCG
1621 TCATGGGGGTATATGAATTGTAATTGTACAAATAGTAGTAGTAGTTATAGTGGTACTAAA
1681 ATGGCATGTCCTAGCAATCGAGGCATCTTAAGGAATTGGTATAACCCAGTAGCAGGATTA
1741 CGACAATCCTTAGAACAGTATCAAGTTGTAAAACAACCAGATTACTTAGTGGTCCCAGAG
1801 GAAGTCATGGAATATAAACCTAGAAGGAAAAGGGCAGCTATTCATGTTATGTTGGCTCTT
1861 GCAACAGTATTATCTATTGTCGGTGCAGGGACGGGGGCTACTGCTATAGGGATGGTAACA
1921 CAATACCACCAAGTTCTGGCAACCCATCAAGAAGCTATAGAAAAGGTGACTGAAGCCTTA
1981 AAGATAAACAACTTAAGATTAGTTACATTAGAGCATCAAGTACTAGTAATAGGATTAAAA
2041 GTAGAAGCTATGGAAAAATTTTTATATACAGCTTTCGCTATGCAAGAATTAGGATGTAAT
2101 CAAAATCAATTTTTCTGCAAAATCCCTCCTGGGTTGTGGACAAGGTATAATATGACTATA
2161 AATCAAACAATATGGAATCATGAAATATAACTTTGGGGGCATGGTATAACCAAACAAAA
2221 GATTTACAACAAAAGTTTTATGAAATAATAATGGACATAGAACAAAATAATGTACAAGGG
2281 AAAACAGGGATACAACAATTACAAAAGTGGGAAGATTGGGTAGGATGGATGGGAAATATT
2341 CCACAATATTTAAAGGGACTATTGGGAGGTATCTTGGGAATAGGATTAGGAGTGTTATTA
2401 TTGATTTTATGTTTACCTACATTGGTTGATTGTATAAGAAATTGTATCCACAAGATACTA
2461 GGATACACAGTAATTGCAATGCCTGAAGTAGAAGGAGAAGAAATACAACCACAAATGGAA
2521 TTGAGGAGAAATGGTAGGCAATGTGGCATGTCTGAAAAAGAGGAGGAATGA
```

Nucleotide sequence of FIV gag/pol coding sequences from
Rhone Merieux. The gag start codon is at position 1 and
the gag stop codon is at position 1414. The ribosomal
frameshift site is near position 1255. The frameshift is
-1 in relation to the gag open reading frame. The
frameshift goes into the pol open reading frame. The pol
stop codon is at position 4614. Plasmid ptg8133 from
Rhone Merieux contains the FIV gag/pol coding sequences.
Part of ptg8133 has been sequenced and the CG at
positions 577-578 below is GC in ptg8133, changing the
codon from arg to ala.

```
1     ATGGGGAATGGACAGGGGCGAGATTGGAAAATGGCCATTAAGAGATGTAGTAATGTTGCT
61    GTAGGAGTAGGGGGGAAGAGTAAAAAATTTGGAGAAGGGAATTTCAGATGGGCCATTAGA
121   ATGGCTAATGTATCTACAGGACGAGAACCTGGTGATATACCAGAGACTTTAGATCAACTA
181   AGGTTGGTTATTTGCGATTTACAAGAAAGAAGAGAAAAATTTGGATCTAGCAAAGAAATT
241   GATATGGCAATTGTGACATTAAAAGTCTTTGCGGTAGCAGGACTTTTGAATATGACGGTG
301   TCTACTGCTGCTGCAGCTGAAAATATGTATTCTCAAATGGGATTAGACACTAGGCCATCT
361   ATGAAAGAAGCAGGTGGAAAAGAGGAAGGCCCTCCACAGGCATATCCTATTCAAACAGTA
421   AATGGAGTACCACAATATGTAGCACTTGACCCAAAAATGGTGTCCATTTTTATGGAAAAG
481   GCAAGAGAAGGACTAGGAGGGGAGGAAGTTCAACTATGGTTTACTGCCTTCTCTGCAAAT
541   TTAACACCTACTGACATGGCCACATTAATAATGGCCCGACCAGGGTGCGCTGCAGATAAA
601   GAAATATTGGATGAAAGCTTAAAGCAACTGACAGCAGAATATGATCGCACACATCCCCCT
661   GATGCTCCCAGACCATTACCCTATTTTACTGCAGCAGAAATTATGGGTATAGGATTAACT
721   CAAGAACAACAAGCAGAAGCAAGATTTGCACCAGCTAGGATGCAGTGTAGAGCATGGTAT
781   CTCGAGGCATTAGGAAAATTGGCTGCCATAAAAGCTAAGTCTCCTCGAGCTGTGCAGTTA
841   AGACAAGGAGCTAAGGAAGATTATTCATCCTTTATAGACAGATTGTTTGCCCAAATAGAT
901   CAAGAACAAAATACAGCTGAAGTTAAGTTATATTTAAAACAGTCATTAAGCATAGCTAAT
961   GCTAATGCAGACTGTAAAAAGGCAATGAGCCACCTTAAGCCAGAAAGTACCCTAGAAGAA
1021  AAGTTGAGAGCTTGTCAAGAAATAGGCTCACCAGGATATAAAATGCAACTCTTGGCAGAA
1081  GCTCTTACAAAAGTTCAAGTAGTGCAATCAAAAGGATCAGGACCAGTGTGTTTTAATTGT
1141  AAAAAACCAGGACATCTAGCAAGACAATGTAGAGAAGTGAAAAAATGTAATAAATGTGGA
1201  AAACCTGGTCATCTAGCTGCCAAATGTTGGCAAGGAAATAGAAAGAATTCGGGAAACTGG
1261  AAGGCGGGGCGAGCTGCAGCCCCAGTGAATCAAATGCAGCAAGCAGTAATGCCATCTGCA
1321  CCTCCAATGGAGGAGAAACTATTGGATTTATAAATTATAATAAAGTAGGTACGACTACAA
1381  CATTAGAAAAGAGGCCAGAAATACTTATATTTGTAAATGGATATCCTATAAAATTTTTAT
1441  TAGATACAGGAGCAGATATAACAATTTTAAATAGGAGAGATTTTCAAGTAAAAAATTCTA
1501  TAGAAAATGGAAGGCAAAATATGATTGGAGTAGGAGGAGGAAAGAGAGGAACAAATTATA
1561  TTAATGTACATTTAGAGATTAGAGATGAAAATTATAAGACACAATGTATATTTGGTAATG
1621  TTTGTGTCTTAGAAGATAACTCATTAATACAACCATTATTGGGGAGAGATAATATGATTA
1681  AATTCAATATTAGGTTAGTAATGGCTCAAATTTCTGATAAGATTCCAGTAGTAAAAGTAA
1741  AAATGAAGGATCCTAATAAAGGACCTCAAATAAAACAATGGCCATTAACAAATGAAAAAA
1801  TTGAAGCCTTAACAGAAATAGTAGAAAGACTAGAAAGAGAAGGGAAAGTAAAAAGAGCAG
1861  ATCCAAATAATCCATGGAATACACCAGTATTTGCTATAAAAAAGAAAAGTGGAAAATGGA
1921  GAATGCTCATAGATTTTAGAGAATTAAACAAACTAACTGAGAAAGGAGCAGAGGTCCAGT
1981  TGGGACTACCTCATCCTGCTGGGTTACAAATAAAAAAACAAGTAACAGTATTAGATATAG
2041  GGGATGCATATTTCACCATTCCTCTTGATCCAGATTATGCTCCTTATACAGCATTTACTT
2101  TACCTAGGAAAAATAATGCGGGACCAGGAAGGAGATTTGTGTGGTGTAGTCTACCACAAG
2161  GCTGGATTTTAAGTCCATTGATATATCAAAGTACATTAGATAATATAATACAACCTTTTA
2221  TTAGACAAAATCCTCAATTAGATATTTACCAATATATGGATGACATTTATATAGGATCAA
2281  ATTTAAGTAAAAAGGAGCATAAAGAAAAGGTAGAAGAATTAAGAAAATTACTATTATGGT
2341  GGGGATTTGAAACTCCAGAAGATAAATTACAGGAAGAACCCCCATATACATGGATGGGTT
2401  ATGAATTACATCCATTAACATGGACAATACAACAGAAACAGTTAGACATTCCAGAACAGC
2461  CCACTCTAAATGAGTTGCAAAAATTAGCAGGAAAAATTAATTGGGCTAGCCAAGCTATTC
```

FIG. 3A

| FIG. 3 | FIG. 3A |
|        | FIG. 3B |

```
2521 CAGACTTGAGTATAAAAGCATTAACTAACATGATGAGAGGAAATCAAAACCTAAATTCAA
2581 CAAGACAATGGACTAAAGAAGCTCGACTGGAAGTACAAAAGGCAAAAAAGGCTATAGAAG
2641 AACAAGTACAACTAGGATACTATGACCCCAGTAAGGAGTTATATGCTAAATTAAGTTTGG
2701 TGGGACCACATCAAATAAGTTATCGAGTATATCAGAAGGATCAAGAAAAGATACTATGGT
2761 ATGGAAAAATGAGTAGACAAAAGAAAAAGGCAGAAAATACATGTGATATAGCCTTAAGAG
2821 CATGCTATAAGATAAGAGAAGAGTCTATTATAAGAATAGGAAAAGAACCAAGATATGAAA
2881 TACCTACTTCTAGAGAAGCCTGGGAATCAAATCTAATTAATTCACCATATCTTAAGGCCC
2941 CACCTCCTGAGGTAGAATATATCCATGCTGCTTTGAATATAAAGAGAGCGTTAAGTATGA
3001 TAAAAGATGCTCCAATACCAGGAGCAGAAACATGGTATATAGATGGAGGTAGAAAACTAG
3061 GAAAAGCAGCAAAAGCAGCCTATTGGACAGATACAGGAAAGTGGAAAGTGATGGAATTAG
3121 AAGGCAGTAATCAGAAGGCAGAAATACAAGCATTATTATTGGCATTAAAAGCAGGATCAG
3181 AGGAGATGAATATTATAACAGATTCACAATATGCTATAAATATTATTCTTCAACAACCAG
3241 ATATGATGGAGGGAATCTGGCAAGAAGTTTTAGAAGAATTGGAGAAGAAAACAGCAATAT
3301 TTATAGATTGGGTCCCAGGACATAAAGGTATTCCAGGAAATGAGGAAGTAGATAAGCTTT
3361 GTCAAACAATGATGATAATAGAAGGGGATGGGATATTAGACAAAAGGTCAGAAGATGCAG
3421 GATATGATTTATTAGCTGCAAAAGAAATACATTTATTGCCAGGAGAGGTAAAAGTAATAC
3481 CAACAGGGGTAAAGCTAATGCTGCCTAAAGGACATTGGGGATTAATAATCGGAAAAAGCT
3541 CGATGGGGAGTAAAGGATTGGATGTATTAGGAGGAGTAATAGATGAAGGATATCGAGGTG
3601 AAATTGGAGTAATAATGATTAATGTATCAAGAAAATCAATCACCTTAATGGAACGACAAA
3661 AGATAGCACAATTAATAATACTGCCTTGTAAACATGAAGTATTAGAACAAGGAAAAGTAG
3721 TAAGGGATTCAGAGAGAGGAGGCAATGGTTATGGGTCAACAGGAGTATTCTCCTCTTGGG
3781 TTGACAGAATTGAGGAAGCAGAAATAAATCATGAAAAATTTCACTCAGATCCACAGTACT
3841 TAAGGACTGAATTTAATTTACCTAAAATGGTAGCAGAAGAGATAAGACGAAAATGCCCAG
3901 TATGCAGAATCAGAGGAGAACAAGTGGGAGGACAATTGAAAATAGGGCCTGGTATCTGGC
3961 AAATGGATTGCACACACTTTGATGGCAAAATAATTCTTGTGGGTATACATGTGGAATCAG
4021 GATATATATGGGCACAAATAATTTCTCAAGAAACTGCTGACTGTACAGTTAAAGCTGTTT
4081 TACAATTGTTGAGTGCTCATAATGTTACTGAATTACAAACAGATAATGGACCAAATTTTA
4141 AAAATCAAAAGATGGAAGGAGTACTCAATTACATGGGTGTGAAACATAAGTTTGGTATCC
4201 CAGGGAACCCACAGTCACAAGCATTAGTTGAAAATGTAAATCATACATTAAAAGTTTGGA
4261 TTCGGAAATTTTTGCCTGAAACAACCTCCTTGGATAATGCCTTATCTCTCGCTGTACATA
4321 GTCTCAATTTTAAAAGAAGAGGTAGGATAGGAGGGATGGCCCCTTATGAATTATTAGCAC
4381 AACAAGAATCCTTAAGAATACAAGATTATTTTTCTGCAATACCACAAAAATTGCAAGCAC
4441 AGTGGATTTATTATAAAGATCAAAAGATAAGAAATGGAAGGACCAATGAGAGTAGAAT
4501 ACTGGGGACAGGGATCAGTATTATTAAAGGATGAAGAGAAGGGATATTTTCTTATACCTA
4561 GGAGACACATAAGGAGAGTTCCAGAACCCTGCGCTCTTCCTGAAGGGGATGAGTGA
```

| | FIG. 3A |
|---|---|
| FIG. 3B | FIG. 3 |
| | FIG. 3B |

FIG. 4   Sequence comprised in the C6 donor plasmid pC6L. Plasmid pC6L contains the C6 insertion sites SmaI (position 409) and EcoRI (position 425).

```
1     GAGCTCGCGGCCGCCTATCAAAAGTCTTAATGAGTTAGGTGTAGATAGTATAGATATTAC
61    TACAAAGGTATTCATATTTCCTATCAATTCTAAAGTAGATGATATTAATAACTCAAAGAT
121   GATGATAGTAGATAATAGATACGCTCATATAATGACTGCAAATTTGGACGGTTCACATTT
181   TAATCATCACGCGTTCATAAGTTTCAACTGCATAGATCAAAATCTCACTAAAAAGATAGC
241   CGATGTATTTGAGAGAGATTGGACATCTAACTACGCTAAAGAAATTACAGTTATAAATAA
301   TACATAATGGATTTTGTTATCATCAGTTATATTTAACATAAGTACAATAAAAAGTATTAA
361   ATAAAAATACTTACTTACGAAAAAATGACTAATTAGCTATAAAAACCCGGGCTGCAGCTC
421   GAGGAATTCTTTTTATTGATTAACTAGTCAAATGAGTATATATAATTGAAAAAGTAAAAT
481   ATAAATCATATAATAATGAAACGAAATATCAGTAATAGACAGGAACTGGCAGATTCTTCT
541   TCTAATGAAGTAAGTACTGCTAAATCTCCAAAATTAGATAAAAATGATACAGCAAATACA
601   GCTTCATTCAACGAATTACCTTTTAATTTTTTCAGACACACCTTATTACAAACTAACTAA
661   GTCAGATGATGAGAAAGTAAATATAAATTTAACTTATGGGTATAATATAATAAAGATTCA
721   TGATATTAATAATTTACTTAACGATGTTAATAGACTTATTCCATCAACCCCTTCAAACCT
781   TTCTGGATATTATAAAATACCAGTTAATGATATTAAAATAGATTGTTTAAGAGATGTAAA
841   TAATTATTTGGAGGTAAAGGATATAAAATTAGTCTATCTTTCACATGGAAATGAATTACC
901   TAATATTAATAATTATGATAGGAATTTTTTAGGATTTACAGCTGTTATATGTATCAACAA
961   TACAGGCAGATCTATGGTTATGGTAAAACACTGTAACGGGAAGCAGCATTCTATGGTAAC
1021  TGGCCTATGTTTAATAGCCAGATCATTTTACTCTATAAACATTTTACCACAAATAATAGG
1081  ATCCTCTAGATATTTAATATTATATCTAACAACAACAAAAAAATTTAACGATGTATGGCC
1141  AGAAGTATTTCTACTAATAAAGATAAAGATAGTCTATCTTATCTACAAGATATGAAAGA
1201  AGATAATCATTTAGTAGTAGCTACTAATATGGAAAGAAATGTATACAAAAACGTGGAAGC
1261  TTTTATATTAAATAGCATATTACTAGAAGATTTAAAATCTAGACTTAGTATAACAAAACA
1321  GTTAAATGCCAATATCGATTCTATATTTCATCATAACAGTAGTACATTAATCAGTGATAT
1381  ACTGAAACGATCTACAGACTCAACTATGCAAGGAATAAGCAATATGCCAATTATGTCTAA
1441  TATTTTAACTTTAGAACTAAAACGTTCTACCAATACTAAAAATAGGATACGTGATAGGCT
1501  GTTAAAAGCTGCAATAAATAGTAAGGATGTAGAAGAAATACTTTGTTCTATACCTTCGGA
1561  GGAAAGAACTTTAGAACAACTTAAGTTTAATCAAACTTGTATTTATGAAGGTACC
```

FIG. 5 Predicted nucleotide sequence of the vCP242 insertion. The H6 promotor starts at position 55. The FIV env start codon is at position 179, and the FIV env stop codon is at position 2749. Positions 1 through 54 and positions 2750 through 2879 flank the H6/FIV env expression cassette.

```
1    TTAAATAAAAATACTTACTTACGAAAAATGACTAATTAGCTATAAAAACCCGGGTTCTTT
61   ATTCTATACTTAAAAAGTGAAAATAAATACAAAGGTTCTTGAGGGTTGTGTTAAATTGAA
121  AGCGAGAAATAATCATAAATTATTTCATTATCGCGATATCCGTTAAGTTTGTATCGTAAT
181  GGCAGAAGGATTTGCAGCCAATAGACAATGGATAGGACCAGAAGAAGCTGAAGAGTTATT
241  AGATTTTGATATAGCAACACAAATGAGTGAAGAAGGACCACTAAATCCAGGAGTAAACCC
301  ATTTAGGGTACCTGGAATAACAGAAAAAGAAAAGCAAAACTACTGTAACATATTACAACC
361  TAAGTTACAAGATCTAAGGAACGAAATTCAAGAGGTAAAACTGGAAGAAGGAAATGCAGG
421  TAAGTTTAGAAGAGCAAGATTTTTAAGGTATTCTGATGAACAAGTATTGTCCCTGGTTCA
481  TGCGTTCATAGGATATTGTATATATTTAGGTAATCGAAATAAGTTAGGATCTTTAAGACA
541  TGACATTGATATAGAAGCACCCCAAGAAGAGTGTTATAATAATAGAGAGAAGGGTACAAC
601  TGACAATATAAAATATGGTAGACGATGTTGCCTAGGAACGGTGACTTTGTACCTGATTTT
661  ATTTATAGGATTAATAATATATTCACAGACAACCAACGCTCAGGTAGTATGGAGACTTCC
721  ACCATTAGTAGTCCCAGTAGAAGAATCAGAAATAATTTTTTGGGACTGTTGGGCACCAGA
781  AGAACCCGCCTGTCAGGACTTTCTTGGGGCAATGATACATCTAAAAGCTAAGACAAATAT
841  AAGTATACGAGAGGGACCTACCTTGGGGAATTGGACTAGAGAAATATGGGCAACATTATT
901  CAAAAAGGCTACTAGACAATGTAGAAGAGGCAGAATATGGAAAAGATGGAATGAGACTAT
961  AACAGGACCATCAGGATGTGCTAATAACACATGTTATAATGTTTCAGTAATAGTACCTGA
1021 TTATCAGTGTTATTTAGATAGAGTAGATACTTGGTTACAAGGGAAAATAAATATATCATT
1081 ATGTCTAACAGGAGGAAAAATGTTGTACAATAAAGTTACAAAACAATTAAGCTATTGTAC
1141 AGACCCATTACAAATCCCACTGATCAATTATACATTTGGACCTAATCAAACATGTATGTG
1201 GAATACTTCACAAATTCAGGACCCTGAAATACCAAAATGTGGATGGTGGAATCAAATGGC
1261 CTATTATAACAGTTGTAAATGGGAAGAGGCAAAGGTAAAGTTTCATTGTCAAAGAACACA
1321 GAGTCAGCCTGGATCATGGCGTAGAGCAATCTCGTCATGGAAACAAAGAAATAGATGGGA
1381 GTGGAGACCAGATTTGGAAAGTAAAAAGGTGAAAATATCTCTACAGTGCAATAGCACAAA
1441 AAACCTAACCTTTGCAATGAGAAGTTCAGGAGATTATGGAGAAGTAACGGGAGCTTGGAT
1501 AGAGTTTGGATGTCATAGAAATAAATCAAAACATCATTCTGAAGCAAGGTTTAGAATTAG
1561 ATGTAGATGGAATGTAGGATCCGATACCTCGCTCATTGATACATGTGGAAACACTCGAGA
1621 TGTTTCAGGTGCGAATCCTGTAGATTGTACCATGTATTCAAATAAAATGTACAATTGTTC
1681 TTTACAAAATGGGTTTACTATGAAGGTAGATGACCTTATTGTGCATTTCAATATGACAAA
1741 AGCTGTAGAAATGTATAATATTGCTGGAAATTGGTCTTGTACATCTGACTTGCCATCGTC
1801 ATGGGGGTATATGAATTGTAATTGTACAAATAGTAGTAGTAGTTATAGTGGTACTAAAAT
1861 GGCATGTCCTAGCAATCGAGGCATCTTAAGGAATTGGTATAACCCAGTAGCAGGATTACG
1921 ACAATCCTTAGAACAGTATCAAGTTGTAAAACAACCAGATTACTTAGTGGTCCCAGAGGA
1981 AGTCATGGAATATAAACCTAGAAGGAAAAGGGCAGCTATTCATGTTATGTTGGCTCTTGC
2041 AACAGTATTATCTATTGTCGGTGCAGGGACGGGGGCTACTGCTATAGGGATGGTAACCCA
2101 ATACCACCAAGTTCTGGCAACCCATCAAGAAGCTATAGAAAAGGTGACTGAAGCCTTAAA
2161 GATAAACAACTTAAGATTAGTTACATTAGAGCATCAAGTACTAGTAATAGGATTAAAAGT
2221 AGAAGCTATGGAAAAATTCTTATATACAGCTTTCGCTATGCAAGAATTAGGATGTAATCA
2281 AAATCAATTCTTCTGCAAAATCCCTCCTGGGTTGTGGACAAGGTATAATATGACTATAAA
2341 TCAAACAATATGGAATCATGGAAATATAACTTTGGGGGAATGGTATAACCAAACAAAAGA
2401 TTTACAACAAAAGTTTTATGAAATAATAATGGACATAGAACAAAATAATGTACAAGGGAA
2461 AACAGGGATACAACAATTACAAAAGTGGGAAGATTGGGTAGGATGGATGGGAAATATTCC
2521 ACAATATTTAAAGGGACTATTGGGAGGTATCTTGGGAATAGGATTAGGAGTGTTATTATT
2581 GATTTTATGTTTACCTACATTGGTTGATTGTATAAGAAATTGTATCCACAAGATACTAGG
2641 ATACACAGTAATTGCAATGCCTGAAGTAGAAGGAGAAGAAATACAACCACAAATGGAATT
2701 GAGGAGAAATGGTAGGCAATGTGGCATGTCTGAAAAAGAGGAGGAATGATGAAGTATCTC
2761 AGAATTCCTGCAGCCCGGGGGATCCTTAATTAATTAGTTATTAGACAAGGTGAAAACGAA
2821 ACTATTTGTAGCTTAATTAATTAGCTGCAGGAATTCTTTTTATTGATTAACTAGTCAAA
```

FIG. 6   Predicted nucleotide sequence of I3L promoted FIV
        gag/protease expression cassette and flanking regions in
        vCP253. The I3L promoter begins at position 135. The
        gag start codon is at position 235 and the protease stop
        codon is at position 1648.

```
1     TTAATCAATAAAAAGAATTCCTGCAGCCCTGCAGCTAATTAATTAAGCTACAAATAGTTT
61    CGTTTTCACCTTGTCTAATAACTAATTAATTAAGGATCCCCCGTACCGGGCCCCCCCTCG
121   AGGTCGACATCGATACATCATGCAGTGGTTAAACAAAAACATTTTTATTCTCAAATGAGA
181   TAAAGTGAAAATATATATCATTATATTACAAAGTACAATTATTTAGGTTTAATCATGGGG
241   AATGGACAGGGGCGAGATTGGAAAATGGCCATTAAGAGATGTAGTAATGTTGCTGTAGGA
301   GTAGGGGGGAAGAGTAAAAAATTTGGAGAAGGGAATTTCAGATGGGCCATTAGAATGGCT
361   AATGTATCTACAGGACGAGAACCTGGTGATATACCAGAGACTTTAGATCAACTAAGGTTG
421   GTTATTTGCGATTTACAAGAAAGAAGAGAAAAATTTGGATCTAGCAAAGAAATTGATATG
481   GCAATTGTGACATTAAAAGTCTTTGCGGTAGCAGGACTTTTGAATATGACGGTGTCTACT
541   GCTGCTGCAGCTGAAAATATGTATTCTCAAATGGGATTAGACACTAGGCCATCTATGAAA
601   GAAGCAGGTGGAAAAGAGGAAGGCCCTCCACAGGCATATCCTATTCAAACAGTAAATGGA
661   GTACCACAATATGTAGCACTTGACCCAAAAATGGTGTCCATTTTCATGGAAAAGGCAAGA
721   GAAGGACTAGGAGGGGAGGAAGTTCAACTATGGTTTACTGCCTTCTCTGCAAATTTAACA
781   CCTACTGACATGGCCACATTAATAATGGCCGCACCAGGGTGCGCTGCAGATAAAGAAATA
841   TTGGATGAAAGCTTAAAGCAACTGACAGCAGAATATGATCGCACACATCCCCCTGATGCT
901   CCCAGACCATTACCCTATTTTACTGCAGCAGAAATTATGGGTATAGGATTAACTCAAGAA
961   CAACAAGCAGAAGCAAGATTTGCACCAGCTAGGATGCAGTGTAGAGCATGGTATCTCGAG
1021  GCATTAGGAAAATTGGCTGCCATAAAAGCTAAGTCTCCTCGAGCTGTGCAGTTAAGACAA
1081  GGAGCTAAGGAAGATTATTCATCCTTTATAGACAGATTGTTTGCCCAAATAGATCAAGAA
1141  CAAAATACAGCTGAAGTTAAGTTATATTTAAAACAGTCATTAAGCATAGCTAATGCTAAT
1201  GCAGACTGTAAAAAGGCAATGAGCCACCTTAAGCCAGAAAGTACCCTAGAAGAAAAGTTG
1261  AGAGCTTGTCAAGAAATAGGCTCACCAGGATATAAAATGCAACTCTTGGCAGAAGCTCTT
1321  ACAAAAGTTCAAGTAGTGCAATCAAAAGGATCAGGACCAGTGTGTTTAATTGTAAAAAA
1381  CCAGGACATCTAGCAAGACAATGTAGAGAAGTGAAAAAATGTAATAAATGTGGAAAACCT
1441  GGTCATCTAGCTGCCAAATGTTGGCAAGGAAATAGAAAGAATTCGGGAAACTGGAAGGCG
1501  GGGCGAGCTGCAGCCCCAGTGAATCAAATGCAGCAAGCAGTAATGCCATCTGCACCTCCA
1561  ATGGAGGAGAAACTATTGGATTTATAAATTATAATAAAGTAGGTACGACTACAACATTAG
1621  AAAAGAGGCCAGAAATACTTATATTTGTAAATGGATATCCTATAAAATTTTTATTAGATA
1681  CAGGAGCAGATATAACAATTTTAAATAGGAGAGATTTTCAAGTAAAAAATTCTATAGAAA
1741  ATGGAAGGCAAAATATGATTGGAGTAGGAGGAGGAAAGAGAGGAACAAATTATATTAATG
1801  TACATTTAGAGATTAGAGATGAAAATTATAAGACACAATGTATATTTGGTAATGTTTGTG
1861  TCTTAGAAGATAACTCATTAATACAACCATTATTGGGGAGAGATAATATGATTAAATTCA
1921  ATATTAGGTTAGTAATGGCTCAATAATTTTATCCCGGGTTTTTATAGCTAATTAGTCATT
1981  TTTCGTAAGTAAGTATTTTTATTTAATACTTTTTATTGTACTTATGTTAAAT
```

Predicted nucleotide sequence of the H6 promoted FIV env/I3L promoted FIV gag/protease expression cassette and flanking regions in vCP255. The H6 promotor starts at position 129, the FIV env start codon is at position 253, and the FIV env stop codon is at position 2823. The I3L promotor starts at position 2830, the FIV gag start codon is at position 2930 and the FIV gag stop codon is at position 4282. The ribosomal frameshift site is near position 4184. The frameshift is -1 in relation to the gag open reading frame. The frameshift goes into the pol open reading frame. The stop codon for the protease gene is at position 4641. Positions 1 through 128 and positions 4642 through 4727 flank the H6 FIV env/I3L FIV gag/protease expression cassette.

```
1    TTAATCAATAAAAAGAATTCCTGCAGCCCTGCAGCTAATTAATTAAGCTACAAATAGTTT
61   CGTTTTCACCTTGTCTAATAACTAATTAATTAAGGATCCCCCGTACCGGCCCCCCCTCG
121  AGGTCGACTTCTTTATTCTATACTTAAAAAGTGAAAATAAATACAAAGGTTCTTGAGGGT
181  TGTGTTAAATTGAAAGCGAGAAATAATCATAAATTATTTCATTATCGCGATATCCGTTAA
241  GTTTGTATCGTAATGGCAGAAGGATTTGCAGCCAATAGACAATGGATAGGACCAGAAGAA
301  GCTGAAGAGTTATTAGATTTTGATATAGCAACACAAATGAGTGAAGAAGGACCACTAAAT
361  CCAGGAGTAAACCCATTTAGGGTACCTGGAATAACAGAAAAAGAAAAGCAAAACTACTGT
421  AACATATTACAACCTAAGTTACAAGATCTAAGGAACGAAATTCAAGAGGTAAAACTGGAA
481  GAAGGAAATGCAGGTAAGTTTAGAAGAGCAAGATTTTTAAGGTATTCTGATGAACAAGTA
541  TTGTCCCTGGTTCATGCGTTCATAGGATATTGTATATATTTAGGTAATCGAAATAAGTTA
601  GGATCTTTAAGACATGACATTGATATAGAAGCACCCCAAGAAGAGTGTTATAATAATAGA
661  GAGAAGGGTACAACTGACAATATAAAATATGGTAGACGATGTTGCCTAGGAACGGTGACT
721  TTGTACCTGATTTTATTTATAGGATTAATAATATATTCACAGACAACCAACGCTCAGGTA
781  GTATGGAGACTTCCACCATTAGTAGTCCCAGTAGAAGAATCAGAAATAATTTTTTGGGAC
841  TGTTGGGCACCAGAAGAACCCGCCTGTCAGGACTTTCTTGGGGCAATGATACATCTAAAA
901  GCTAAGACAAATATAAGTATACGAGAGGGACCTACCTTGGGGAATTGGACTAGAGAAATA
961  TGGGCAACATTATTCAAAAAGGCTACTAGACAATGTAGAAGAGGCAGAATATGGAAAAGA
1021 TGGAATGAGACTATAACAGGACCATCAGGATGTGCTAATAACACATGTTATAATGTTTCA
1081 GTAATAGTACCTGATTATCAGTGTTATTTAGATAGAGTAGATACTTGGTTACAAGGGAAA
1141 ATAAATATATCATTATGTCTAACAGGAGGAAAAATGTTGTACAATAAAGTTACAAAACAA
1201 TTAAGCTATTGTACAGACCCATTACAAATCCCACTGATCAATTATACATTTGGACCTAAT
1261 CAAACATGTATGTGGAATACTTCACAAATTCAGGACCCTGAAATACCAAAATGTGGATGG
1321 TGGAATCAAATGGCCTATTATAACAGTTGTAAATGGGAAGAGGCAAAGGTAAAGTTTCAT
1381 TGTCAAAGAACACAGAGTCAGCCTGGATCATGGCGTAGAGCAATCTCGTCATGGAAACAA
1441 AGAAATAGATGGGAGTGGAGACCAGATTTGGAAAGTAAAAAGGTGAAAATATCTCTACAG
1501 TGCAATAGCACAAAAAACCTAACCTTTGCAATGAGAAGTTCAGGAGATTATGGAGAAGTA
1561 ACGGGAGCTTGGATAGAGTTTGGATGTCATAGAAATAAATCAAAACATCATTCTGAAGCA
1621 AGGTTTAGAATTAGATGTAGATGGAATGTAGGATCCGATACCTCGCTCATTGATACATGT
1681 GGAAACACTCGAGATGTTTCAGGTGCGAATCCTGTAGATTGTACCATGTATTCAAATAAA
1741 ATGTACAATTGTTCTTTACAAAATGGGTTTACTATGAAGGTAGATGACCTTATTGTGCAT
1801 TTCAATATGACAAAAGCTGTAGAAATGTATAATATTGCTGGAAATTGGTCTTGTACATCT
1861 GACTTGCCATCGTCATGGGGGTATATGAATTGTAATTGTACAAATAGTAGTAGTAGTTAT
1921 AGTGGTACTAAAATGGCATGTCCTAGCAATCGAGGCATCTTAAGGAATTGGTATAACCCA
1981 GTAGCAGGATTACGACAATCCTTAGAACAGTATCAAGTTGTAAAACAACCAGATTACTTA
2041 GTGGTCCCAGAGGAAGTCATGGAATATAAACCTAGAAGGAAAAGGGCAGCTATTCATGTT
2101 ATGTTGGCTCTTGCAACAGTATTATCTATTGTCGGTGCAGGGACGGGGGCTACTGCTATA
2161 GGGATGGTAACCCAATACCACCAAGTTCTGGCAACCCATCAAGAAGCTATAGAAAAGGTG
2221 ACTGAAGCCTTAAAGATAAACAACTTAAGATTAGTTACATTAGAGCATCAAGTACTAGTA
2281 ATAGGATTAAAAGTAGAAGCTATGGAAAAATTCTTATATACAGCTTTCGCTATGCAAGAA
2341 TTAGGATGTAATCAAAATCAATTCTTCTGCAAAATCCCTCCTGGGTTGTGGACAAGGTAT
```

FIG. 7A

| FIG. 7 | FIG. 7A |
|---|---|
| | FIG. 7B |

```
2401 AATATGACTATAAATCAAACAATATGGAATCATGGAAATATAACTTTGGGGGAATGGTAT
2461 AACCAAACAAAAGATTTACAACAAAAGTTTTATGAAATAATAATGGACATAGAACAAAAT
2521 AATGTACAAGGGAAAACAGGGATACAACAATTACAAAAGTGGGAAGATTGGGTAGGATGG
2581 ATGGGAAATATTCCACAATATTTAAAGGGACTATTGGGAGGTATCTTGGGAATAGGATTA
2641 GGAGTGTTATTATTGATTTTATGTTTACCTACATTGGTTGATTGTATAAGAAATTGTATC
2701 CACAAGATACTAGGATACACAGTAATTGCAATGCCTGAAGTAGAAGGAGAAGAAATACAA
2761 CCACAAATGGAATTGAGGAGAAATGGTAGGCAATGTGGCATGTCTGAAAAAGAGGAGGAA
2821 TGAATCGATACATCATGCAGTGGTTAAACAAAAACATTTTTATTCTCAAATGAGATAAAG
2881 TGAAAATATATATCATTATATTACAAAGTACAATTATTTAGGTTTAATCATGGGGAATGG
2941 ACAGGGGCGAGATTGGAAAATGGCCATTAAGAGATGTAGTAATGTTGCTGTAGGAGTAGG
3001 GGGGAAGAGTAAAAAATTTGGAGAAGGGAATTTCAGATGGGCCATTAGAATGGCTAATGT
3061 ATCTACAGGACGAGAACCTGGTGATATACCAGAGACTTTAGATCAACTAAGGTTGGTTAT
3121 TTGCGATTTACAAGAAAGAAGAGAAAAATTTGGATCTAGCAAAGAAATTGATATGGCAAT
3181 TGTGACATTAAAAGTCTTTGCGGTAGCAGGACTTTTGAATATGACGGTGTCTACTGCTGC
3241 TGCAGCTGAAAATATGTATTCTCAAATGGGATTAGACACTAGGCCATCTATGAAAGAAGC
3301 AGGTGGAAAAGAGGAAGGCCCTCCACAGGCATATCCTATTCAAACAGTAAATGGAGTACC
3361 ACAATATGTAGCACTTGACCCAAAAATGGTGTCCATTTTCATGGAAAAGGCAAGAGAAGG
3421 ACTAGGAGGGGAGGAAGTTCAACTATGGTTTACTGCCTTCTCTGCAAATTTAACACCTAC
3481 TGACATGGCCACATTAATAATGGCCGCACCAGGGTGCGCTGCAGATAAAGAAATATTGGA
3541 TGAAAGCTTAAAGCAACTGACAGCAGAATATGATCGCACACATCCCCCTGATGCTCCCAG
3601 ACCATTACCCTATTTTACTGCAGCAGAAATTATGGGTATAGGATTAACTCAAGAACAACA
3661 AGCAGAAGCAAGATTTGCACCAGCTAGGATGCAGTGTAGAGCATGGTATCTCGAGGCATT
3721 AGGAAAATTGGCTGCCATAAAAGCTAAGTCTCCTCGAGCTGTGCAGTTAAGACAAGGAGC
3781 TAAGGAAGATTATTCATCCTTTATAGACAGATTGTTTGCCCAAATAGATCAAGAACAAAA
3841 TACAGCTGAAGTTAAGTTATATTTAAAACAGTCATTAAGCATAGCTAATGCTAATGCAGA
3901 CTGTAAAAAGGCAATGAGCCACCTTAAGCCAGAAAGTACCCTAGAAGAAAAGTTGAGAGC
3961 TTGTCAAGAAATAGGCTCACCAGGATATAAAATGCAACTCTTGGCAGAAGCTCTTACAAA
4021 AGTTCAAGTAGTGCAATCAAAAGGATCAGGACCAGTGTGTTTTAATTGTAAAAAACCAGG
4081 ACATCTAGCAAGACAATGTAGAGAAGTGAAAAAATGTAATAAATGTGGAAAACCTGGTCA
4141 TCTAGCTGCCAAATGTTGGCAAGGAAATAGAAAGAATTCGGGAAACTGGAAGGCGGGGCG
4201 AGCTGCAGCCCCAGTGAATCAAATGCAGCAAGCAGTAATGCCATCTGCACCTCCAATGGA
4261 GGAGAAACTATTGGATTTATAAATTATAATAAAGTAGGTACGACTACAACATTAGAAAAG
4321 AGGCCAGAAATACTTATATTTGTAAATGGATATCCTATAAAATTTTTATTAGATACAGGA
4381 GCAGATATAACAATTTTAAATAGGAGAGATTTTCAAGTAAAAAATTCTATAGAAAATGGA
4441 AGGCAAAATATGATTGGAGTAGGAGGAGGAAAGAGAGGAACAAATTATATTAATGTACAT
4501 TTAGAGATTAGAGATGAAAATTATAAGACACAATGTATATTTGGTAATGTTTGTGTCTTA
4561 GAAGATAACTCATTAATACAACCATTATTGGGGAGAGATAATATGATTAAATTCAATATT
4621 AGGTTAGTAATGGCTCAATAATTTTATCCCGGGTTTTATAGCTAATTAGTCATTTTTCG
4681 TAAGTAAGTATTTTTATTTAATACTTTTATTGTACTTATGTTAAAT
```

Predicted nucleotide sequence of vCP329 insertion. The H6 promoter starts at position 2146. The coding sequence for FIV 97TM is from position 2022 to position 42. The I3L promoter starts at position 2253. The FIV gag start codon is at position 2353 and the pol stop codon is at position 3766.

```
   1 TTAATCAATAAAAGAATTCCTGCAGGAATTCATAAAAATCATTCTTCTCCTTCTACTTC
  61 AGGCATTGCAATTACTGTGTATCCTAGTATCTTGTGGATACAATTTCTTATACAATCAAC
 121 CAATGTAGGTAAACATAAAATCAATAATAACACTCCTAATCCTATTCCCAAGATACCTCC
 181 CAATAGTCCCCTTTTCCTTCTAGGTTTATATTCCATGACTTCCTCTGGGACCACTAAGTA
 241 ATCTGGTTGTTTTACAACTTGATACTGTTCTAAGGATTGTCGTAATCCTGCTACTGGGTT
 301 ATACCAATTCCTTAAGATGCCTCGATTGCTAGGACATGCCATTTTAGTACCACTATAACT
 361 ACTACTACTATTTGTACAATTACAATTCATATACCCCCATGACGATGGCAAGTCAGATGT
 421 ACAAGACCAATTTCCAGCAATATTATACATTTCTACAGCTTTTGTCATATTGAAATGCAC
 481 AATAAGGTCATCTACCTTCATAGTAAACCCATTTTGTAAAGAACAATTGTACATTTTATT
 541 TGAATACATGGTACAATCTACAGGATTCGCACCTGAAACATCTCGAGTGTTTCCACATGT
 601 ATCAATGAGCGAGGTATCGGATCCTACATTCCATCTACATCTAATTCTAAACCTTGCTTC
 661 AGAATGATGTTTTGATTTATTTCTATGACATCCAAACTCTATCCAAGCTCCCGTTACTTC
 721 TCCATAATCTCCTGAACTTCTCATTGCAAAGGTTAGGTTTTTGTGCTATTGCACTGTAG
 781 AGATATTTTCACCTTTTTACTTTCCAAATCTGGTCTCCACTCCCATCTATTTCTTTGTTT
 841 CCATGACGAGATTGCTCTACGCCATGATCCAGGCTGACTCTGTGTTCTTTGACAATGAAA
 901 CTTTACCTTTGCCTCTTCCCATTTACAACTGTTATAATAGGCCATTTGATTCCACCATCC
 961 ACATTTTGGTATTTCAGGGTCCTGAATTTGTGAAGTATTCCACATACATGTTTGATTAGG
1021 TCCAAATGTATAATTGATCAGTGGGATTTGTAATGGGTCTGTACAATAGCTTAATTGTTT
1081 TGTAACTTTATTGTACAACATTTTTCCTCCTGTTAGACATAATGATATATTTATTTTCCC
1141 TTGTAACCAAGTATCTACTCTATCTAAATAACACTGATAATCAGGTACTATTACTGAAAC
1201 ATTATAACATGTGTTATTAGCACATCCTGATGGTCCTGTTATAGTCTCATTCCATCTTTT
1261 CCATATTCTGCCTCTTCTACATTGTCTAGTAGCCTTTTTGAATAATGTTGCCCATATTTC
1321 TCTAGTCCAATTCCCCAAGGTAGGTCCCTCTCGTATACTTATATTTGTCTTAGCTTTTAG
1381 ATGTATCATTGCCCCAAGAAAGTCCTGACAGGCGGGTTCTTCTGGTGCCCAACAGTCCCA
1441 AAAAATTATTTCTGATTCTTCTACTGGGACTACTAATGGTGGAAGTCTCCATACTACCTG
1501 AGCGTTGGTTGTCTGTGAATATATTATTAATCCTATAAATAAAATCAGGTACAAAGTCAC
1561 CGTTCCTAGGCAACATCGTCTACCATATTTTATATTGTCAGTTGTACCCTTCTCTCTATT
1621 ATTATAACACTCTTCTTGGGGTGCTTCTATATCAATGTCATGTCTTAAAGATCCTAACTT
1681 ATTTCGATTACCTAAATATATACAATATTCCTATGAACGCATGAACCAGGGACAATACTTG
1741 TTCATCAGAATACCTTAAAAATCTTGCTCTTCTAAACTTACCTGCATTTCCTTCTTCCAG
1801 TTTTACCTCTTGAATTTCGTTCCTTAGATCTTGTAACTTAGGTTGTAATATGTTACAGTA
1861 GTTTTGCTTTTCTTTTTCTGTTATTCCAGGTACCCTAAATGGGTTTACTCCTGGATTTAG
1921 TGGTCCTTCTTCACTCATTTGTGTTGCTATATCAAAATCTAATAACTCTTCAGCTTCTTC
1981 TGGTCCTATCCATTGTCTATTGGCTGCAAATCCTTCTGCCATTACGATACAAACTTAACG
2041 GATATCGCGATAATGAAATAATTTATGATTATTTCTCGCTTTCAATTTAACACAACCCTC
2101 AAGAACCTTTGTATTTATTTTCACTTTTTAAGTATAGAATAAAGAACTGCAGCTAATTAA
2161 TTAAGCTACAAATAGTTTCGTTTTCACCTTGTCTAATAACTAATTAATTAAGGATCCCCC
2221 GTACCGGGCCCCCCCTCGAGGTCGACATCGATACATCATGCAGTGGTTAAACAAAAACAT
2281 TTTTATTCTCAAATGAGATAAAGTGAAAATATATATCATTATATTACAAAGTACAATTAT
2341 TTAGGTTTAATCATGGGGAATGGACAGGGGCGAGATTGGAAAATGGCCATTAAGAGATGT
2401 AGTAATGTTGCTGTAGGAGTAGGGGGAAGAGTAAAAAATTTGGAGAAGGGAATTTCAGA
2461 TGGGCCATTAGAATGGCTAATGTATCTACAGGACGAGAACCTGGTGATATACCAGAGACT
2521 TTAGATCAACTAAGGTTGGTTATTTGCGATTTACAAGAAAGAAGAGAAAAATTTGGATCT
2581 AGCAAAGAAATTGATATGGCAATTGTGACATTAAAAGTCTTTGCGGTAGCAGGACTTTTG
2641 AAATATGACGGTGTCTACTGCTGCTGCAGCTGAAAATATGTATTCTCAAATGGGATTAGAC
2701 ACTAGGCCATCTATGAAGAAGCAGGTGGAAAAGAGGAAGGCCCTCCACAGGCATATCCT
2761 ATTCAAACAGTAAATGGAGTACCACAATATGTAGCACTTGACCCAAAAATGGTGTCCATT
```

FIG. 8A

| FIG. 8 | FIG. 8A |
|---|---|
| | FIG. 8B |

```
2821 TTCATGGAAAAGGCAAGAGAAGGACTAGGAGGGGAGGAAGTTCAACTATGGTTTACTGCC
2881 TTCTCTGCAAATTTAACACCTACTGACATGGCCACATTAATAATGGCCGCACCAGGGTGC
2941 GCTGCAGATAAAGAAATATTGGATGAAAGCTTAAAGCAACTGACAGCAGAATATGATCGC
3001 ACACATCCCCCTGATGCTCCCAGACCATTACCCTATTTTACTGCAGCAGAAATTATGGGT
3061 ATAGGATTAACTCAAGAACAACAAGCAGAAGCAAGATTTGCACCAGCTAGGATGCAGTGT
3121 AGAGCATGGTATCTCGAGGCATTAGGAAAATTGGCTGCCATAAAAGCTAAGTCTCCTCGA
3181 GCTGTGCAGTTAAGACAAGGAGCTAAGGAAGATTATTCATCCTTTATAGACAGATTGTTT
3241 GCCCAAATAGATCAAGAACAAAATACAGCTGAAGTTAAGTTATATTTAAAACAGTCATTA
3301 AGCATAGCTAATGCTAATGCAGACTGTAAAAAGGCAATGAGCCACCTTAAGCCAGAAAGT
3361 ACCCTAGAAGAAAGTTGAGAGCTTGTCAAGAAATAGGCTCACCAGGATATAAAATGCAA
3421 CTCTTGGCAGAAGCTCTTACAAAAGTTCAAGTAGTGCAATCAAAAGGATCAGGACCAGTG
3481 TGTTTTAATTGTAAAAAACCAGGACATCTAGCAAGACAATGTAGAGAAGTGAAAAAATGT
3541 AATAAATGTGGAAAACCTGGTCATCTAGCTGCCAAATGTTGGCAAGGAAATAGAAAGAAT
3601 TCGGGAAACTGGAAGGCGGGCGAGCTGCAGCCCCAGTGAATCAAATGCAGCAAGCAGTA
3661 ATGCCATCTGCACCTCCAATGGAGGAGAAACTATTGGATTTATAAATTATAATAAAGTAG
3721 GTACGACTACAACATTAGAAAAGAGGCCAGAAATACTTATATTTGTAAATGGATATCCTA
3781 TAAAATTTTTATTAGATACAGGAGCAGATATAACAATTTTAAATAGGAGAGATTTTCAAG
3841 TAAAAAATTCTATAGAAATGGAAGGCAAAATATGATTGGAGTAGGAGGAGGAAAGAGAG
3901 GAACAAATTATATTAATGTACATTTAGAGATTAGAGATGAAAATTATAAGACACAATGTA
3961 TATTTGGTAATGTTTGTGTCTTAGAAGATAACTCATTAATACAACCATTATTGGGGAGAG
4021 ATAATATGATTAAATTCAATATTAGGTTAGTAATGGCTCAATAATTTTATCCCGGGTTTT
4081 TATAGCTAATTAGTCATTTTTCGTAAGTAAGTATTTTTATTTAATACTTTTTATTGTACT
4141 TATGTTAAAT
```

| FIG. 8B | FIG. 8 | FIG. 8A |
|---|---|---|
|  |  | FIG. 8B |

ALVAC/FIV CONSTRUCTS

STATEMENT OF POSSIBLE GOVERNMENT RIGHTS

Some work reported herein may have been supported by a NIH/NIAID grant (R01-AI30904) and a Virogenetics Corp./University of Florida collaborative grant. The government may have certain rights (without prejudice or admission).

RELATED APPLICATIONS

Reference is made to U.S. application Ser. No. 08/417,210 filed Apr. 5, 1995 as a continuation-in-part of application Ser. No. 08/223,842, filed Apr. 6, 1994 which in turn is a continuation-in-part of application Ser. No. 07/897,382, filed Jun. 11, 1992 (now U.S. application Ser. No. 8/303,275, filed Sep. 7, 1994), which in turn is a continuation-in-part of application Ser. No. 07/715,921, filed Jun. 14, 1991. Application Ser. No. 08/417,210 is also a continuation-in-part of application Ser. No. 08/105,483, filed Aug. 13, 1993, now U.S. Pat. No. 5,494,807, which in turn is a continuation of application Ser. No. 07/847,951, filed Mar. 6, 1992, which in turn is a continuation-in-part of application Ser. No. 07/713,967, filed Jun. 11, 1991, which in turn is a continuation in part of application Ser. No. 07/666,056, filed Mar. 7, 1991 (now U.S. Pat. No. 5,364,773). Mention is also made of co-pending allowed application Ser. No. 08/184,009, filed Jan. 19, 1994 as a continuation-in-part of application Ser. No. 08/007,115, filed Jan. 20, 1993. Each of the aforementioned and above-referenced applications and patent(s) are hereby incorporated herein by reference.

FIELD OF THE INVENTION

The present invention relates: to certain product(s) from lentivirus, retrovirus and/or immunodeficiency virus, e.g., HIV, SIV, EIAV, BIV, FIV, comprising certain epitope(s) of interest, preferably Env, Gag, Pol, and accessory gene products, e.g. Tat, Rev, more preferably of Gag and Pol or Env, Gag and Pol and most preferably Gag and protease; to certain nucleic acid molecule(s), e.g., RNA, DNA, encoding the product(s); to a vector, preferably a mammalian vector system, comprising the nucleic acid molecule(s) and preferably expressing the product(s) as exogenous to the vector; to the product(s) obtained or obtainable from expression by the vector; to immunological, immunogenic and/or vaccine compositions comprising the vector and/or the product(s); to methods for preparing the product(s); to methods for preparing the vector; to methods for preparing the compositions; and to methods for using the product(s), vector and compositions, including methods for obtaining an immunological response such as by immunization regimens wherein the product(s), vector and/or compositions are administered alone or in a prime/boost configuration with inactivated lentivirus, retrovirus or recombinant subunit preparations, e.g., in a prime/boost configuration with an inactivated infected cell vaccine or immunological or immunogenic composition (ICV).

The invention especially relates to recombinant immunological, immunogenic or vaccine compositions and their utility in stimulating a response, such as providing protection against a lentivirus challenge exposure, including exposure to a heterologous strain. The recombinant composition is preferably comprised of a mammalian vector system expressing lentivirus gene products used in effective immunization regimens alone or in a prime/boost configuration with inactivated lentivirus preparations (e.g., ICV) or recombinant subunit preparations.

Several documents are referenced in this application. Full citation to these documents is found at the end of the specification immediately preceding the claims or where the document is mentioned; and each of these documents is hereby incorporated herein by reference.

BACKGROUND OF THE INVENTION

The patent and scientific literature includes various mammalian vector systems such as mammalian virus-based vector systems and mammalian DNA-based vector systems, and how to make and use these vector systems, for instance for cloning of exogenous DNA and expression of proteins, as well as uses for such proteins and uses for products from such proteins.

For instance, recombinant poxvirus (e.g., vaccinia, avipox virus) and exogenous DNA for expression in this viral vector system can be found in U.S. Pat. Nos. 4,603,112, 4,769,330, 5,174,993, 5,505,941, 5,338,683, 5,494,807, 5,503,834, 4,722,848, 5,514,375, U.K. Patent GB 2 269 820 B, WO 92/22641, WO 93/03145, WO 94/16716, PCT/US94/06652, and allowed U.S. application Ser. No. 08/184,009, filed Jan. 19, 1994. See generally Paoletti, "Applications of pox virus vectors to vaccination: An update," PNAS USA 93:11349–11353, October 1996; Moss, "Genetically engineered poxviruses for recombinant gene expression, vaccination, and safety," PNAS USA 93:11341–11348, October 1996.

Baculovirus expression systems and exogenous DNA for expression therein, and purification of recombinant proteins therefrom can be found in Richardson, C. D. (Editor), *Methods in Molecular Biology* 39, "Baculovirus Expression Protocols" (1995 Humana Press Inc.) (see, e.g., Ch.18 for influenza HA expression, Ch.19 for recombinant protein purification techniques), Smith et al., "Production of Huma Beta Interferon in Insect Cells Infected with a Baculovirus Expression Vector," Molecular and Cellular Biology, December, 1983, Vol. 3, No. 12, p. 2156–2165; Pennock et al., "Strong and Regulated Expression of *Escherichia coli* B-Galactosidase in Infect Cells with a Baculovirus vector," Molecular and Cellular Biology March 1984, Vol. 4, No. 3, p. 399–406; EPA 0 370 573 (Skin test and test kit for AIDS, discussing baculovirus expression systems containing portion of HIV-1 env gene, and citing U.S. application Ser. No. 920,197, filed Oct. 16, 1986 and EP Patent publication No. 265785).

U.S. Pat. No. 4,769,331 relates to herpesvirus as a vector. See also Roizman, "The function of herpes simplex virus genes: A primer for genetic engineering of novel vectors," PNAS USA 93:11307–11312, October 1996; Andreansky et al., "The application of genetically engineered herpes simplex viruses to the treatment of experimental brain tumors," PNAS USA 93:11313–11318, October 1996. Epstein-Barr virus vectors are also known. See Robertson et al. "Epstein-Barr virus vectors for gene delivery to B lymphocytes," PNAS USA 93:11334–11340, October 1996. Further, there are alphavirus-based vector systems. See generally Frolov et al., "Alphavirus-based expression vectors: Strategies and applications," PNAS USA 93:11371–11377, October 1996.

There are also poliovirus and adenovirus vector systems (see, e.g., Kitson et al., J. Virol. 65, 3068–3075, 1991; Grunhaus et al., 1992, "Adenovirus as cloning vectors," Seminars in Virology (Vol. 3) p. 237–52, 1993; Ballay et al.

EMBO Journal, vol. 4, p. 3861–65; Graham, Tibtech 8, 85–87, April, 1990; Prevec et al., J. Gen Virol. 70, 429–434). See also U.S. application Ser. Nos. 08/675,556 and 08/675,566, filed Jul. 3, 1996 (adenovirus vector system, preferably CAV2) and PCT WO91/11525 (CAV2 modified to contain a promoter-gene sequence within the region from the SmaI site close to the end of the inverted terminal repeat region up to the promoter for the early region 4 (E4)).

There are also DNA vector systems. As to transfecting cells with plasmid DNA for expression therefrom, reference is made to Felgner et al. (1994), J. Biol. Chem. 269, 2550–2561. As to direct injection of plasmid DNA as a simple and effective method of vaccination against a variety of infectious diseases reference is made to Science, 259: 1745–49, 1993. See also McClements et al., "Immunization with DNA vaccines encoding glycoprotein D or glycoprotein B, alone or in combination, induces protective immunity in animal models of herpes simplex virus-2 disease," PNAS USA 93:11414–11420, October 1996.

In 1983, human immunodeficiency virus type 1 (HIV1) was identified as the causative agent of AIDS and was subsequently classified into the lentivirus subfamily of the retrovirus family (Hardy, 1990). Other members of the lentivirus subfamily are equine infectious anemia virus (EIAV), feline immunodeficiency virus (FIV), bovine immunodeficiency virus (BIV), Simian immunodeficiency virus (SIV) and HIV-2. Much attention within the field of medical virology has been focused on the AIDS pandemic caused by infection with HIV. This lentivirus system has been scrutinized with respect to its molecular biology, immunobiology and pathogenesis in an effort to develop safe and effective vaccines and antiviral therapies. To date, HIV, as well as other lentiviral vaccine studies using different vaccine types have encountered varying degrees of success (Heeney et al., 1994; Daniel et al., 1992; Fultz et al., 1992; Girard et al., 1991; Issel et al., 1992). Further, knowledge is still lacking on the relevance of specific HIV immune responses on vaccine efficacy in humans. Thus, after many years, despite a massive, worldwide effort, an effective HIV1 vaccine is still not available.

Infection of cats with feline immunodeficiency virus (FIV) causes persistent infection and AIDS-like immunosuppressive diseases similar to the HIV infection. As such, FIV infection of cats provides a model for investigating lentivirus immunopathogenicity and vaccine development (Pedersen et al., 1987; Johnson et al., 1994). Similar to HIV, heterogeneity exists, such that multiple FIV subtypes exist (Sadora et al., 1994; Okada et al., 1994). Indeed, like HIV, FIV strains have been classified into four subtypes (A-D) based on genetic differences predominantly in the env and, to a lesser extent gag coding regions.

Thus, while inactivated whole FIV vaccines and inactivated FIV-infected cell vaccines (ICV) have obtained protection against homologous and slightly heterologous FIV (Hosie et al., 1995; Johnson et al., 1994; Yamamoto et al., 1991, 1993), these same vaccines failed to induce protective immunity against distinctly heterologous FIV strains of other subtypes such that induction of protective immunity against a broad range of FIV subtypes may call for a modified or different vaccine approach. This obviously raises concerns relevant to vaccine development. It must also be noted that the FIV prevalence in the cat population is greater than HIV is in man (Verschoor et al., 1996). The development of an FIV vaccine or immunogenic composition is not only useful in providing a model for an HIV vaccine or immunogenic composition but is also therefore of importance from a veterinary health perspective.

More particularly, from the previous FIV studies (Hosie et al., 1995; Johnson et al., 1994; Yamamoto et al., 1991, 1993) it was observed that only cats with significant FIV Env-specific serum reactivity were likely to be protected against homologous challenge exposure. In no case were vaccine-administered animals lacking such a response observed to be protected against FIV challenge (Johnson et al., 1994; Yamamoto et al., 1991, 1993). Together, these results coupled to the observations, to date, that subunit immunogens have not been shown to elicit a protective immune response in target species bring to the forefront several important points relevant to the state-of-the-art for FIV and lentivirus, vaccine development in general. One exception perhaps is with the simian immunodeficiency virus (SIV)/macaque system where certain recombinant subunit preparations (including vaccinia-based recombinants) or combinations of these recombinant subunits have conferred, at least, partial protection from SIV challenge exposure (Hu, 1992; 1994; 1995). This data is somewhat limited in scope since complete protection from infection was not observed and challenge studies were not performed with a distinctly heterologous SIV strain. Moreover, no level of protection was afforded by recombinant subunits devoid of an SIV Env component (Hu et al., 1994).

Relevant to FIV vaccine development, no sub-unit based vaccine candidate has been taught or suggested; there is no teaching as to how to develop a subunit vaccine; and, it is not obvious as to how to develop a subunit-based vaccine candidate.

Secondly, a different or perhaps modified approach, as compared to the inactivated conventional vaccines, needs to be developed to afford protection against heterologous strains (Hosie et al., 1995; Johnson et al., 1994).

Lastly, Env-specific immune responses in protective immunity may be important (Johnson et al., 1994; Yamamoto et al., 1991, 1993). Indeed, in Flynn et al., "ENV-specific CTL Predominate in Cats Protected from Feline Immunodeficiency Virus Infection by Vaccination," *The Journal of Immunology*, 1996, 157:3658–3665, at 3664 the authors conclude "that FIV Env-specific CTL may be more effective in protective immunity to FIV infection of domestic cats" such that "future vaccine strategies should be aimed at eliciting both humoral and cell-mediated immune responses that are long-lived, recognize appropriate epitopes on the viral envelope glycoprotein, and are targeted to tissues known to sequester virus."

It can thus be appreciated that provision of a feline immunodeficiency virus recombinant subunit immunogenic, immunological or vaccine composition which induces an immunological response against feline immunodeficiency virus infections when administered to a host, e.g., a composition having enhanced safety such as NYVAC- or ALVAC-based recombinants containing exogenous DNA coding for an FIV epitope of interest, such as of FIV Env, Gag, or Pol, especially in an immunogenic configuration, or any combination thereof, for instance, FIV Gag-protease, Gag-Pol, or Gag and a portion of Pol (such as a portion of Pol including protease) or all of Env, Gag and Pol or a portion of Pol, in combination, would be a highly desirable advance over the current state of technology. Further, use of such recombinants or compositions containing such recombinants in a prime-boost regimen, e.g., wherein the recombinant composition is used in an initial immunization and a subsequent immunization is with an inactivated FIV, or ICV, or other recombinant subunit preparation would be a highly desirable advance over the current state of technology.

And more generally, it can thus be appreciated that provision of a lentivirus, retrovirus or immunodeficiency virus recombinant subunit immunogenic, immunological or vaccine composition which induces an immunological response against the lentivirus, retrovirus or immunodeficiency virus infections when administered to a host, e.g., a composition having enhanced safety such as NYVAC- or ALVAC-based recombinants containing exogenous DNA coding for a lentivirus, retrovirus, or immunodeficiency virus epitope of interest, such as Env, Gag, or Pol, especially in an immunogenic configuration, or any combination thereof, for instance, Gag-protease, Gag-Pol or Gag and a portion of Pol (such as a portion including protease) all of Env, Gag and Pol or a portion of Pol, in combination such as Env, Gag-protease, in combination, would be a highly desirable advance over the current state of technology. Further, use of such recombinants or compositions containing such recombinants in a prime-boost regimen, e.g., wherein the recombinant composition is used in an initial immunization and a subsequent immunization is with an inactivated lentivirus, retrovirus or immunodeficiency virus, or ICV, or other recombinant subunit preparation, such as a respective inactivated virus, ICV or other recombinant subunit preparation would be a highly desirable advance over the current state of technology (As to "respective", if the recombinant is, for example an FIV recombinant, inactivated FIV or an FIV ICV preparation may be "respective").

OBJECTS AND SUMMARY OF THE INVENTION

It is therefore an object of the invention to provide certain product(s) from lentivirus, retrovirus and/or immunodeficiency virus, e.g., HIV, SIV, EIAV, BIV, FIV, Visna virus, carpine arthritis-encephalitis virus, comprising certain epitope(s) of interest, preferably Env, Gag, Pol or epitopes thereon, with optional accessory functions or proteins or epitope(s) of interest thereon e.g. Tat and/or Rev, more preferably Gag and Pol, or Env, Gag and Pol, or Gag and a portion of Pol, or Env, Gag and a portion of Pol, especially such a portion including protease, and most preferably Gag and protease, or Env, Gag and protease, or epitopes thereon, with optional accessory functions or proteins, e.g., Tat and/or Rev or other such functions/proteins, or epitopes thereon. Other accessory functions or proteins which can be included in the product(s) or epitope(s) of interest include any or all of net, vpu, vit, vpr, and vpx or epitope(s) thereon, inter alia; see Trono, D., Cell, 82:189–192, Jul. 28, 1995. Such accessory functions or proteins may be considered non-envelope functions or proteins which can be included in the product(s) or epitope(s) of interest, e.g. for induction of a cellular response. For instance, for a given lentivirus, retrovirus or immunodeficiency virus pathogen, that pathogen's accessory function(s) or protein(s) or epitope(s) thereon can be included; for example, the product(s) could thus include Gag-Pro plus accessory function(s) or protein(s) or epitope(s) thereon.

It is an additional object of the invention to provide certain nucleic acid molecule(s), e.g., RNA, DNA, encoding the product(s), e.g., encoding certain epitope(s) of interest such as Gag and protease or all of Env, Gag and Pol.

It is a further object of the invention to provide a vector, preferably a mammalian vector system, comprising the nucleic acid molecule(s) and preferably expressing the product(s) as exogenous to the vector, e.g., a poxvirus, baculovirus, herpesvirus, Epstein-Barr, alphavirus, poliovirus, adenovirus or DNA vector system.

It is a further object of the invention to provide the product(s) obtained or obtainable from expression by the vector.

It is yet a further object of the invention to provide an immunological, immunogenic and/or vaccine composition comprising the vector and/or the product(s).

It is still another object of the invention to provide methods for preparing the product(s).

It is yet another object of the invention to provide methods for preparing the vector.

It is even still a further object of the invention to provide methods for preparing the compositions.

And it is a further object of the invention to provide methods for using the product(s), vector and compositions, including methods for obtaining an immunological response such as by immunization regimens wherein the product(s), vector and/or compositions are administered alone or in a prime/boost configuration with inactivated lentivirus, retrovirus or recombinant subunit preparations, e.g., in a prime/boost configuration with an inactivated infected cell vaccine or immunological or immunogenic composition (ICV), such as a respective ICV.

The present invention thus relates to recombinant immunological, immunogenic or vaccine compositions and their utility in eliciting a response such as by providing protection against lentivirus, retrovirus or immunodeficiency virus challenge exposure in a target species.

More in particular, the invention relates to a mammalian vector system for the insertion and expression of foreign genes for use as safe immunization vehicles to elicit a response such as a protective immune response against lentiviruses, retroviruses or immunodeficiency viruses.

In accord with the herein objects, the invention accordingly relates to a mammalian vector system, which expresses gene products (e.g., a gene product including an epitope of interest) of a lentivirus, retrovirus or immunodeficiency virus such EIAV, FIV, BIV, HIV, or SIV, with feline immunodeficiency virus (FIV) presently preferred; and, the invention relates to immunogenic and/or immunological and/or vaccine compositions which induce an immunological and/or protective response against a lentivirus, retrovirus or immunodeficiency virus such EIAV, FIV, BIV, HIV, or SIV exposure when administered to the target host, e.g., FIV and a feline, such as a domesticated cat or kitten.

In one aspect, in furthermore of the herein objects, the present invention comprises a mammalian vector (e.g., poxvirus, baculovirus, herpesvirus, Epstein-Barr, alphavirus, poliovirus, adenovirus or DNA vector system, preferably a poxvirus) expressing a lentivirus, retrovirus or immunodeficiency virus epitope of interest, e.g., EIAV, FIV, BIV, HIV, or SIV, preferably FIV; and, the epitope of interest is preferably Gag/protease. The vector is useful in the protection of the target species (e.g., feline) against a highly homologous challenge exposure; and accordingly, the invention encompasses an immunological, immunogenic or vaccine composition comprising the vector and optionally an acceptable carrier or diluent.

In another aspect, in accordance with the herein objects, the present invention comprises a method for inducing an immunological response, preferably a protective response comprising administering the vector or composition comprising the vector to a host. The method can be an immunizing regimen, e.g., priming with the vector or composition comprising the vector (and expressing the lentivirus, retrovirus or immunodeficiency virus (e.g., FIV) epitope(s) of interest gene products) and boosting with a respective lentivirus, retrovirus or immunodeficiency subunit preparation (e.g., FIV inactivated whole cell (ICV) preparation) or with a respective lentivirus, retrovirus or immunodeficiency recombinant subunit preparation (e.g., FIV epitope(s) of interest from isolating such from expression of a recombinant containing exogenous nucleic acid molecule(s) encoding the same) to elicit an immunological response such as conferring protection to the host (e.g., cats) against homologous and heterologous lentivirus, retrovirus or immunodeficiency virus isolates.

It is an additional object of this invention to provide a recombinant poxvirus antigenic, vaccine or immunological composition having an increased level of safety compared to known recombinant poxvirus vaccines.

It is a further object of this invention to provide a modified vector for expressing a gene product in a host, wherein the vector is modified so that it has attenuated virulence in the host.

It is another object of this invention to provide a Method for expressing a gene product in a cell cultured in vitro using a modified recombinant virus or modified vector having an increased level of safety.

These and other objects and advantages of the present invention will become more readily apparent after consideration of the following.

In a further aspect, the present invention relates to a vector, preferably a modified recombinant virus having inactivated virus-encoded genetic functions so that the recombinant virus has attenuated virulence and enhanced safety. The functions can be non-essential, or associated with virulence (e.g., essential). The virus is advantageously a poxvirus, particularly a vaccinia virus or an avipox virus, such as fowlpox virus and canarypox virus. The vector which is preferably a modified recombinant virus can include, within an essential or nonessential region of the virus genome, a heterologous DNA sequence which encodes an antigen or epitope derived from a lentivirus, retrovirus or immunodeficiency virus, e.g., EIAV, FIV, BIV, HIV, or SIV, preferably feline immunodeficiency virus, such as, e.g., Env, Gag, Pol, accessory functions (e.g. Tat, Rev), or any combination thereof, such as Gag-Pol or Env, Gag, and Pol or Gag and a portion of Pol or Env, Gag and a portion of Pol, such as a portion of Pol including protease, or Gag-protease or Env, Gag, and protease.

In another aspect, the present invention relates to an antigenic, immunological, immunogenic or vaccine composition or a therapeutic composition for inducing an antigenic or immunological or protective response in a host animal such as a feline, e.g., domesticated cat or kitten, inoculated with the composition, the composition can include a carrier and an inventive vector which is preferably a modified recombinant virus having inactivated nonessential virus-encoded genetic functions so that the recombinant virus has attenuated virulence and enhanced safety; or the expression product of such a vector or modified recombinant virus. The virus used in the composition (or for expressing a product for use in a composition) according to the present invention is advantageously a poxvirus, particularly a vaccinia virus or an avipox virus, such as fowlpox virus and canarypox virus. The modified recombinant virus can include, within an essential or nonessential region of the virus genome, a heterologous DNA sequence which encodes an antigenic protein, e.g., an epitope of interest derived from a lentivirus, retrovirus or immunodeficiency virus, e.g., EIAV, FIV, BIV, HIV, or SIV, preferably feline immunodeficiency virus, such as an antigen, e.g., Env, Gag, protease, or any combination thereof, such as Gag-protease or Env, Gag, and protease.

In yet another aspect, the present invention relates to a method for inducing an antigenic, immunological, immunogenic, vaccine (protective), and/or therapeutic response in a host animal such as a feline, e.g., domesticated cat or kitten, for instance, a host animal in need of such a response, comprising administering an amount of the aforementioned inventive composition effective to obtain the response, either alone or as part of a prime-boost regimen (e.g., administering the inventive composition or administering either or both of an inactivated lentivirus, retrovirus or immunodeficiency virus or ICV or IWV either before or after administering the inventive composition).

In a further aspect, the present invention relates to a method for expressing a gene product in a cell in vitro by introducing into the cell an inventive vector, such as a modified recombinant virus having attenuated virulence and enhanced safety. The vector or modified recombinant virus can include, within a nonessential or essential region of the virus genome, a heterologous DNA sequence which encodes an epitope of interest such as an antigenic protein, e.g. derived from a retrovirus, lentivirus or immunodeficiency virus, e.g., EIAV, FIV, BIV, HIV, or SIV, preferably feline immunodeficiency virus, such as, e.g., Env, Gag, Pol, accessory functions (e.g. Tat, Rev), or any combination thereof, such as Gag-Pol, or Env, Gag and Pol, or Gag and a portion of Pol or Env, Gag or a portion of Pol wherein the portion can include protease, or Gag-protease or Env, Gag, protease. The gene product can be harvested from the cells, or the cells can then be reinfused directly into an animal or used to amplify specific reactivities for reinfusion (Ex vivo therapy).

Thus, in a specific further aspect, the present invention relates to a method for expressing a gene product in a cell cultured in vitro by introducing into the cell a vector or preferably a modified recombinant virus having attenuated virulence and enhanced safety. The vector or modified recombinant virus can include, within an essential or nonessential region of the virus genome, a heterologous DNA sequence which encodes an epitope of interest or an antigenic protein, e.g., derived from a lentivirus, retrovirus, or immunodeficiency virus, e.g., EIAV, FIV, BIV, HIV, or SIV, preferably feline immunodeficiency virus, such, e.g., Env, Gag, Pol, accessory functions (e.g. Tat, Rev), or any combination thereof, such as Gag-Pol, or Env, Gag and Pol, or Gag and a portion of Pol, or Env, Gag and a portion of Pol, wherein the portion can include a protease, or Gag-protease or Env, Gag, protease. The product can then be administered to a host to stimulate a response.

Antibodies can be raised by compositions including the inventive vectors or recombinants or expression products of the inventive vectors or recombinants. The antibodies raised can be useful in a host for the prevention or treatment of a lentivirus, retrovirus or immunodeficiency virus such as feline immunodeficiency virus. The antibodies or the expression products of the inventive vectors or recombinants can be used in diagnostic kits, assays or tests to determine the presence or absence in a sample such as sera of lentivirus, retrovirus or immunodeficiency virus, e.g., feline immunodeficiency virus, or antigens thereof or antibodies thereto or of recombinants of the present invention. Accordingly, an aspect of the invention involve the antibodies, diagnostic kits, assays, or tests.

In a still further aspect, the present invention relates to a modified recombinant virus having nonessential or essential virus-encoded genetic functions inactivated therein so that the virus has attenuated virulence, and wherein the modified recombinant virus further contains DNA from a heterologous source in an essential or nonessential region of the virus genome. The DNA can code for an antigen or epitope of interest of a lentivirus, retrovirus or immunodeficiency virus, e.g., EIAV, FIV, BIV, HIV, or SIV, preferably feline immunodeficiency virus, e.g., Env, Gag, Pol, accessory functions, or any combination thereof, such as Gag-Pol or Env, Gag and Pol, or Gag and a portion of Pol or Env, Gag and a portion of Pol, wherein the portion of Pol can include protease, or Gag-protease or Env, Gag, protease. In particular, the genetic functions are inactivated by deleting or disrupting an open reading frame encoding a virulence factor, e.g., an essential region, or by utilizing naturally host restricted viruses, especially naturally host restricted viruses displaying attenuated virulence from having been serial passages and/or plaque purification (with or without subsequent passages). The virus used according to the present invention is advantageously a poxvirus, particularly a vaccinia virus or an avipox virus, such as fowlpox virus and canarypox virus.

Advantageously, the open reading frame is selected from the group consisting of J2R, B13R+B14R, A26L, A56R, C7L-K1L, and I4L (by the terminology reported in Goebel et al., 1990a,b); any combination thereof and, preferably the combination thereof. In this respect, the open reading frame comprises a thymidine kinase gene, a hemorrhagic region, an A type inclusion body region, a hemagglutinin gene, a host range gene region or a large subunit, ribonucleotide reductase; or, any combination thereof and preferably the combination thereof. The modified Copenhagen strain of vaccinia virus is identified as NYVAC (Tartaglia et al., 1992). NYVAC and NYVAC variations have essential regions deleted or disrupted therein, and for a subsequent publication to Tartaglia et al., 1992 which like Tartaglia et al., 1992 relates to deletion of essential regions of vaccinia virus (and therefore relates to NYVAC, NYVAC variations, or viruses taught by or obvious from viruses of Tartaglia et al., 1992 such as NYVAC and NYVAC variations) e.g., NYVAC.1, NYVAC.2, reference is made to PCT WO 95/30018. With respect to NYVAC and NYVAC variations, reference is also made to U.S. Pat. Nos. 5,364,773 and 5,494,807. However, other vaccinia virus strains, such as the COPAK strain, can also be used in the practice of the invention.

In another preferred embodiment the vector is an attenuated canarypox virus, such as a canarypox virus which is not a mixed population. For instance, a Rentschler vaccine strain which was attenuated through more than 200 serial passages on chick embryo fibroblasts, a master seed therefrom was subjected to four successive plaque purifications under agar, from which a plaque clone was amplified through five additional passages. Such a canarypox is called ALVAC.

Results of restriction digests of plaque derived from Kanapox is as follows: Genomic DNA isolated from plaque isolates number 1, 4, and 5 cloned from canarypox virus (Kanapox). DNA from these plaques and from the uncloned canarypox virus was digested with restriction enzymes HindIII, BamHI and EcoRI and run on a 0.8% agarose gel. The gel was stained with ethidium bromide and photographed under UV light (see FIG. 1). The lanes are labeled v=uncloned canarypox virus, 1=plaque 1, 4=plaque 4, and 5=plaque 4. A 1 kb molecule weight marker was run on the far left lane. The restriction profiles show distinct differences between the various plaque isolates. Plaque 1 was chosen as ALVAC ($CP_{pp}$).

In the restriction patterns of the uncloned canarypox virus (lanes=v) several submolar bands can be observed. However, when plaqued cloned, these submolar bands (lanes labeled 1, 4 and 5) become molar species in at least some of the plaque-cloned isolates. This indicates that the uncloned canarypox virus (Kanapox) represents a mixture of genomic variants which differ in restriction profiles.

Thus, ALVAC is different from, has unique properties over, and is superior to Kanapox; and therefore, ALVAC is a preferred vector in the practice of the invention. In particular, the Rentschler strain canarypox virus (Kanapox), from restriction analyses, represents a mixture of viral variants; that is, Kanapox, from which ALVAC was derived, was a mixed population. It is not unprecedented for a vaccine preparation, such as Kanapox, to contain multiple variants. ALVAC is not a mixed population. As such, ALVAC has several unique properties which are not shared by Kanapox, for instance:

ALVAC has a uniform genetic background. This property provides ALVAC with consistency; a unique feature of being useful for preparing vector-based vaccines. Consistency is useful for quality control and regulatory considerations. This property of consistency of ALVAC provides ALVAC with the ability to pass quality control and regulatory considerations, i.e., be useful in the development of vector-based vaccines with predicted genetic properties.

Biological consistency is controlled using ALVAC to derive recombinants. Kanapox does not provide biological consistency. Indeed, Kanapox cannot consistently provide an effective recombinant product. Biological consistency and a consistently effective recombinant product are useful; for instance, for a consistent biological profile with respect to virulence, with regard to virus/host interactions, and ultimately for use as an immunization vehicle. ALVAC achieves biological consistency and consistently effective recombinant products. When Kanapox is used in deriving recombinants, there is no control over the virus background into which the foreign gene is inserted; and therefore, the properties of the resultant recombinant remain in question (cf. studies with vaccinia virus which illustrate that not all vaccinia genetic backgrounds are equivalent as immunization vehicles). ALVAC provides certainty with respect to its virus background, its properties related to virulence, and its functioning as an immunization vehicle.

Although the present invention has primarily been described using a canarypox virus (ALVAC)-based vector, it should be understood that invention herein also resides in the expression of specific lentivirus, retrovirus or immunodeficiency virus gene products and their utility for conferring an immune response such as a protective immune response. Hence, the invention also relates to alternative mammalian vector systems. Examples of such vector systems include other poxviruses, adenoviruses, herpesviruses, alphavirus-based systems, bacterial expression systems, and DNA-based immunogen formulations.

Although the present invention has primarily been described using the lentivirus FIV, it should be understood that invention herein also resides in the expression of functional homologs of the FIV gene products from other lentivirus and retrovirus and immunodeficiency virus systems, e.g., Env, Gag/protease (i.e., Env, Gag and Pol or a portion of Pol, or Gag and Pol or a portion of Pol wherein the portion of Pol can include protease (without Env), or Env, Gag, protease or Gag-protease (without Env) or Env, Gag, Pol or a portion of Pol and accessory functions (e.g. Tat, Rev) or Gag, Pol or a portion of Pol wherein the portion of Pol can include protease and accessory functions (without Env) or Env, Gag protease and accessory functions or Gag-protease and accessory functions (without Env), of EIAV, FIV, BIV, HIV, or SIV, inter alia). Hence, the invention relates to other lentivirus systems including human immunodeficiency virus-1, -2 (HIV-1,-2), bovine immunodeficiency virus (BIV), equine infectious anemia virus (EIAV), as well as other mammalian lentiviruses.

These and other embodiments are disclosed or are obvious from and encompassed by the following detailed description.

Deposits

The following have been deposited with the American Type Culture Collection ("ATCC"), located at 12301 Parklawn Drive, Rockville, Md., 20852, under the terms of the Budapest Treaty.

| Material | Accession Number | Deposit Date |
| --- | --- | --- |
| ALVAC | VR2547 | NOV. 14, 1996 |
| Plasmid MM 138 (pMM138) (containing FIV env, gag/pro) | 97795 | NOV. 14, 1996 |
| Plasmid MM 129 (pMM129) (containing FIV gag/pro) | 97796 | NOV. 14, 1996 |

The invention thus comprehends nucleic acid molecules, including encoding product(s) having sequences as in the Deposited Material, as well as nucleic acid molecules having substantial homology thereto (e.g., at least 85% homology).

BRIEF DESCRIPTION OF THE DRAWINGS

The following detailed description, given by way of example, but not intended to limit the invention solely to the specific embodiments described, may best be understood in conjunction with the accompanying drawings, incorporated herein by reference, in which:

FIG. 2 shows the nucleotide sequence of FIV env from Rhone Merieux (SEQ ID NO:1) (The FIV env start codon is at position 1 and the stop codon is at position 2569. Plasmid ptg6184, containing the FIV env coding sequence, was from Rhone Merieux(Lyon, France). The FIV env coding sequence in ptg6184 was sequenced and the following differences with the sequence below were observed: position 1218 T is G in ptg6184 changing phe to leu; position 1220 G to A changes gly to glu; and position 2201 C to A change ala to glu);

FIG. 3 shows the nucleotide sequence of FIV gag/pol coding sequences from Rhone Merieux (SEQ ID NO:2) (The gag start codon is at position 1 and the gag stop codon is at position 1414. The ribosomal frameshift site is near position 1255. The frameshift is −1 in relation to the gag open reading frame. The frameshift goes into the pol open reading frame. The pol stop codon is at position 4614. Plasmid ptg8133 from Rhone Merieux contains the FIV gag/pol coding sequences. Part of ptg8133 has been sequenced and the CG at positions 577–578 below is GC in ptg8133, changing the codon from arg to ala);

FIG. 4 shows the ALVAC-nucleotide sequence comprised in the C6 donor plasmid pC6L (SEQ ID NO:3) (Plasmid pC6L contains the C6 insertion sites SmaI (position 409) and EcoRI (position 425));

FIG. 5 shows the predicted nucleotide sequence of the vCP242 insertion (SEQ ID NO:4) (The H6 promoter starts at position 55. The FIV env start codon is at position 179, and the FIV env stop codon is at position 2749). Positions 1 through 54 and positions 2750 through 2879 flank the H6/FIV env expression cassette);

FIG. 6 shows the predicted nucleotide sequence of I3L promoted FIV gag/protease expression cassette and flanking regions in vCP253 (SEQ ID NO:5) (The I3L promoter begins at position 135. The gag start codon is at position 235 and the protease stop codon is at position 1648);

FIG. 7 shows the predicted nucleotide sequence of the H6 promoted FIV env/I3L promoted FIV gag/protease expression cassette and flanking regions in vCP255 (SEQ ID NO:6) (The H6 promotor starts at position 129, the FIV env start codon is at position 253, and the FIV env stop codon is at position 2823. The I3L promotor starts at position 2830, the FIV gag start codon is at position 2930 and the FIV gag stop codon is at position 4282. The ribosomal frameshift site is near position 4184. The frameshift is −1 in relation to the gag open reading frame. The frameshift goes into the pol open reading frame. The stop codon for the protease gene is at position 4641. Positions 1 through 128 and positions 4642 through 4.727 flank the $H_6$FIV env/I3L FIV gag/protease expression cassette); and FIG. 8 shows the predicted nucleotide sequence of vCP329 insertion (SEQ ID NO:7) (The H6 promoter starts at position 2146. The coding sequence for FIV 97TM is from position 2022 to position 42. The I3L promoter starts at position 2253. The FIV gag start codon is at position 2353 and the pol stop codon is at position 3766).

DETAILED DESCRIPTION OF THE INVENTION

Figure 1:
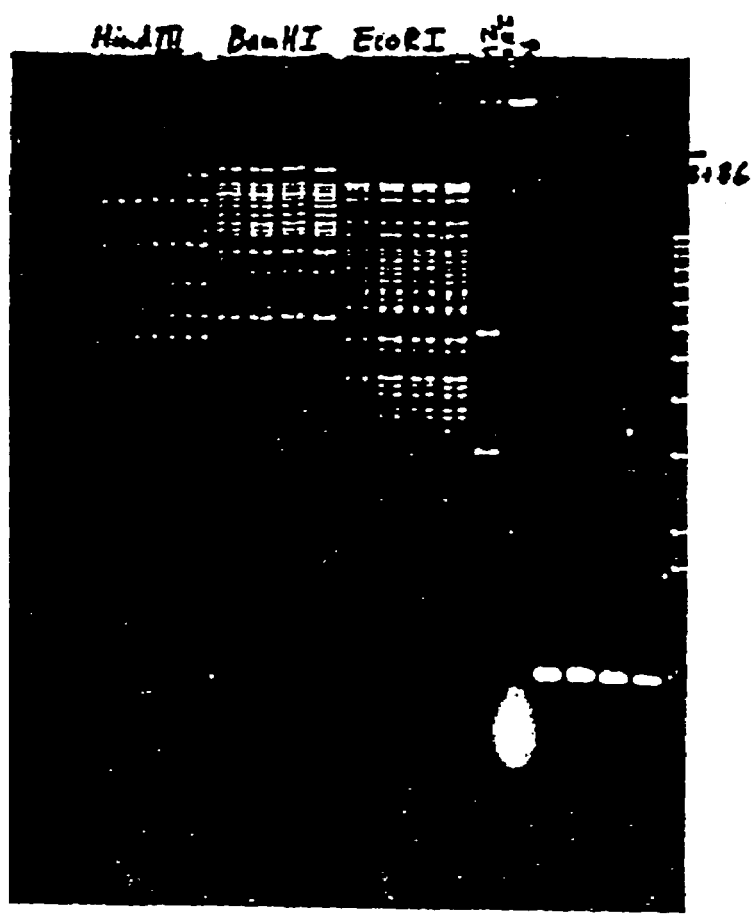
FIG. 1 shows the results of plaque purifying Kanapox, as described above.

As discussed above, the invention specifically relates to: vector-based lentivirus, retrovirus, or immunodeficiency virus, e.g., EIAV, FIV, BIV, HIV, or SIV, preferably feline immunodeficiency virus (FIV) recombinants, preferably recombinants containing DNA encoding an epitope(s) of interest, more preferably Env, Gag, or Pol, or combinations thereof such as Gag and Pol or a portion of Pol, or Env, Gag and Pol or a portion of Pol or Gag and protease, or Env, Gag, and protease, with an attenuated poxvirus such as TROVAC, NYVAC and ALVAC as preferred poxvirus vectors (NYVAC and ALVAC being most preferred, and ALVAC being especially preferred); and, compositions containing the Inventive recombinants or expression products therefrom; and to methods for making and using the inventive recombinants, expression products therefrom and compositions including the recombinants and/or expression products.

Thus, in a general way, the invention provides a vector comprising exogenous DNA encoding at least one lentivirus epitope. The epitope can be from a lentivirus other than SIV. More preferably, the epitope is of Gag and Pol or Env, Gag and Pol or Env, Gag and a portion of Pol or Gag and a portion of Pol or Gag-protease, or Env, Gag, and protease; and, most preferably the epitope is Gag and protease or epitope(s) on Gag and protease which elicit a response which is the same as or similar to Gag and protease. And, the vector preferably induces an immune response, more preferably a protective immune response, when administered to a target species (a target species is a host susceptible to the lentivirus; for instance, felines such as domesticated cats and kittens are a target species with respect to FIV).

The methods for making a vector or recombinant can be by or analogous to the methods disclosed in U.S. Patent Nos. 4,603,112, 4,769,330, 5,174,993, 5,505,941, 5,338,683, 5,494,807, 5,503,834, 4,722,848, 5,514,375, U.K. Patent GB 2 269 820 B, WO 92/22641, WO 93/03145, WO 94/16716, PCT/US94/06652, allowed U.S. application Ser.

No. 08/184,009, filed Jan. 19, 1994, (Paoletti, "Applications of pox virus vectors to vaccination: An update," PNAS USA 93:11349–11353, October 1996, Moss, "Genetically engineered poxviruses for recombinant gene expression, vaccination, and safety," PNAS USA 93:11341–11348, October 1996, Richardson, C. D. (Editor), Methods in Molecular Biology 39, "Baculovirus Expression Protocols" (1995 Humana Press Inc.), Smith et al., "Production of Huma Beta Interferon in Insect Cells Infected with a Baculovirus Expression Vector," Molecular and Cellular Biology, December, 1983, Vol. 3, No. 12, p. 2156–2165; Pennock et al., "Strong and Regulated Expression of *Escherichia coli* B-Galactosidase in Infect Cells with a Baculovirus vector," Molecular and Cellular Biology March 1984, Vol. 4, No. 3, p. 399–406; EPA 0 370 573, U.S. application Serial No. 920,197, filed Oct. 16, 1986, EP Patent publication No. 265785, U.S. Pat. No. 4,769,331, Roizman, "The function of herpes simplex virus genes: A primer for genetic engineering of novel vectors," PNAS USA 93:11307–11312, October 1996, Andreansky et al., "The application of genetically engineered herpes simplex viruses to the treatment of experimental brain tumors," PNAS USA 93:11313–11318, October 1996, Robertson et al. "Epstein-Barr virus vectors for gene delivery to B lymphocytes," PNAS USA 3:11334–11340, October 1996, Frolov et al., "Alphavirus-based expression vectors: Strategies and applications," PNAS USA 93:11371–11377, October 1996, Kitson et al., J. Virol. 65, 3068–3075, 1991; Grunhaus et al., 1992, "Adenovirus as cloning vectors," Seminars in Virology (Vol. 3) p. 237–52, 1993, Ballay et al. EMBO Journal, vol. 4, p. 3861–65, Graham, Tibtech 8, 85–87, April, 1990, Prevec et al., J. Gen Virol. 70, 429–434, U.S. application Ser. Nos. 08/675,556 and 08/675,566, filed Jul. 3, 1996, PCT WO91/11525, Felgner et al. (1994), J. Biol. Chem. 269, 2550–2561, Science, 259:1745–49, 1993 and McClements et al., "Immunization with DNA vaccines encoding glycoprotein D or glycoprotein B, alone or in combination, induces protective immunity in animal models of herpes simplex virus-2 disease," PNAS USA 93:11414–11420, October 1996.

Vaccinia virus and more recently other poxviruses have been used for the insertion and expression of foreign genes. A basic technique of inserting foreign genes into live infectious poxvirus involves recombination between pox DNA sequences flanking a foreign genetic element in a donor plasmid and homologous sequences present in the rescuing poxvirus (Piccini et al., 1987).

Specifically, recombinant poxviruses can be constructed in two steps known in the art and analogous to the methods for creating synthetic recombinants of poxviruses such as the vaccinia virus and avipox virus described in U.S. Pat. Nos. 4,769,330, 4,772,848, 4,603,112, 5,110,587, 5,179,993, 5,505,941, and 5,494,807, the disclosures of which, like the disclosures of all documents cited herein, are incorporated herein by reference.

First, the DNA gene sequence to be inserted into the virus, e.g., an open reading frame from a non-pox source, is placed into a plasmid construct such as an *E. coli* plasmid construct into which DNA homologous to a section of DNA of the poxvirus has been inserted. Separately, the DNA gene sequence to be inserted can be ligated to a promoter. The promoter-gene linkage is positioned in the plasmid construct so that the promoter-gene linkage is flanked on both ends by DNA homologous to a DNA sequence flanking a region of pox DNA; for instance, pox DNA containing a nonessential locus (although an essential locus may also be used). The resulting plasmid construct is then amplified, e.g., by growth within *E. coli* bacteria (Clewell, 1972) and isolated (Clewell et al., 1969; Maniatis et al., 1982). Alternatively, the DNA gene sequence can, without separate ligation to a promoter, merely be placed within the plasmid construct so that the DNA gene sequence is flanked on both ends by DNA homologous to a DNA sequence flanking a region of pox DNA; for instance, a region downstream from an endogenous promoter such that expression of the gene sequence is under control of the promoter and the promoter and coding portion of the DNA gene sequence are thus adjacent.

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, e.g., in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

However, the foregoing is not meant to limit means for obtaining vectors or recombinants of the present invention, as any means for obtaining a vector or recombinant e.g. a poxvirus-lentivirus, retrovirus, and/or immunodeficiency virus, e.g., feline immunodeficiency virus, recombinant may be used to obtain the present invention.

Thus, genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome. Accordingly, additional strategies have recently been reported for generating recombinant poxviruses such as recombinant vaccinia virus; and, these strategies may be employed in the practice of this invention.

Successful expression of the inserted DNA genetic sequence by the modified infectious virus can occur under two conditions. First, the insertion may be into a nonessential region of the virus in order that the modified virus remain viable, or into an essential region whereby the essential function is not disturbed or the function is not necessary for viability under all conditions. A second condition for expression of inserted DNA is the presence of a promoter in the proper relationship to the inserted DNA. The promoter can be located upstream from the coding portion of the DNA sequence to be expressed.

Vaccinia virus has been used successfully to immunize against smallpox, culminating in the worldwide eradication of smallpox in 1980. In the course of its history, many strains of vaccinia have arisen. These different strains demonstrate varying immunogenicity and are implicated to varying degrees with potential complications, the most serious of which are post-vaccinial encephalitis and generalized vaccinia (Behbehani, 1983).

With the eradication of smallpox, a new role for vaccinia became important, that of a genetically engineered vector for the expression of foreign genes. Genes encoding a vast number of heterologous antigens have been expressed in vaccinia, often resulting in protective immunity against challenge by the corresponding pathogen (reviewed in Tartaglia et al., 1990a).

The genetic background of the vaccinia vector has been shown to affect the protective efficacy of the expressed foreign immunogen. For example, expression of Epstein Barr Virus (EBV) gp340 in the Wyeth vaccine strain of vaccinia virus did not protect cottontop tamarins against EBV virus induced lymphoma, while expression of the same gene in the WR laboratory strain of vaccinia virus was protective (Morgan et al., 1988).

A fine balance between the efficacy and the safety of a vaccinia virus-based recombinant vaccine candidate is extremely important. The recombinant virus must present the immunogen(s) in a manner that elicits a protective immune response in the vaccinated animal but lacks any significant pathogenic properties. Therefore attenuation of the vector strain would be a highly desirable advance over the current state of technology.

A number of vaccinia genes have been identified which are non-essential for growth of the virus in tissue culture and whose deletion or inactivation reduces virulence in a variety of animal systems.

The gene encoding the vaccinia virus thymidine kinase (TK) has been mapped (Hruby et al., 1982) and sequenced (Hruby et al., 1983; Weir et al., 1983). Inactivation or complete deletion of the thymidine kinase gene does not prevent growth of vaccinia virus in a wide variety of cells in tissue culture. TK⁻ vaccinia virus is also capable of replication in vivo at the site of inoculation in a variety of hosts by a variety of routes.

It has been shown for herpes simplex virus type 2 that intravaginal inoculation of guinea pigs with TK⁻ virus resulted in significantly lower virus titers in the spinal cord than did inoculation with TK⁺ virus (Stanberry et al., 1985). It has been demonstrated that herpesvirus encoded TK activity in vitro was not important for virus growth in actively metabolizing cells, but was required for virus growth in quiescent cells (Jamieson et al., 1974).

Attenuation of TK⁻ vaccinia has been shown in mice inoculated by the intracerebral and intraperitoneal routes (Buller et al., 1985). Attenuation was observed both for the WR neurovirulent laboratory strain and for the Wyeth vaccine strain. In mice inoculated by the intradermal route, TK⁻ recombinant vaccinia generated equivalent anti-vaccinia neutralizing antibodies as compared with the parental TK⁺ vaccinia virus, indicating that in this test system the loss of TK function does not significantly decrease immunogenicity of the vaccinia virus vector. Following intranasal inoculation of mice with TK⁻ and TK⁺ recombinant vaccinia virus (WR strain), significantly less dissemination of virus to other locations, including the brain, has been found (Taylor et al., 1991a).

Another enzyme involved with nucleotide metabolism is ribonucleotide reductase. Loss of virally encoded ribonucleotide reductase activity in herpes simplex virus (HSV) by deletion of the gene encoding the large subunit was shown to have no effect on viral growth and DNA synthesis in dividing cells in vitro, but severely compromised the ability of the virus to grow on serum starved cells (Goldstein et al., 1988). Using a mouse model for acute HSV infection of the eye and reactivatable latent infection in the trigeminal ganglia, reduced virulence was demonstrated for HSV deleted of the large subunit of ribonucleotide reductase, compared to the virulence exhibited by wild type HSV (Jacobson et al., 1989).

Both the small (Slabaugh et al., 1988) and large (Schmidtt et al., 1988) subunits of ribonucleotide reductase have been identified in vaccinia virus. Insertional inactivation of the large subunit of ribonucleotide reductase in the WR strain of vaccinia virus leads to attenuation of the virus as measured by intracranial inoculation of mice (Child et al., 1990).

The vaccinia virus hemagglutinin gene (HA) has been mapped and sequenced (Shida, 1986). The HA gene of vaccinia virus is nonessential for growth in tissue culture (Ichihashi et al., 1971). Inactivation of the HA gene of vaccinia virus results in reduced neurovirulence in rabbits inoculated by the intracranial route and smaller lesions in rabbits at the site of intradermal inoculation (Shida et al., 1988). The HA locus was used for the insertion of foreign genes in the WR strain (Shida et al., 1987), derivatives of the Lister strain (Shida et al., 1988) and the Copenhagen strain (Guo et al., 1989) of vaccinia virus. Recombinant HA⁻ vaccinia virus expressing foreign genes have been shown to be immunogenic (Guo et al., 1989; Itamura et al., 1990; Shida et al., 1988; Shida et al., 1987) and protective against challenge by the relevant pathogen (Guo et al., 1989; Shida et al., 1987).

Cowpox virus (Brighton red strain) produces red (hemorrhagic) pocks on the chorioallantoic membrane of chicken eggs. Spontaneous deletions within the cowpox genome generate mutants which produce white pocks (Pickup et al., 1984). The hemorrhagic function (u) maps to a 38 kDa protein encoded by an early gene (Pickup et al., 1986). This gene, which has homology to serine protease inhibitors, has been shown to inhibit the host inflammatory response to cowpox virus (Palumbo et al., 1989) and is an inhibitor of blood coagulation.

The u gene is present in WR strain of vaccinia virus (Kotwal et al., 1989b). Mice inoculated with a WR vaccinia virus recombinant in which the u region has been inactivated by insertion of a foreign gene produce higher antibody levels to the foreign gene product compared to mice inoculated with a similar recombinant vaccinia virus in which the u gene is intact (Zhou et al., 1990). The u region is present in a defective nonfunctional form in Copenhagen strain of vaccinia virus (open reading frames B13 and B14 by the terminology reported in Goebel et al., 1990a,b).

Cowpox virus is localized in infected cells in cytoplasmic A type inclusion bodies (ATI) (Kato et al., 1959). The function of ATI is thought to be the protection of cowpox virus virions during dissemination from animal to animal (Bergoin et al., 1971). The ATI region of the cowpox genome encodes a 160 kDa protein which forms the matrix of the ATI bodies (Funahashi et al., 1988; Patel et al., 1987). Vaccinia virus, though containing a homologous region in its genome, generally does not produce ATI. In WR strain of vaccinia, the ATI region of the genome is translated as a 94 kDa protein (Patel et al., 1988). In Copenhagen strain of vaccinia virus, most of the DNA sequences corresponding to the ATI region are deleted, with the remaining 3' end of the region fused with sequences upstream from the ATI region to form open reading frame (ORF) A26L (Goebel et al., 1990a,b).

A variety of spontaneous (Altenburger et al., 1989; Drillien et al., 1981; Lai et al., 1989; Moss et al., 1981; Paez et al., 1985; Panicali et al., 1981) and engineered (Perkus et al., 1991; Perkus et al., 1989; Perkus et al., 1986) deletions have been reported near the left end of the vaccinia virus genome. A WR strain of vaccinia virus with a 10 kb spontaneous deletion (Moss et al., 1981; Panicali et al., 1981) was shown to be attenuated by intracranial inoculation in mice (Buller et al., 1985). This deletion was later shown to include 17 potential ORFs (Kotwal et al., 1988b). Specific genes within the deleted region include the virokine N1L and a 35 kDa protein (C3L, by the terminology reported in Goebel et al., 1990a,b). Insertional inactivation of N1L reduces virulence by intracranial inoculation for both normal and nude mice (Kotwal et al., 1989a). The 35 kDa protein is secreted like N1L into the medium of vaccinia virus infected cells. The protein contains homology to the family of complement control proteins, particularly the complement 4B binding protein (C4 bp) (Kotwal et al., 1988a). Like the cellular C4 bp, the vaccinia 35 kDa protein binds the fourth component of complement and inhibits the classical complement cascade (Kotwal et al., 1990). Thus the vaccinia 35 kDa protein appears to be involved in aiding the virus in evading host defense mechanisms.

The left end of the vaccinia genome includes two genes which have been identified as host range genes, K1L (Gillard et al., 1986) and C7L (Perkus et al., 1990). Deletion of both of these genes reduces the ability of vaccinia virus to grow on a variety of human cell lines (Perkus et al., 1990).

To develop a new vaccinia vaccine strain, NYVAC (vP866), the Copenhagen vaccine strain of vaccinia virus was modified by the deletion of six nonessential regions of the genome encoding known or potential virulence factors. The sequential deletions are detailed in U.S. Pat. Nos. 5,364,773 and 5,494,807. All designations of vaccinia restriction fragments, open reading frames and nucleotide positions are based on the terminology reported in Goebel et al., 1990a,b.

The deletion loci were also engineered as recipient loci for the insertion of foreign genes.

The regions deleted in NYVAC are listed below. Also listed are the abbreviations and open reading frame designations for the deleted regions (Goebel et al., 1990a,b) and the designation of the vaccinia recombinant (vP) containing all deletions through the deletion specified:

(1) thymidine kinase gene (TK; J2R) vP410;
(2) hemorrhagic region (u; B13R+B14R) vP553;
(3) A type inclusion body region (ATI; A26L) vP618;
(4) hemagglutinin gene (HA; A56R) vP723;
(5) host range gene region (C7L-K1L) vP804; and
(6) large subunit, ribonucleotide reductase (I4L) vP866 (NYVAC).

NYVAC is a genetically engineered vaccinia virus strain that was generated by the specific deletion of eighteen open reading frames encoding gene products associated with virulence and host range. NYVAC is highly attenuated by a number of criteria including i) decreased virulence after intracerebral inoculation in newborn mice, ii) inocuity in genetically ($nu^+/nu^+$) or chemically (cyclophosphamide) immunocompromised mice, iii) failure to cause disseminated infection in immunocompromised mice, iv) lack of significant induration and ulceration on rabbit skin, v) rapid clearance from the site of inoculation, and vi) greatly reduced replication competency on a number of tissue culture cell lines including those of human origin. Nevertheless, NYVAC based vectors induce excellent responses to extrinsic immunogens and provided protective immunity.

Two additional vaccine vector systems involve the use of naturally host-restricted poxviruses, avipox viruses. Both fowlpoxvirus (FPV) and canarypoxvirus (CPV) have been engineered to express foreign gene products. Fowlpox virus (FPV) is the prototypic virus of the Avipox genus of the Poxvirus family. The virus causes an economically important disease of poultry which has been well controlled since the 1920's by the use of live attenuated vaccines. Replication of the avipox viruses is limited to avian species (Matthews, 1982) and there are no reports in the literature of avipox virus causing a productive infection in any non-avian species including man. This host restriction provides an inherent safety barrier to transmission of the virus to other species and makes use of avipox virus based vaccine vectors in veterinary and human applications an attractive proposition.

FPV has been used advantageously as a vector expressing antigens from poultry pathogens. The hemagglutinin protein of a virulent avian influenza virus was expressed in an FPV recombinant (Taylor et al., 1988a). After inoculation of the recombinant into chickens and turkeys, an immune response was induced which was protective against either a homologous or a heterologous virulent influenza virus challenge (Taylor et al., 1988a). FPV recombinants expressing the surface glycoproteins of Newcastle Disease Virus have also been developed (Taylor et al., 1990; Edbauer et al., 1990).

Despite the host-restriction for replication of FPV and CPV to avian systems, recombinants derived from these viruses were found to express extrinsic proteins in cells of nonavian origin. Further, such recombinant viruses were shown to elicit immunological responses directed towards the foreign gene product and where appropriate were shown to afford protection from challenge against the corresponding pathogen (Tartaglia et al., 1993a,b; Taylor et al., 1992; 1991b; 1988b).

The ALVAC recombinants can be by the methods detailed in Piccini et al. 1983; Perkus et.al. 1995, e.g., recombination, which is novel and nonobvious with respect the present invention as a novel and nonobvious product results therefrom.

TROVAC refers to an attenuated fowlpox that was a plaque-cloned isolate derived from the FP-1 vaccine strain of fowlpoxvirus which is licensed for vaccination of 1 day old chicks. TROVAC is a unimolar fowlpox virus species.

ALVAC is an attenuated canarypox virus-based vector that was a plaque-cloned derivative of the licensed canarypox vaccine, Kanapox (Tartaglia et al., 1992). ALVAC has some general properties which are the same as some general properties of Kanapox. ALVAC is a unimolar canarypox virus species.

ALVAC-based recombinant viruses expressing extrinsic immunogens have also been demonstrated efficacious as vaccine vectors (Tartaglia et al., 1993a,b). This avipox vector is restricted to avian species for productive replication. On human cell cultures, canarypox virus replication is aborted early in the viral replication cycle prior to viral DNA synthesis. Nevertheless, when engineered to express extrinsic immunogens, authentic expression and processing is observed in vitro in mammalian cells and inoculation into numerous mammalian species induces antibody and cellular immune responses to the extrinsic immunogen and provides protection against challenge with the cognate pathogen (Taylor et al., 1992; Taylor et al., 1991).

Recent Phase I clinical trials in both Europe and the United States of a ALVAC recombinants, e.g., canarypox/rabies glycoprotein recombinant (ALVAC-RG), demonstrated that ALVAC vaccines are safe and well tolerated and, for instance, induced protective levels of rabies virus neutralizing antibody titers (Fries et al., 1996; Pialoux et al., 1994; Cadoz et al., 1992). Additionally, peripheral blood mononuclear cells (PBMCs) derived from the ALVAC-RG vaccinates demonstrated significant levels of lymphocyte proliferation when stimulated with purified rabies virus (Fries et al., 1996).

NYVAC, ALVAC and TROVAC have also been recognized as unique among all poxviruses in that the National Institutes of Health ("NIH") (U.S. Public Health Service), Recombinant DNA Advisory Committee, which issues guidelines for the physical containment of genetic material such as viruses and vectors, i.e., guidelines for safety procedures for the use of such viruses and vectors which are based upon the pathogenicity of the particular virus or vector, granted a reduction in physical containment level: from BSL2 to BSL1. No other poxvirus has a BSL1 physical containment level. Even the Copenhagen strain of vaccinia virus—the common smallpox vaccine—has a higher physical containment level; namely, BSL2. Accordingly, the art has recognized that ALVAC has a lower pathogenicity than other poxvirus.

ALVAC-based recombinant viruses have been shown to stimulate in vitro specific $CD8^+$ CTLs from human PBMCs (Tartaglia et al., 1993a). Mice immunized with ALVAC recombinants expressing various forms of the HIV-1 envelope glycoprotein generated both primary and memory HIV specific CTL responses which could be recalled by a second inoculation (Tartaglia et al., 1993a; Cox et al., 1993). ALVAC-env recombinants (expressing the HIV-1 envelope glycoprotein) stimulated strong HIV-specific CTL responses from peripheral blood mononuclear cells (PBMC) of HIV-1 infected individuals (Tartaglia et al., 1993a; Cox et al., 1993). Acutely infected autologous PBMC were used as stimulator cells for the remaining PBMC. After 10 days incubation in the absence of exogenous IL-2, the cells were evaluated for CTL activities. ALVAC-env stimulated high levels of anti-HIV activities in mice. These and similar studies (see U.S. Ser. No. 08/417,210) show a utility of ALVAC-based recombinants, especially with respect to immunodeficiency viruses. In particular, the highly attenuated character of ALVAC has been demonstrated in both immunocompetent and immuno-compromised animal models in such studies; and, the safety of ALVAC-based recombinants has also been demonstrated.

Thus, in the present invention, the canarypox virus-based ALVAC vector is preferred.

Clearly, based on the attenuation profiles of the ALVAC vectors and its demonstrated ability to elicit both humoral and cellular immunological responses to extrinsic immunogens (Tartaglia et al., 1993a,b; Taylor et al., 1992) such recombinant viruses offer a distinct advantage over previously described vaccinia based recombinant viruses.

Perhaps more related to FIV (as felines are involved), an ALVAC-based recombinant virus expressing the FeLV (Subgroup A) env and gag gene products (ALVAC-FL; vCP97) was shown to afford complete protection of cats against an oronasal FeLV challenge exposure (Tartaglia et al., 1993). Significantly, protection was afforded in the absence of detectable FeLV-specific serum neutralizing activity prior to challenge.

In certain embodiments of the present invention, Applicants have engineered several ALVAC-FIV recombinants and assessed their ability to afford protection of cats against experimental FIV exposure. In summary, Applicants have demonstrated protection from homologous FIV challenge exposure by vaccination of cats with an ALVAC-FIV Gag-protease recombinant. Recombinants expressing FIV Env alone or in combination with Gag-protease did not afford significant levels of protection. However, vaccination regimens consisting of priming with ALVAC-FIV env/gag-protease and boosting with an adjuvanted inactivated whole cell vaccine preparation provided complete protection, demonstrating utility for the recombinants expressing Env alone or in combination with Gag-protease, despite these recombinants not per se affording significant levels of protection (and further, these recombinants can be used in other aspects of the invention, e.g., to express products which can nonetheless be useful, for instance to obtain useful antibodies, or in kits, tests, assays and the like).

Interestingly, levels of FIV-specific humoral responses measured by ELISA and western blot were not necessarily predictive of protection. Furthermore, Env-specific humoral responses were not associated with the observed protection.

Furthermore, the data herein shows the efficacy of recombinants of the present invention against heterologous FIV challenge in cats, especially in a prime/boost protocol involving an inventive recombinant (e.g., an ALVAC-FIV recombinant) and an ICV.

Moreover, the data herein with respect to FIV and cats is capable of extension to other lentiviruses, retroviruses, and immunodeficiency viruses, e.g., e.g., EIAV, FIV, BIV, HIV, or SIV. Thus, knowledge in the art of nucleic acid molecules encoding epitope(s) of interest from these other viruses, e.g., Env, Gag, protease, can be utilized for making and using recombinants expressing epitope(s) of interest analogous to the exemplified FIV data herein. More in particular, using the knowledge in the art of nucleic acid molecules encoding Env, Gag, Pol, or a portion of Pol, such as a portion including protease, accessory functions/proteins, or epitope(s) thereof, for other lentiviruses, retroviruses, and immunodeficiency viruses, e.g., EIAV, FIV, BIV, HIV, or SIV, and using the knowledge in the art of vector systems, the skilled artisan can make vectors or recombinants expressing Env, Gag and Pol or a portion of Pol, or Gag and Pol or a portion of Pol, or Env, Gag and protease, or Gag and protease, with optionally accessory functions/proteins, or expressing epitope(s) thereof, of these other viruses, and can use the vectors or recombinants in an immunization regimen, such as a prime/boost regimen, as herein exemplified with respect to FIV, without any undue experimentation. Accordingly, the invention encompasses vectors or recombinants of lentiviruses, retroviruses and immunodeficiency viruses in addition to FIV (as FIV is a model for other lentiviruses, retroviruses and immunodeficiency viruses), and methods of making and using those vectors or recombinants.

The expression product generated by inventive vectors or recombinants can also be isolated from infected or transfected cells and used to inoculate hosts in a subunit vaccine configuration (composition, or an antigenic or immunological composition). The proteins generated by the vectors or recombinants and antibodies elicited therefrom can also be used in assays to detect the presence or absence of a lentivirus, retrovirus or immunodeficiency virus, e.g., FIV.

Accordingly, the invention comprehends immunogens or epitope(s) of interest such as lentivirus, retrovirus or immunodeficiency virus immunogen(s) or epitope(s) of interest, e.g., EIAV, FIV, BIV, HIV, or SIV immunogens or epitopes of interest. Indeed, the invention comprehends immunogens or epitopes of interest from lentiviruses, including but not limited to HIV-1,-2, EIAV, BIV. All lentiviruses express functional homologs of the FIV Env, Gag-protease. Techniques for identifying, cloning and utilizing nucleic acid sequences encoding these functional homologs are known in the art and do not require any undue experimentation to practice in the light of this disclosure.

With respect to the state-of-the-art, mention is particularly made of: Gonda et al. (1990). Development of bovine immunodeficiency-like virus as a model of lentivirus disease. *Dev. Biol. Stand.* 72:97–110; Garvey et al. (1990) Nucleotide sequence and genome organization of biologically active bovine immunodeficiency-like virus. *Virology* 175:391–409; Gonda et al. (1987). Characterization and molecular cloning of a bovine lentivirus related to human immunodeficiency virus. Nature 330:388–391; Ball et al. (1988). EIAV genomic organization: further characterization by sequencing of purified glycoproteins and cDNA. *Virology* 165: 601–605; Kawakami et al. (1987) Nucleotide sequence analysis of equine infectious anemia virus proviral DNA. *Virology* 158: 300–312; Yaniv et al. (1986) Molecular cloning and physical characterization of integrated equine infectious anemia virus:molecular and immunologic evidence of it's close relationship to ovine and caprine lentiviruses. *Virology* 154: 1–8; Stephens et al. (1986). Equine infectious anemia virus gag and pol genes: relatedness to visna and AIDS virus. *Science* 231:589–594; Chiu et al. (1985). Nucleotide evidence for relationship of AIDS retrovirus to lentiviruses. *Nature* 317:366–368; as well as a number of reviews in *Retrovirus Biology and Human Disease*, Gallo, R. C. and Wong-Stall, F. eds. Marcel Dekker, Inc. New York, 1990.

Further, DNA encoding such immunogens or epitopes of interest from inventive vectors or recombinants can be administered through immunization using alternate appropriately engineered mammalian expression systems including but not limited to other poxviruses, herpesviruses, adenoviruses, alphavirus-based strategies, and naked or formulated DNA-based immunogens. Techniques for engineering such recombinant subunits are known in the art.

With respect to techniques for these immunization vehicles and state-of-the-art knowledge mention is particularly made of: Hormaeche and Kahn, Perkus and Paoletti, Shiver et al. all in *Concepts in Vaccine Development*, Kaufman, S. H. E., ed., Walter deGruytes, New York, 1996, and vectors described in *Viruses in Human Gene Therapy*, Vos, J.-M. H., ed, Chapman and Hall, Carolina Academic Press, New York, 1995, and in Recombinant *Vectors in Vaccine Development*, Brown, F., ed., Karger, New York, 1994.

The invention still further provides an antigenic, immunogenic, immunological or vaccine composition containing the recombinant virus or expression product thereof, and a acceptable carrier or diluent. An immunological composition containing the vector or recombinant virus (or an expression product thereof) elicits an immunological response—local or systemic. The response can, but need not be, protective. An immunogenic composition containing the vector or recombinant virus (or an expression product thereof) likewise elicits a local or systemic immunological response which can, but need not be, protective. An antigenic composition similarly elicits a local or systemic immunological response which can, but need not be, protective. A vaccine composition elicits a local or systemic protective response. Accordingly, the terms "immunological composition", "antigenic composition" and "immunogenic composition" include a "vaccine composition" (as the three former terms can be protective compositions). A protective response is understood to be a response, such as a humoral and/or secretory and/or cell-mediated response which confers an immunity, with immunity understood to comprise the ability to resist or overcome infection or to overcome infection more easily as compared to a subject not administered the inventive composition, or to better tolerate infection as compared to a subject not administered the inventive composition, e.g., increased resistance to infection.

As to epitopes of interest, one skilled in the art can determine an epitope or immunodominant region of a peptide or polypeptide and ergo the coding DNA therefor from the knowledge of the amino acid and corresponding DNA sequences of the peptide or polypeptide, as well as from the nature of particular amino acids (e.g., size, charge, etc.) and the codon dictionary, without undue experimentation.

A general method for determining which portions of a protein to use in an immunological composition focuses on the size and sequence of the antigen of interest. "In general, large proteins, because they have more potential determinants are better antigens than small ones. The more foreign an antigen, that is the less similar to self configurations which induce tolerance, the more effective it is in provoking an immune response." Ivan Roitt, *Essential Immunology*, 1988.

As to size: the skilled artisan can maximize the size of the protein encoded by the DNA sequence to be inserted into the mammalian vector (keeping in mind the insertion limitations of the vector). To minimize the DNA inserted while maximizing the size of the protein expressed, the DNA sequence can exclude introns (regions of a gene which are transcribed but which are subsequently excised from the primary RNA transcript).

At a minimum, the DNA sequence can code for a peptide at least 8 or 9 amino acids long. This is the minimum length that a peptide needs to be in order to stimulate a CD4+ T cell response (which recognizes virus infected cells or cancerous cells). A minimum peptide length of 13 to 25 amino acids is useful to stimulate a CD8+ T cell response (which recognizes special antigen presenting cells which have engulfed the pathogen). See Kendrew, *The Encyclopedia of Molecular Biology* (Blackwell Science Ltd 1995). However, as these are minimum lengths, these peptides are likely to generate an immunological response, i.e., an antibody or T cell response; but, for a protective response (as from a vaccine composition), a longer peptide is preferred.

With respect to the sequence, the DNA sequence preferably encodes at least regions of the peptide that generate an antibody response or a T cell response. One method to determine T and B cell epitopes involves epitope mapping. The protein of interest "is fragmented into overlapping peptides with proteolytic enzymes. The individual peptides are then tested for their ability to bind to an antibody elicited by the native protein or to induce T cell or B cell activation. This approach has been particularly useful in mapping T-cell epitopes since the T cell recognizes short linear peptides complexed with MHC molecules. The method is less effective for determining B-cell epitopes" since B cell epitopes are often not linear amino acid sequence but rather result from the tertiary structure of the folded three dimensional protein. Janis Kuby, *Immunology*, pp. 79–80 (1992).

Another method for determining an epitope of interest is to choose the regions of the protein that are hydrophilic. Hydrophilic residues are often on the surface of the protein and are therefore often the regions of the protein which are accessible to the antibody. Janis Kuby, *Immunology*, p. 81 (1992).

Yet another method for determining an epitope of interest is to perform an X-ray crystallographic analysis of the antigen (full length)-antibody complex. Janis Kuby, *Immunology*, p. 80 (1992).

Still another method for choosing an epitope of interest which can generate a T cell response is to identify from the protein sequence potential HLA anchor binding motifs which are peptide sequences which are known to be likely to bind to the MHC molecule.

The peptide which is a putative epitope of interest, to generate a T cell response, should be presented in a MHC complex. The peptide preferably contains appropriate anchor motifs for binding to the MHC molecules, and should bind with high enough affinity to generate an immune response. Factors which can be considered are: the HLA type of the patient (vertebrate, animal or human) expected to be immunized, the sequence of the protein, the presence of appropriate anchor motifs and the occurrence of the peptide sequence in other vital cells.

An immune response is generated, in general, as follows: T cells recognize proteins only when the protein has been cleaved into smaller peptides and is presented in a complex called the "major histocompatibility complex MHC" located on another cell's surface. There are two classes of MHC complexes—class I and class II, and each class is made up of many different alleles. Different patients have different types of MHC complex alleles; they are said to have a 'different HLA type.'

Class I MHC complexes are found on virtually every cell and present peptides from proteins produced inside the cell. Thus, Class I MHC complexes are useful for killing cells which when infected by viruses or which have become cancerous and as the result of expression of an oncogene. T cells which have a protein called CD4 on their surface, bind to the MHC class I cells and secrete lymphokines. The lymphokines stimulate a response; cells arrive and kill the viral infected cell.

Class II MHC complexes are found only on antigen-presenting cells and are used to present peptides from circulating pathogens which have been endocytosed by the antigen-presenting cells. T cells which have a protein called CD8 bind to the MHC class I cells and kill the cell by exocytosis of lytic granules.

Some guidelines in determining whether a protein contains epitopes of interest which will stimulate a T cell response, include: Peptide length—the peptide should be at least 8 or 9 amino acids long to fit into the MHC class I complex and at least 13–25 amino acids long to fit into a class II MCH complex. This length is a minimum for the peptide to bind to the MHC complex. It is preferred for the peptides to be longer than these lengths because cells may cut the expressed peptides. The peptide should contain an appropriate anchor motif which will enable it to bind to the various class I or class II molecules with high enough specificity to generate an immune response (See Bocchia, M. et al., *Specific Binding of Leukemia Oncogene Fusion Protein Peptides to HLA Class I Molecules*, Blood 85:2680–2684; Englehard, V H, *Structure of peptides associated with class I and class II MHC molecules* Ann. Rev. Immunol. 12:181 (1994)). This can be done, without undue experimentation, by comparing the sequence of the protein of interest with published structures of peptides associated with the MHC molecules. Protein epitopes recognized by T cell receptors are peptides generated by enzymatic degradation of the protein molecule and are presented on the cell surface in association with class I or class II MHC molecules.

Further, the skilled artisan can ascertain an epitope of interest by comparing the protein sequence with sequences listed in the protein data base. Regions of the protein which share little or no homology are better choices for being an epitope of that protein and are therefore useful in a vaccine or immunological composition. Regions which share great homology with widely found sequences present in vital cells should be avoided.

Even further, another method is simply to generate or express portions of a protein of interest, generate monoclonal antibodies to those portions of the protein of interest, and then ascertain whether those antibodies inhibit growth in vitro of the pathogen from which the from which the protein was derived. The skilled artisan can use the other guidelines set forth in this disclosure and in the art for generating or expressing portions of a protein of interest for analysis as to whether antibodies thereto inhibit growth in vitro.

For example, the skilled artisan can generate portions of a protein of interest by: selecting 8 to 9 or 13 to 25 amino acid length portions of the protein, selecting hydrophilic regions, selecting portions shown to bind from X-ray data of the antigen (full length)-antibody complex, selecting regions which differ in sequence from other proteins, selecting potential HLA anchor binding motifs, or any combination of these methods or other methods known in the art.

Epitopes recognized by antibodies are expressed on the surface of a protein. To determine the regions of a protein most likely to stimulate an antibody response one skilled in the art can preferably perform an epitope map, using the general methods described above, or other mapping methods known in the art.

As can be seen from the foregoing, without undue experimentation, from this disclosure and the knowledge in the art, the skilled artisan can ascertain the amino acid and corresponding DNA sequence of a lentivirus epitope of interest for obtaining a T cell, B cell and/or antibody response. In addition, reference is made to Gefter et al., U.S. Pat. No. 5,019,384, issued May 28, 1991, and the documents it cites, incorporated herein by reference (Note especially the "Relevant Literature" section of this patent, and column 13 of this patent which discloses that: "A large number of epitopes have been defined for a wide variety of organisms of interest. Of particular interest are those epitopes to which neutralizing antibodies are directed. Disclosures of such epitopes are in many of the references cited in the Relevant Literature section.")

The administration procedure for the inventive vector or recombinant or expression product thereof, compositions of the invention such as immunological, antigenic or vaccine compositions or therapeutic compositions can be via a parenteral route (intradermal, intramuscular or subcutaneous). Such an administration enables a systemic immune response. The administration can be via a mucosal route, e.g., oral, nasal, genital, etc. Such an administration enables a local immune response.

More generally, the inventive antigenic, immunological or vaccine compositions or therapeutic compositions (compositions containing the vectors or recombinants of the invention or expression products) can be prepared in accordance with standard techniques well known to those skilled in the pharmaceutical or veterinary arts. Such compositions can be administered in dosages and by techniques well known to those skilled in the medical and/or veterinary arts taking into consideration such factors as the breed or species, age, sex, weight, and condition of the particular patient, and the route of administration. The compositions can be administered alone, or can be co-administered or sequentially administered with other compositions of the invention or with other immunological, antigenic or vaccine or therapeutic compositions. Such other compositions can include purified native antigens or epitopes or antigens or epitopes from the expression by a poxvirus recombinant or another vector system; and are administered taking into account the aforementioned factors.

Examples of compositions of the invention include liquid preparations for orifice, e.g., oral, nasal, anal, genital, e.g., vaginal, etc., administration such as suspensions, syrups or elixirs; and, preparations for parenteral, subcutaneous, intradermal, intramuscular or intravenous administration (e.g., injectable administration) such as sterile suspensions or emulsions. In such compositions the recombinant may be in admixture with a suitable carrier, diluent, or excipient such as sterile water, physiological saline, glucose or the like.

Antigenic, immunological or vaccine compositions typically can contain an adjuvant and an amount of the recombinant or expression product to elicit the desired response. In human applications, alum (aluminum phosphate or aluminum hydroxide) is a typical adjuvant. Saponin and its purified component Quil A, Freund's complete adjuvant and other adjuvants are used in research and veterinary applications. Chemically defined preparations such as muramyl dipeptide, monophosphoryl lipid A, phospholipid conjugates such as those described by Goodman-Snitkoff et al., *J. Immunol.* 147:410–415 (1991) and incorporated by reference herein, encapsulation of the protein within a proteoliposome as described by Miller et al., *J. Exp. Med.* 176: 1739–1744 (1992) and incorporated by reference herein, and encapsulation of the protein in lipid vesicles such as Novasome™ lipid vesicles (Micro Vesicular Systems, Inc., Nashua, NH) can also be used.

The compositions of the invention may be packaged in a single dosage form for immunization by parenteral (i.e., intramuscular, intradermal or subcutaneous) administration or orifice administration, e.g., perlingual (i.e., oral), intragastric, mucosal including intraoral, intraanal, intravaginal, and the like administration. And again, the effective dosage and route of administration are determined by the nature of the composition, by the nature of the expression product, by expression level if the vector or recombinant is directly used, and by known factors, such as breed or species, age, sex, weight, condition and nature of host, as well as $LD_{50}$ and other screening procedures which are known and do not require undue experimentation.

Dosages of expressed product can range from a few to a few hundred micrograms, e.g., 5 to 500 µg. The inventive vector or recombinant can be administered in any suitable amount to achieve expression at these dosage levels. The inventive vector or recombinant can be administered to an animal or infected or transfected into cells in an amount of about at least $10^{3.5}$ pfu; thus, the inventive vector or recombinant is preferably administered to an animal or infected or transfected into cells in at least about $10^4$ pfu to about $10^6$ pfu; however, as shown by the Examples below, animals can be administered at least about $10^8$ pfu such that a more preferred amount for administration can be at least about $10^7$ pfu to about $10^9$ pfu. Other suitable carriers or diluents can be water or a buffered saline, with or without a preservative. The expression product or vector or recombinant may be lyophilized for resuspension at the time of administration or can be in solution.

The carrier may also be a polymeric delayed release system. Synthetic polymers are particularly useful in the formulation of a composition having controlled release. An early example of this was the polymerization of methyl methacrylate into spheres having diameters less than one micron to form so-called nano particles, reported by Kreuter, J., *Microcapsules and Nanoparticles in Medicine and Pharmacology*, (M. Donbrow, ed.) CRC Press, p. 125–148.

Microencapsulation has been applied to the injection of microencapsulated pharmaceuticals to give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters and polyamides, particularly those that are biodegradable.

A frequent choice of a carrier for pharmaceuticals and more recently for antigens is poly (d,1-lactide-co-glycolide) (PLGA). This is a biodegradable polyester that has a long history of medical use in erodible sutures, bone plates and other temporary prostheses where it has not exhibited any toxicity. A wide variety of pharmaceuticals including peptides and antigens have been formulated into PLGA microcapsules. A body of data has accumulated on the adaption of PLGA for the controlled release of antigen, for example, as reviewed by Eldridge, J. H., et al., *Current Topics in Microbiology and Immunology*, 1989, 146:59–66. The entrapment of antigens in PLGA microspheres of 1 to 10 microns in diameter has been shown to have a remarkable adjuvant effect when administered orally. The PLGA microencapsulation process uses a phase separation of a water-in-oil emulsion. The compound of interest is prepared as an aqueous solution and the PLGA is dissolved in a suitable organic solvents such as methylene chloride and ethyl acetate. These two immiscible solutions are co-emulsified by high-speed stirring. A non-solvent for the polymer is then added, causing precipitation of the polymer around the aqueous droplets to form embryonic microcapsules. The microcapsules are collected, and stabilized with one of an assortment of agents (polyvinyl alcohol (PVA), gelatin, alginates, polyvinylpyrrolidone (PVP), methyl cellulose) and the solvent removed by either drying in vacuo or solvent extraction.

Thus, solid, including solid-containing-liquid, liquid, and gel (including "gel caps") compositions are envisioned.

Additionally, the inventive vector or recombinant, and the expression products therefrom can stimulate an immune or antibody response in animals. From those antibodies, by techniques well-known in the art, monoclonal antibodies can be prepared and, those monoclonal antibodies, can be employed in well known antibody binding assays, diagnostic kits or tests to determine the presence or absence of antigen(s) and therefrom the presence or absence of the natural causative agent of the antigen or, to determine whether an immune response to that agent or to the antigen(s) has simply been stimulated.

Monoclonal antibodies are immunoglobulin produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, e.g., Koprowski, H. et al., U.S. Pat. No. 4,196,265, issued Apr. 1, 1989, incorporated herein by reference.

Uses of monoclonal antibodies are known. One such use is in diagnostic methods, e.g., David, G. and Greene, H., U.S. Pat. No. 4,376,110, issued Mar. 8, 1983, incorporated herein by reference.

Monoclonal antibodies have also been used to recover materials by immunoadsorption chromatography, e.g. Milstein, C., 1980, Scientific American 243:66, 70, incorporated herein by reference.

Furthermore, the inventive vector or recombinant or expression products therefrom can be used to stimulate a response in cells in vitro or ex vivo for subsequent reinfusion into a patient. If the patient is seronegative, the reinfusion is to stimulate an immune response, e.g., an immunological or antigenic response such as active immunization. In a seropositive patient, the reinfusion is to stimulate or boost the immune system against the lentivirus, retrovirus, or immunodeficiency virus, e.g., FIV.

Accordingly, the inventive vector or recombinant has several utilities: In antigenic, immunological or vaccine compositions such as for administration to seronegative animals or humans (or patients, as veterinarians like to call animals, with "patients" including humans as well). In therapeutic compositions in seropositive animals or humans in need of therapy to stimulate or boost the immune system against the lentivirus, retrovirus, or immunodeficiency virus, e.g., feline immunodeficiency virus. In vitro to produce antigens or immunogens or epitopes of interest, which can be further used in antigenic, immunological or vaccine compositions or in therapeutic compositions. To generate antibodies (either by direct administration or by administration of an expression product of the inventive vectors or recombinants) which can be further used: in diagnosis, tests or kits to ascertain the presence or absence of antigens or epitopes in a sample such as sera, for instance, to ascertain the presence or absence of the lentivirus, retrovirus, or immunodeficiency virus, e.g., feline immunodeficiency virus, in a sample such as sera or, to determine whether an immune response has elicited to the lentivirus, retrovirus, or immunodeficiency virus, e.g., FIV, or, to particular antigen(s) or epitope(s); or, in immunoadsorption chromatography. To generate DNA for use as hybridization probes or to prepare PCR primers or for DNA immunization. And, the inventive vectors or recombinants, expression products therefrom, and immunogens, antigens, and epitopes from the inventive vectors or recombinants can be used to generate stimulated cells which can be further used (reinfused) to stimulate an immune response (antigenic, or immunological response; or active immunization) or, to boost or stimulate the immune system (for instance, of an immunocompromised or seropositive animal or human). Other utilities also exist for embodiments of the invention.

A better understanding of the present invention and of its many advantages will be had from the following examples, given by way of illustration.

EXAMPLES

DNA Cloning and Synthesis. Plasmids were constructed, screened and grown by standard procedures (Maniatis et al., 1982; Perkus et al., 1985; Piccini et al., 1987). Restriction endonucleases were obtained from Bethesda Research Laboratories, Gaithersburg, Md., New England Biolabs, Beverly, Mass.; and Boehringer Mannheim Biochemicals, Indianapolis, Ind. Klenow fragment of E. coli polymerase was obtained from Boehringer Mannheim Biochemicals. BAL-31 exonuclease and phage T4 DNA ligase were obtained from New England Biolabs. The reagents were used as specified by the various suppliers.

Synthetic oligodeoxyribonucleotides were prepared on a Biosearch 8750 or Applied Biosystems 380B DNA synthesizer as previously described (Perkus et al., 1989). DNA sequencing was performed by the dideoxy-chain termination method (Sanger et al., 1977) using Sequenase (Tabor et al., 1987) as previously described (Guo et al., 1989). DNA amplification by polymerase chain reaction (PCR) for sequence verification (Engelke et al., 1988) was performed using custom synthesized oligonucleotide primers and GeneAmp DNA amplification Reagent Kit (Perkin Elmer Cetus, Norwalk, Conn.) in an automated Perkin Elmer Cetus DNA Thermal Cycler. Excess DNA sequences were deleted from plasmids by restriction endonuclease digestion followed by limited digestion by BAL-31 exonuclease and mutagenesis (Mandecki, 1986) using synthetic oligonucleotides.

Cells, Virus, and Transfection. The origins and conditions of cultivation of the Copenhagen strain of vaccinia virus has been previously described (Guo et al., 1989). Generation of recombinant virus by recombination, in situ hybridization of nitrocellulose filters and screening for B-galactosidase activity are as previously described (Piccini et al., 1987).

The origins and conditions of cultivation of the Copenhagen strain of vaccinia virus and NYVAC and ALVAC has been previously described (Guo et al., 1989; Tartaglia et al., 1992, U.S. Pat. Nos. 5,364,773 and 5,494,807). Generation of recombinant virus by recombination, in situ hybridization of nitrocellulose filters and screening for B-galactosidase activity are as previously described (Panicali et al., 1982; Perkus et al., 1989).

The parental canarypox virus (Rentschler strain) is a vaccinal strain for canaries. The ALVAC vaccine strain, as discussed above, was obtained from a wild type isolate and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination tests. The plaque purified canarypox isolate is designated ALVAC.

The strain of fowlpox virus (FPV) designated FP-1 has been described previously (Taylor et al., 1988a). It is an attenuated vaccine strain useful in vaccination of day old chickens. The parental virus strain Duvette was obtained in France as a fowlpox scab from a chicken. The virus was attenuated by approximately 50 serial passages in chicken embryonated eggs followed by 25 passages on chicken embryo fibroblast cells. The virus was subjected to four successive plaque purifications. One plaque isolate was further amplified in primary CEF cells and a stock virus, designated as TROVAC, established.

NYVAC, ALVAC and TROVAC viral vectors and their derivatives were propagated as described previously (Piccini et al., 1987; Taylor et al., 1988a,b, U.S. Pat. Nos. 5,364,773 and 5,494,807). Vero cells and chick embryo fibroblasts (CEF) were propagated as described previously (Taylor et al., 1988a,b).

Example 1

Construction of ALVAC-FIV Env

The feline immunodeficiency virus (FIV) env coding sequence in plasmid ptg6184 and FIV nucleotide sequences were obtained from Rhone Merieux (Lyon, France). The cDNA clone was derived from the Villefranche strain of FIV. The FIV env nucleotide sequence is shown in FIG. 2 (SEQ ID NO:1).

The FIV env coding sequence was placed under control of the modified early/late vaccinia virus H6 promoter (Perkus, et al., 1989). The FIV env coding sequence contains two $T_5NT$ sequence motifs which may provide for premature early transcription termination (Yuen and Moss, 1987). The $T_5NT$ sequences were modified, without altering the predicted amino acid coding sequence, by replacement with a PCR-derived fragment. TTTTTAT between positions 2059 and 2065 in FIG. 2 was changed to TTCTTAT; TTTTTCT between positions 2110 and 2116 was changed to TTCTTCT.

Two overlapping PCR fragments were derived from the ptg6184 template, yielding a fragment with altered $T_5NT$ sequences. A 585 bp PCR fragment was generated using oligonucleotide primers MM040 (SEQ ID NO:9) (5'-AAAT-TCTTATATACAGCTTTCGCTATGCAA-GAATTAGGATGTAATCAAAATCAATTCTTCT GCAAAATCCCTCCTGGGT-3') and MM042 (SEQ ID NO:10) (5'-CCCATCGAGTGCGGCTAC-3'). MM040 primes toward the 3'-most sequences of the env coding sequence (from position 2056, FIG. 2). MM042 primes from the env 3'-most sequences toward the 5'-most sequences. A second PCR primed with MM041 (SEQ ID NO:11) (5'GCA-GAAGAATTGATTTTGATTACATCCTAATTCTT GCAT-AGCGAAAGCTGTATATAAGAATTTTTCCATAGCTTC-3') and MM043 (SEQ ID NO:12) (5'AAGTTCTGGCAACCCATC-3') generated a 187 bp fragment. MM041 primes from position 2118 toward the 5'-most sequences of env and MM043 primes toward the 3'-most sequences of the env coding sequence from position 1931 (FIG. 2). The two PCR products were pooled, primed with MM043 and MM042, and digested with ScaI at FIV coding sequence position 2020 in FIG. 2 and EcoRI 3' of the env coding sequence. The resultant 564 bp ScaI-EcoRI PCR fragment contains the 3'-most sequences of the FIV env coding sequence with the altered $T_5NT$ motifs.

Plasmid ptg6184 was digested with EcoRI and partially digested with ScaI. This ptg6184 derived fragment with the 3' FIV env deleted from ScaI (FIG. 2 position 2020) through EcoRI 3' of the env coding sequence was ligated to the 564 bp ScaI-EcoRI PCR-derived fragment (above). The resultant plasmid pMM120 contains the FIV env with altered $T_5NT$ motifs. The nucleotide sequence was confirmed using standard procedures (Goebel et al., 1990a). The 2.6 kbp pMM120 PstI-EcoRI fragment, containing the FIV env coding sequence, was inserted between the pBS-SK (Stratagene, La Jolla, Calif.) PstI and EcoRI sites generating pMM122.

The modified early/late vaccinia virus H6 promoter (Perkus et al., 1989) was added to pMM122 by overlapping the H6 translation initiation codon with the FIV env translation initiation codon. A fragment containing the H6 promoted 5'-most sequences of the env coding sequence was generated by PCR using primers MM037 (SEQ ID NO:13) (5'ATCATCCTGCAGAAGCTTCCCGGGTTCTTTATTCTATACTT-3'), MM038 (SEQ ID NO:14) (5'-CTGCAAATCCTTCTGCCATTACGATACAAACTTAAC-3'), MM065 (SEQ ID NO:15) (5'-CGTTAAGTTTGTATCGTAATGGCAGAAGGATTTGCAGCC-3'), and MM036 (SEQ ID NO:16) (5'-CCTCTTGAATTTCGTTCC-3'). pMM108, containing H6 promoter sequences, was used as template for PCR with MM037 and MM038 creating a 166 bp fragment containing the H6 promoter and the 5'-most bp of the FIV env coding sequence. pMM122 was used as template for PCR with MM065 and MM036 to generate a 235 bp fragment with the 3' H6 promoter and 5' env end. The two PCR products were pooled, primed with MM036 and MM037, and the resultant fragment, containing the H6 promoter fused to the 5' most bp of the FIV env coding sequence, was digested with PstI and KpnI generating a 266 bp fragment. pMM122 was digested with PstI and partially digested with KpnI to remove the 5'-most sequences of the FIV env coding region and the 266 bp PstI-KpnI PCR-derived fragment described above was inserted. The resultant plasmid pMM125 contains the FIV env juxtaposed 3' to the vaccinia H6 promoter in pBS-SK (Stratagene, La Jolla, Calif.).

Sequence analysis of pMM125 demonstrated correct PCR construction of the H6 promoted FIV env 5'-most sequences, but frameshift mutations were observed 3' of the PCR insertion. The frameshifts were not observed in pMM122. All pMM125 clones contained frameshifts. These frameshifts were probably a result of the recently described instability of env sequences in high copy number plasmids (Wang and Mullins, 1995). Separate pMM125 clones had different frameshifts. An H6 promoted FIV env, without frameshifts, was constructed in the following manner.

Briefly, this is a summary of the following detailed description of the construction of an H6 promoted FIV env without frameshifts. The H6 promoted 5'-most sequences of the FIV env coding sequence, which did not contain frameshifts, from one pMM125 clone was ligated to the remaining unframeshifted 3'-most bp of FIV env end from another pMM125 clone. The first fragment was from the SmaI site 5' of the H6 promoter through the AflII site in the FIV env coding sequence (FIG. 1, position 1707). The second fragment was from the same AflII site to the SmaI site 3' of the env coding sequence. The ligation product was digested with SmaI, liberating three fragments. One fragment contained two 5'-most sequences and another fragment contained two 3'-most sequences. The third SmaI digestion product containing the H6 promoted FIV env expression cassette was isolated and inserted into a C6 vector, generating pRW945. To eliminate the possibility of frameshifts, pRW945 was not amplified in bacteria. Details of pRW945 construction follow.

One pMM125 clone, pMM125#11, had the correct sequence from SmaI 5' of the H6 promoter through the AflII site at position 1707 (FIG. 2); another pMM125 clone, pMM125#10, had the correct sequence from the AflII site at position 1707 through SmaI 3' of the env coding sequence. The 1.8 kbp pMM125#11 SmaI-AflII fragment, containing the H6 promoted 5'-most env sequences, was ligated to the 0.9 kbp pMM125#10 SmaI-partial AflII fragment containing the 3' portion of env. The ligation product was SmaI digested and the 2.7 kbp fragment was inserted into the C6 vector pMM117, yielding pRW945.

The C6 insertion plasmid, pMM117, was constructed in the following manner. A 3 kbp ALVAC HindIII clone was sequenced and an open reading frame was defined. A PCR-derived fragment was used for replacement of the open reading frame with restriction sites for DNA insertions. The PCR-derived fragment was generated with primers C6A1 (SEQ ID NO:17) (5'-ATCATCGAGCTCGCGGCCGCCTATCAAAAGTCTTAATGAGTT-3'), C6B1 (SEQ ID NO:18) (5'-GAATTCCTCGAGCTGCAGCCCGGGTTTTTATAGCTAATTAGTCAT TTTTCGTAAGTAAGTATTTTTATTTAA-3'), C6C1 (SEQ ID NO:19) (5'-CCCGGGCTGCAGCTCGAGGAATTCTTTTTATTGATTAACTAGT CAAATGAGTATATATAATTGA AAAAGTAA-3') and C6D1 (SEQ ID NO:20) (5'-GATGATGGTACCTTCAT-AAATACAAGTTTGATTAAACTTAAGTTG-3'). ALVAC was used as template for PCR using oligonucleotides C6A1 and C6B1 generating a 380 bp fragment. A second PCR reaction used ALVAC template and primers C6C1 and C6D1 to generate a 1155 bp fragment. The PCR reaction products were pooled and primed for a final PCR with C6A1 and C6D1 yielding a 1613 bp fragment. The final PCR product was digested with SacI and KpnI for insertion between the SacI and KpnI sites of pBS-SK (Stratagene, La Jolla, Calif.). The resultant C6 insertion plasmid was designated pC6L. The C6 insertion plasmid pMM117 was constructed by adding the sequence GGGGGATCCTTAATTAATTAGT-TATTAGACAAGGTGAAAACGAAAC-TATTTGTAGCTTAATTAAT TAGCTGCAGGAATTC (SEQ ID NO:21) between the pC6L (FIG. 4; SEQ ID NO:3) SmaI and EcoRI sites.

The above described plasmid pRW945 contains the H6 promoted FIV env coding sequence, with altered $T_5NT$ motifs, in a C6 insertion plasmid. pRW945 was used in in vitro recombination experiments with ALVAC as the rescuing virus to derive recombinant vCP242. FIG. 5 shows the predicted nucleotide sequence of the insertion in vCP242 (SEQ ID NO:4).

Example 2

Construction of Recombinant ALVAC Expressing FIV Gag, and Pro

The feline immunodeficiency virus (FIV) gag and pol coding sequences in plasmid ptg8133 and FIV env coding sequence in plasmid ptg6184 were obtained from Rhone Merieux (Lyon, France). The cDNA clones were derived from the Villefranche strain of FIV. FIG. 3 (SEQ ID NO:2) contains the nucleotide sequence for the FIV gag and pol coding regions obtained from Rhone Merieux.

The FIV gag sequences encoding core antigens, followed by the pol sequences encoding a protease, reverse transcriptase and integrase, were placed under control of the early/intermediate vaccinia I3L promoter (Schmitt, J. and Stunnenberg, H., 1988; Vos, J. and Stunnenberg, H., 1988). The I3L promoter corresponds to positions 65073 through 64971 in Goebel et al., 1990 a,b. The gag and pol coding sequences were engineered in a single transcription unit. The Gag and Pol open reading frames (ORFS) differ and translation of the Pol ORF results via a ribosomal frameshift mechanism (Morikawa and Bishop, 1992) as it does normally in FIV-infected cells.

PCR-derived fragments were used for construction of the I3L promoted FIV gag/pol cassette. The PCR-derived fragments were also used to alter a $T_5NT$ sequence motif which may provide for premature early transcription termination (Yuen and Moss, 1987). TTTTTAT between positions 467 and 473 (FIG. 3) was changed to TTTTCAT, without altering the predicted amino acid coding sequence. Manipulations to construct the I3L promoted FIV gag/pol expression cassette were performed in the following manner.

PCR was performed with ptg8133, containing the FIV gag/pol coding sequences, as template and MM027 (SEQ ID NO:22) (5'-CAAAAATGGTGTCCATTTTCATG-GAAAAGGCAAGAGAAGGAC-3') and MM028 (SEQ ID-NO:23) (5'-CTGCTGCAGTAAAATAGG-3') as primers to generate a 245 bp fragment. MM027 primed from position 452 (FIG. 3) toward the 3'-most sequences containing a nucleotide change in the $T_5NT$ sequence motif. MM028 primes from position 697 downstream of a HindIII site toward the gag 5'-most sequences. The 245 bp PCR-derived fragment contains the FIV gag coding sequence from position 452 to position 697 with an altered $T_5NT$ motif.

A second PCR using ptg8133 as template and primers MM029 (SEQ ID NO:24) (5'-CTTCTCTTGCCTTTTC-CATGAAAATGGACACCATTTT TGGGTC-3') and MM030 (SEQ ID NO:25) (5'-CAATTATTTAGGTTTAAT-CATGGGGAATGGACAGGGGC-3') generated a 508 bp fragment. MM029 primes from position 490 (FIG. 3) toward the 5'most sequences of the gag coding sequence and alters the $T_5NT$ sequence motif. MM030 contains the 3'-most sequence of the I3L promoter and primes from the gag initiation codon toward the 3'-most sequences of the gag coding sequence. The 508 bp PCR-derived fragment contains the 3'-most I3L promoter and the FIV gag coding sequence with an altered $T_5NT$ motif through position 490.

Plasmid template pMM100, containing the I3L promoter sequences, was primed with MM031 (SEQ ID NO:26) (5'-CGCCCCTGTCCATTCCCCATGATTAAAC-CTAAATAATTGTAC-3') and MM032 (SEQ ID NO:27) (5'-ATCATCGTCGACATCGATACATCATG-CAGTGGTTAAAC-3') to generate a 137 bp PCR-derived fragment. The MM031 5'-most sequences contains the 5'-most bp of gag followed by a sequence which primes at the I3L promoter 3'-most sequences toward the I3L promoter 5'-most sequences. MM032 has SalI and ClaI sites followed by a sequence which primes from the I3L promoter 5'-most sequences toward the 3'-most sequences. The 137 bp PCR-derived fragment contains the I3L promoted FIV gag 5'-most 20 bp.

The three PCR products were pooled and primed for PCR with MM032 and MM028. The resultant 814 bp fragment was digested with HindIII and SalI, generating a 726 bp fragment containing the I3L promoted FIV gag 5'-most sequences with an altered $T_5NT$ motif.

ptg8133 was digested with SacI and SalI, to remove the 7.2 kbp plasmid sequences, and the 4.7 kbp fragment was isolated and partially digested with HindIII. The 4 kbp ptg8133 SacI-HindIII partial digestion product, containing the FIV gag coding sequence from position 615 through the FIV pol coding sequence, was isolated.

SacI-SalI digested pBS-SK (Stratagene, La Jolla, California) was ligated with the 726 bp HindIII-SalI PCR-derived fragment (above) and the 4 kbp ptg8133 SacI-HindIII fragment. The resultant plasmid pMM116 contains the I3L promoted FIV gag/pol expression cassette in pBS-SK.

The 4.7 kbp pMM116 Asp718-Ecl136II fragment containing I3L promoted FIV gag/pol coding regions was treated with Klenow, in the presence of 20 mM dNTPs, and inserted into SmaI digested pMM117 to produce pMM121. pMM117 is the C6 insertion plasmid described above.

The 1.4 kbp pMM121 EcoRI fragment, containing the I3L promoted FIV gag/pol 5'-most region, was inserted into the pBS-SK (Stratagene, La Jolla, Calif.) EcoRI site generating pMM123. A PCR-derived fragment was used to remove the coding sequences corresponding to the carboxy-end of Pol to achieve Gag-protease expression only. The PCR-derived fragment introduced a termination codon following the protease coding sequence at position 1709 (FIG. 3). Manipulations to construct the I3L promoted FIV gag and protease coding sequences were performed in the following manner.

Template pMM121, containing the I3L promoted FIV gag/pol coding sequences, was primed with MM063 (SEQ ID NO:28) (5'-CAGGACATCTAGCAAGAC-3') and MM064 (SEQ ID NO:29) (5'-GATGATCCCGG-GATAAAAATTATTGAGCCATTACTAACCT-3') to gener ate a 580 bp PCR-derived fragment. MM063 primes from position 1148 (FIG. 3) toward the 3'-most sequences. MM064 primes from position 1709 toward the 5'-most sequences. The 580 bp PCR-derived fragment, Containing the FIV protease coding sequence with a stop codon at position 1709 (FIG. 3), was digested with EcoRI and SmaI yielding a 475 bp fragment.

pMM123 was linearized at the SmaI site 3' of the FIV insertion, followed by partial EcoRI digestion. The 475 bp SmaI-EcoRI PCR-derived fragment (above) was inserted into the pMM123 SmaI-EcoRI partial digestion product, with the EcoRI site digested at FIG. 3 position 1246. The resultant plasmid pMM127 contains the FIV gag and protease coding sequences, followed by a stop codon, in pBS-SK (Stratagene, La Jolla, Calif.). The nucleotide sequence of the PCR-derived fragment in pMM127 was confirmed using standard procedures (Goebel et al., 1990a). A single bp deletion 3' of the FIV protease coding sequence was observed. MM064 was designed to add TTTTTAT after the FIV protease stop codon. One T in the TTTTTAT sequence after the stop codon is missing from pMM127, resulting in the sequence TTTTAT.

The 1.8 kbp pMM127 BamHI-SmaI fragment, containing the I3L promoted FIV gag and protease coding sequences, was inserted into SmaI-BamHI partially digested pMM117. The C6 insertion plasmid pMM117 is described above. The BamHI partial digestion was used to digest the BamHI site next to the SmaI site in pMM117. The resultant plasmid, containing the I3L promoted FIV gag and protease coding sequences in a C6 insertion plasmid, was designated pMM129. Plasmid pMM129 was used in in vitro recombination experiments with ALVAC as the rescuing virus to derive recombinant vCP253. FIG. 6 (SEQ ID NO:5) shows the predicted nucleotide sequence of the I3L promoted FIV gag/protease expression cassette and flanking regions in vCP253.

Example 3

Construction of Recombinant ALVAC Expressing FIV Env, Gag, and Pro

Plasmid pMM125, containing the H6 promoted FIV env with frameshift mutations, is described above. A deliberate insertion, containing a frameshift, into the FIV env coding sequence allowed stable maintenance of the remainder of the H6 promoted FIV env construct in bacteria. After bacterial amplification the insertion was removed. Manipulations to construct the H6 promoted FIV env coding sequence, with a deliberate frameshift insertion, were performed in the following manner.

pMM125#11 (described above) was modified by insertion of a PCR-derived fragment which repaired the spontaneous frameshift and introduced a deliberate frameshift flanked by BstEII sites. The BstEII insertion is at position 1920 (FIG. 2). The insertion introduces a stop codon followed by a frameshift, NotI and HindIII sites. There are no BstEII sites in pMM125. The PCR-derived fragment also changes the A at position 1920 in FIG. 2 to C. The A to C change does not alter the predicted amino acid coding sequence, but the change does introduce a BstEII site. pMM125#10 has a spontaneous frameshift at position 1604 (FIG. 2). pMM125#10 was used as template for PCR with oligonucleotide primers RW542 (SEQ ID NO:30) (5'-TATGAATTG-TAATTGTAC-3') and RW545 (SEQ ID NO:31) (5'-GTAG-CATAAGGTTACCGCGGCCGCTAAGCTTAGGTTA CCATCCCTATAGCAGTA-3') to generate a 326 bp fragment containing the BstEII insertion. RW542 primes from position 1632 toward the FIV env 3'-most sequences; RW545 primes from position 1919 toward the FIV env 5'-most sequences (FIG. 2). pMM125#10 was used as template for PCR with RW544 (SEQ ID NO:32) (5'-GTAG-CATAAGGTAACCTAAGCTTAGCGGC-CGCGGTAACCCAATACCACCAAGTTCTGGC-3') and T3 (SEQ ID NO:33) (5'-ATTAACCCTCACTAAAG-3') generating a 791 bp fragment containing the BstEII insertion and the FIV env coding sequence 3'-most sequences. RW544 primes from position 1914 toward the env 3'-most sequences. T3 primes in the pBS-SK plasmid, downstream of the FIV env stop codon, toward the FIV env 5'-most sequences. The two PCR products were pooled, primed with RW542 and T3, and the resultant 1.1 Kbp product was digested with EcoRI and partially digested with AflII generating a 876 bp fragment which was inserted into the following pMM125#11 vector. The PCR-derived fragment and pMM125#11 vector were digested with AflII at position 1709 (FIG. 2). pMM125#11 was digested with EcoRI and EcoRI to remove the FIV env coding sequence 3'-most sequences which contained a spontaneous frameshift. The 876 bp EcoRI-AflII PCR-derived fragment was inserted into the pMM125#11 EcoRI-AflII vector. The resultant plasmid pMM134 contains the FIV env coding sequence juxtaposed 3' to the H6 promoter in pBS-SK (Stratagene, La Jolla, Calif.). pMM134 also contains a deliberate frameshift mutation inserted between two BstEII sites. The entire H6 promoted FIV env sequence in pMM134, including the BstEII insertion, was confirmed. As expected, the BstEII insertion allowed stable maintenance of the remainder of the H6 promoted FIV env construct.

Once the H6 promoted FIV env coding sequence from pMM134 is cloned into a poxvirus insertion plasmid, the BstEII insertion should be removed to allow expression of the full length FIV env coding sequence. The BstEII insertion is removed by BstEII digestion, followed by a dilute ligation reaction favoring intramolecular ligation. The intramolecular ligation product would contain the H6 promoted FIV env, without the BstEII insertion. After the BstEII insertion is removed, the H6 promoted FIV env coding sequence is not expected to be stably maintained in bacteria and the plasmid was not amplified in bacteria. After ligation, the plasmid was digested with NotI. Ligation products containing the BstEII insertion would be digested at the NotI site within the BstEII insertion. NotI digestion within the BstEII insertion would prevent the ability of the plasmid to generate a viable recombinant poxvirus. Full length FIV env, without the BstEII insertion, would not be cleaved by NotI digestion; FIV env coding sequences would remain intact.

Example 4

Construction of the H6 Promoted FIV Env Coding Sequence in C6 With the I3L Promoted FIV Gag and Protease Coding Sequences Construction of pMM134 containing the H6 promoted FIV env coding sequence with a BstEII insertion has been described above. The 2.7 kbp H6 promoted FIV env SmaI fragment from pMM134, with the BstEII insertion, was cloned into the following pMM129 insertion plasmid.

pMM129, containing the I3L promoted FIV gag and protease coding sequences in C6, has been described above. The pMM129 SalI site 5' of the I3L promoter was blunt ended with Klenow in the presence of 20 mM dNTPs.

PMM138 was constructed by insertion of the 2.7 kbp pMM134 SmaI fragment containing the H6 promoted FIV env coding sequence, with the BstEII insertion, into the pMM129 blunt ended SalI site. The H6 promoted FIV env coding sequence, in pMM138, is 5' of the I3L promoted FIV gag and protease coding sequences; the FIV coding sequences are transcribed in the same direction.

The two BstEII sites in pMM138 surround the insertion containing a frameshift. Digestion of pMM138 with BstEII, to remove the insertion, was followed by ligation. The resultant plasmid pMM146 was not amplified in bacteria. pMM146 was designed for NotI digestion before in vitro recombination experiments; NotI digestion served two purposes. First, any plasmid unintentionally containing the BstEII insertion would be digested with NotI within the insertion and the donor plasmid would be prevented from generating a viable ALVAC recombinant. Second, NotI linearizes pMM146 within the pBS-SK backbone for efficient generation of the intended ALVAC recombinant. pMM146 was digested with NotI prior to use in in vitro recombination experiments with ALVAC as the rescuing virus to derive recombinant vCP255. FIG. 7 (SEQ ID NO:6) shows the predicted nucleotide sequence of the H6 promoted FIV env/I3L promoted FIV gag/protease expression cassette and flanking regions in vCP255.

Example 5

Construction of Recombinant ALVAC Expressing FIV 97TM, Gag, and Pro

The FIV envelope glycoprotein is composed of two cleavage products, gp97 and gp40. The FIV env coding sequence was modified, by replacing gp40 with the transmembrane anchor domain from the FIV env coding sequences, in the following FIV 97TM construct. FIV 97TM, containing gp97 followed by the transmembrane anchor domain, was constructed in the following manner.

A PCR-derived fragment PCR-FIV1 (242 bp) was synthesized using pMM125#10 (containing the previously described FIV env with the correct sequence from AflII site to 3'-most sequences) as a template, and oligonucleotides MW196 (SEQ ID NO:34) (5'-ACTTGCCATCGT-CATGGGGG-3') and MW195A (SEQ ID NO:35) (5'-GATACCTCCCAATAGTCCCCTTTTCCT-TCTAGGTTTATATTC-3') as primers. PCR-derived fragment PCR-FIV2 (193 bp) was synthesized using pMM125#10 as a template, and oligonucleotides MW194A (SEQ ID NO:36) (5'-GAATATAAACCTAGAAG-GAAAAGGGGACTATTGGGAGGTATC-3') and MW197 (SEQ ID NO:37) (5'-ATCATCGAATTCATAAAAATCAT-TCTTCTCCTTCTACTTC-3') as primers. PCR-derived fragment PCR-FIV3 (393 bp) was synthesized using PCR-derived fragments PCR-FIV1 and PCR-FIV2 as templates, and oligonucleotides MW196 and MW197 as primers. A complete AflII/EcoRI digest of PCR-FIV3 was performed, and the 284 bp fragment was isolated. This fragment was ligated into the 4.8 kb AflII/EcoRI fragment of pMM125#11 (containing the previously described FIV env with the correct sequence from 5'-most sequences to the EcoRI site described above). The resultant plasmid, pMAW103, contains H6 promoted FIV 97TM.

A PstI site was added upstream of the H6 promoter in the following manner. PCR-derived fragment PCR-FIV4 (359 bp) was synthesized using pMAW103 as a template, and oligonucleotides MW209 (SEQ ID NO:8) (5'-ATCAT-CAAGCTTCTGCAGTTCTTTATTCTA TACTTA-3') and MM036 (SEQ ID NO:16) (5'-CCTCTTGAATTTCGTTCC-3') as primers. A complete HindIII/NruI digest of PCR-FIV4 was performed, and the 110 bp fragment was inserted into the 5.0 kb HindIII/NruI fragment of pMAW103, yielding plasmid pMAW103A. The 2126 bp pMAW103A PstI fragment containing the H6 promoted FIV 97TM was inserted into the PstI site of pMM117 (described above), yielding plasmid pMAW104.

The 2852 bp pMAW104 BamHI partial digestion product, containing H6 promoted FIV 97TM, was inserted into BamHI digested pMM129 (I3L promoted FIV gag and pro in C6 described above). The resultant plasmid pMAW105 contains H6 promoted FIV 97TM and I3L promoted FIV gag and pro in C6. Plasmid pMAW105 was used in in vitro recombination experiments with ALVAC as the rescuing virus to derive recombinant vCP329. FIG. 8 (SEQ ID NO:7) shows the predicted nucleotide sequence of the insertion to make vCP329.

Example 6

ALVAC FIV Recombinant Expression Analysis

Expression of the appropriate FIV-specific gene products encoded by the ALVAC recombinants vCP242, vCP253, vCP255, and vCP329 was demonstrated in various analyses. Expression analyses were performed using either appropriate monoclonal antibodies or serum derived from FIV seropositive cats. Either reagent worked equally well in confirming expression in ALVAC-FIV-infected cells. Accordingly, without undue experimentation, from seropositive individuals, monoclonals can be derived for confirming expression.

vCP242 FIV Env expression was demonstrated by ELISA (described below). vCP242 was positive for surface expression in an immunofluorescence assay by FACS with an FIV Env specific monoclonal antibody (obtained from Rhone-Merieux, Lyon, France). vCP242 was positive by immunoprecipitation using polyclonal serum from FIV infected cats and two different monoclonal antibodies (described below). Thus, without undue experimentation, monoclonals from seropositive individuals can be derived for confirming expression.

vCP253 was positive for internal expression of Gag by FACS. vCP253 was positive by immunoprecipitation for expression of the mature Gag p24. A dominant Gag precursor was detected at 37 kDa; additional signals, representing Gag cleavage products, were obtained at 49 kDa, 4okDa, and 32 kDa.

vCP255 surface expression for Env was positive by FACS with an Env-specific monoclonal antibody (described below). vCP255 internal expression of Gag was demonstrated with a Gag-specific monoclonal antibody by FACS. vCP255 was assayed by immunoprecipitation with monoclonal antibodies to each gene product: Gag was positive with signals at approximately 49 kDa, 40 kDa, 37 kDa, and 24 kDa; FIV Env expression was positive with signals at 130 kDa and 90 kDa.

vCP329 expression of 97TM and gag were detected by immunoprecipitation with pooled serum from FIV infected cats.

FACS ANALYSIS: vCP255 contains the feline immunodeficiency virus (FIV) env, gag and protease coding sequences in locus C6. pMM146 was used in in vitro recombination experiments with ALVAC as the rescuing virus to derive recombinant vCP255. vCP255 FIV-specific gene product expression was assayed on a fluorescence activated cell sorter (FACS). The FIV Env protein product was assayed on the surface of vCP255 infected cells. The FIV p24 product was assayed for using internal expression analyses. The antisera used for FACS analysis were:
1) monoclonal anti-FIV env: 128F10 EP110592 from Rhone Merieux (1:200 dilution)
2) monoclonal anti-FIV p24: pool 125A3, 314B5 EP072092 from Rhone Merieux (1:100 dilution)
3) monoclonal anti-rabies G: 24-3F-10 021387 from C. Trimarchi, Griffin Laboratories, New York State Health Department (1:200 dilution)
4) polyclonal goat anti-mouse IgG coupled to fluorescein isothiocyanate (FITC) from Boehringer Mannheim, catalogue number 605240, lot number 24064 (1:100 dilution)

FACS ANALYSIS OF EXPRESSION ON CELL SURFACE: $1 \times 10^7$ HeLa-S3 cells (ATCC #CCL2.2) were infected with $5 \times 10^7$ PFU of vCP255 in minimum essential medium (S-MEM: Gibco #380-2380AJ) supplemented with 10% fetal bovine sera, 20 mM Glutamine and 0.5% penicillin-streptomycin. The infected cells were incubated at 37° C. for 30 minutes with occasional agitation. The cells were washed with 10 mls S-MEM. After each wash the cells were pelleted at 1000 RPM for 5 minutes in a Beckman GPKR centrifuge. The infected cell pellet was resuspended in 1 ml S-MEM, transferred to a 5 ml Sarstadt tube and slowly rotated at 37° C. overnight.

After overnight incubation, 100 μl aliquots of the infected cells were added to 5 ml polypropylene tubes. The cells were washed with 3 mls of PBS-CMF (137 mM NaCl, 2.7 mM KCl, 1.5 mM $KH_2PO_4$, and 8 mM $Na_2HPO_4$; pH 7.4) which included 0.2% $NaN_3$ and 0.2 bovine serum albumen (BSA). The cells were pelleted and the supernatant was discarded. Specific antibody was added to one tube and nonspecific antibody (anti-rabies G) was added to a second tube in the following manner.

100 μl of antibody (previously preadsorbed with HeLa Cells) diluted in PBS-CMF supplemented with 0.2% $NaN_3$ and 0.2% BSA was added to each cell pellet, and incubated at 4° C. for 30 minutes. The cells were washed and pelleted twice in 3 mls of PBS-CMF containing 0.2% $NaN_3$ and 0.2% BSA. 100 μl of secondary FITC coupled antibody (previously preadsorbed with HeLa Cells) diluted 1:50 in PBS-CMF containing 0.2% $NaN_3$ and 0.2% BSA was added and incubated at 4° C., in the dark, for 30 minutes. The cells were washed and pelleted twice in 3 mls of PBS-CMF containing 0.2% $NaN_3$ and 0.2% BSA. The cell pellets were resuspended in 1 ml PBS-CMF, containing 0.2% $NaN_3$ and 0.2% BSA, transferred to 5 ml polystyrene tubes and assayed on the FACS.

FACSCAN ANALYSIS OF INTERNAL EXPRESSION: $1 \times 10^7$ HeLa-S3 cells (ATCC# CCL2.2) were infected with $5 \times 10^7$ PFU of UVCP255 in minimum essential medium (S-MEM: Gibco #380-2380AJ) supplemented with 10% fetal bovine serum, 20 mM Glutamine and 0.5% penicillin-streptomycin. The infected cells were incubated at 37° C. for 30 minutes with occasional agitation. The cells were washed with 10 mls S-MEM. After each wash the cells were pelleted at 1000 RPM for 5 minutes in a Beckman GPKR centrifuge. The infected cell pellet was resuspended in 1 ml S-MEM, transferred to a 5 ml Sarstadt tube and slowly rotated at 37° C. overnight.

After overnight incubation, 100 μl aliquots of the infected cells were added to 5 ml polypropylene tubes. The cells were washed with 3 mls PBS-CMF which contained 0.2% $NaN_3$. 100 μl of 4% paraformaldehyde (Polysciences Inc. #00380) pH 7.4 in PBS-CMF containing 0.2% $NaN_3$ was added to the cell pellet and incubated on ice for 10 minutes. Specific antibody was added to one tube and nonspecific antibody (anti-rabies G) was added to a second tube in the following manner.

The paraformaldehyde treated cells were washed with 3 mls PBS-CMF containing 0.2% $NaN_3$. Following the wash, 100 μl PBS-CMF containing 0.2% $NaN_3$, 1% saponin (SIGMA S-7900) and 20% heat inactivated newborn calf serum (Gibco #200-6010AJ) was added. The cells were incubated on ice for 30 minutes and washed with 3 mls PBS-CMF which contained 0.2% $NaN_3$.

100 μl of antibody (previously preadsorbed with HeLa Cells) diluted in PBS-CMF supplemented with 0.1% saponin and 20% heat inactivated newborn calf serum was added to each cell pellet, and incubated at 4° C. for 30 minutes. The cells were washed and pelleted twice in 3 mls of PBS-CMF containing 0.2% $NaN_3$ and 0.1% saponin.

100 μl of secondary antibody coupled to FITC (previously preadsorbed with HeLa Cells) diluted 1:50 in PBS-CMF-containing 0.2% $NaN_3$ and 0.1% saponin and 20% heat inactivated newborn calf serum was added and incubated at 4° C., in the dark, for 30 minutes. The cells were washed and pelleted twice in 3 mls of PBS-CMF containing 0.2% $NaN_3$ and 0.1% saponin. The cell pellets were resuspended in 1 ml PBS-CMF containing 0.2% $NaN_3$, transferred to 5 ml polystyrene tubes and assayed on the FACS.

vCP255 FACS ANALYSIS: Antisera/HeLa suspensions were assayed on a Becton Dickinson model FC FACScan flow cytometer. Data was analyzed on Lysis II Software (Becton Dickinson, UK). The antisera/HeLa suspensions were excited with a 488 nm argon laser, and FITC emission spectra was identified using FL-1 channel detectors. Ungated data was collected on 10,000 cells.

Fluorescence emission spectra, obtained by FACS analysis of ALVAC infected HeLa cells, demonstrated background levels of rabies G and FIV-specific gene products. Background levels of the rabies G glycoprotein were obtained by FACS analysis of vCP255 infected HeLa cells.

The fluorescence emission spectra of vCP255 infected HeLa cells, probed with FIV specific monoclonal antibodies, demonstrated expression of the FIV-specific gene products. The FIV p24 coding sequence product was detected internally from vCP255 infected HeLa cells. The FIV Env product was detected on the surface of vCP255 infected HeLa cells.

IMMUNOPRECIPITATION ANALYSIS: CEF or VERO cells were infected at an m.o.i. of 10 pfu/cell with ALVAC (the parental virus), vCP242, vCP253, vCP255 or vCP329. Following an hour adsorption period, the inoculum was removed and the cells were overlaid with 2 mls of modified Eagle's medium (minus cysteine and methionine) containing 2% dialyzed fetal bovine serum and [$^{35}$S]-TRANSlabel (New England Nuclear, Boston, Mass.; 30 uCi/ml). The lysates were harvested 18–24 hrs post-infection by addition of 1 ml 3× buffer A (450 mM NaCl, 3% NP-40, 30 mM Tris (pH7.4), 3 mMEDTA, 0.03% Na-azide, and 0.6 mg/ml PMSF) and analyzed for expression of FIV env and gag gene products. The above described polyclonal cat antisera or FIV-specific monoclonal antibodies were used for immunoprecipitation analysis in the following manner.

Lysates were incubated overnight at 4° C. with FIV-specific antisera-protein A-sepharose complexes. The samples were washed 4× with 1× buffer A and 2× with a $LiCl_2$/urea buffer (200 mM LiCl, 2M urea, and 10 mm Tris pH8.0). Precipitated proteins were dissociated from the immune complexes by addition of 2× Laemmli buffer (124 mM Tris (pH6.8), 4% SDS, 20% glycerol, 10% 2-mercaptoethanol) and boiling for 5 minutes. Proteins were fractionated on 10% SDS-polyacrylamide gels, fixed in methanol, and treated with 1M Na-salicylate for fluorography. Proteins of the appropriate size were precipitated from the lysates derived from cells infected with the ALVAC-FIV recombinants, but were not precipitated from uninfected or ALVAC infected cells. The results indicated appropriate expression of the FIV gene products by the ALVAC-FIV recombinants.

ELISA ANALYSIS: Primary chick embryo fibroblast (CEF) cells were infected with vCP219, vCP242, or ALVAC. The infected cells were analyzed with the following FIV-specific monoclonal antibodies (Rhone Merieux, Lyon, France).

| | |
|---|---|
| FIV gag: | 0126B4 (anti-P15) |
| | 314B5 (anti-P24) |
| | 125A3 (anti-p24) |
| FIV env: | 128F10 |
| | 117E5 |
| | 115G8 |

Serum Samples Tested by Elisa:
1. Serum from FIV-infected cats:
   Received from Rhone Merieux.
   Cats #34 and #103
2. Normal cat serum: Cat #1229 (Select Labs, Athens, Ga.).
3. Rabbit serum obtained from immunization with vCP65

| (ALVAC-RG): | |
|---|---|
| Rabbit A039: | prebleed |
| | week 14 |

Infected cell lysates were prepared in the following manner. Roller bottles of CEF cells were infected with ALVAC, vCP219, or vCP242 at an MOI of 5 PFU per cell in serum-free medium. Each roller bottle was harvested at 20 hours post infection, when the cells were completely round but not detached. Harvest consisted of pouring off the medium, washing once with PBS, and scraping the cells in 3 ml of PBS supplemented with aprotinin (3.6 T.I.U; Sigma #A-6279). The harvested cells were sonicated for four minutes on ice, and then centrifuged for 10 min at 1000 xg. Supernates were recovered and the protein concentration was approximately 7 mg/ml for each preparation.

A kinetic ELISA was performed in the following manner. Serum samples (above) were assayed by a sandwich kinetic ELISA for the detection of FIV env and gag gene products. Microtiter plates were coated with the pooled monoclonal antibodies, listed above, specific for either FIV env or FIV gag, at 2 or 5 µg/well. Infected cell lysates were applied at 0.2, 1, or 5 µg/well, for capture by the monoclonals. Each serum sample was assayed in triplicate at a dilution of 1:100. Antibody was detected with a 1:200 dilution of horse radish peroxidase(HRP)-conjugated anti-cat serum (Jackson Immuno Research cat# 102-035-003) or HRP-conjugated anti-rabbit serum (DAKO, cat# P217), followed by HRP substrate, o-phenylenediamine dihydrochloride(OPD). The optical densities at $A_{450}$ were read for 15 min and rates for each sample were calculated as mOD per minute.

Results from these ELISAs clearly demonstrated that FIV Env and Gag expression were detected with serum from FIV infected cats, but not normal cat serum (data not shown). Env was demonstrated with plates prepared using Env-specific MAb and lysates derived from cells infected with vCP242, and not with lysates from ALVAC or vCP219 infected cells. Similarly, Gag was demonstrated with plates prepared using Gag-specific MAb and lysates from cells infected with vCP219, and not ALVAC or vCP242 infected cells.

TABLE 1

DETECTION OF FIV ENV EXPRESSION BY KINETIC ELISA

| lysate conc | ALVAC lysate[a] | | env lysate | | gag lysate | |
|---|---|---|---|---|---|---|
| (µg/well) | | | KELISA (mOD/min) | | | |
| CAT SERUM:[b] | NCS | FIV | NCS | FIV | NCS | FIV |
| 0.2 | 1.3 | 5.2 | 1.2 | 5.1 | 1.2 | 3.5 |
| 1 | 1.7 | 5.0 | 1.4 | 11.3 | 1.7 | 4.9 |
| 5 | 2.2 | 5.4 | 1.6 | 22.0 | 2.0 | 5.0 |
| RABBIT SERUM:[c] | PB | Wk 14 | PB | Wk 14 | PB | Wk 14 |
| 0.2 | 1.3 | 4.8 | 0.9 | 2.3 | 0.9 | 2.8 |
| 1 | 1.0 | 5.0 | 0.7 | 4.1 | 0.8 | 3.0 |
| 5 | 1.1 | 6.4 | 0.9 | 3.0 | 1.0 | 4.6 |

[a]Cell lysates from CEF cells infected with ALVAC, ALVAC-FIV env, or ALVAC-FIV gag were applied at 0.2, 1, or 5 µg/well to wells previously coated with 2 µg/well of pooled FIV env-specific MAb.
[b]Cat sera: normal cat (NCS), FIV-infected cats (FIV).
[c]Rabbit sera: prebleed (PB) and week 14 serum from rabbits inoculated with vCP-65 (NYVAC-RG).

TABLE 2

DETECTION OF FIV GAG-SPECIFIC ANTIBODIES BY KINETIC ELISA

| lysate conc | ALVAC lysate[a] | | env lysate | | gag lysate | |
|---|---|---|---|---|---|---|
| (µg/ml) | | | KELISA (mOD/min) | | | |
| CAT SERUM[b] | NCS | FIV | NCS | FIV | NCS | FIV |
| 0.2 | 2.7 | 6.7 | 1.5 | 3.9 | 1.4 | 10.4 |
| 1 | 2.3 | 6.2 | 1.8 | 3.6 | 1.3 | 30.7 |
| 5 | 2.7 | 6.5 | 1.9 | 4.3 | 1.7 | 32.2 |
| RABBIT SERUM[c] | PB | wk 14 | PB | wk 14 | PB | wk 14 |
| 0.2 | 1.3 | 5.1 | 1.0 | 4.0 | 1.3 | 4.4 |
| 1 | 1.1 | 6.0 | 1.2 | 4.0 | 1.2 | 4.1 |
| 5 | 1.2 | 6.6 | 1.0 | 4.3 | 1.0 | 4.4 |

[a]Cell lysates from CEF cells infected with ALVAC, ALVAC-FIV env, or ALVAC-FIV gag were applied at 0.2, 1, or 5 µg/well to wells previously coated with 2 µg/well of pooled FIV gag-specific MAb.
[b]Cat sera: normal cat (NCS), FIV-infected cats (FIV).
[c]Rabbit sera: prebleed (PB) and week 14 serum from rabbits inoculated with vCP-65 (NYVAC-RG).

Example 7

Efficacy of ALVAC-FIV Recombinants in Cats

Grouping And Immunization: A total of 36 SPF animals purchased from Liberty (Waverly, N.Y.), age 12 weeks, were divided into seven groups as follows:

| Groups A | Group B | Group C | Group D | Group E | Group F | Group G |
|---|---|---|---|---|---|---|
| QH4 F | QH5 F | QQ1 F | QQ2 M | QH2 M | QH3 M | QC5 F |
| PY1 M | PY3 M | QA5 F | PY5 F | PY2 M | PY4 M | QG4 F |
| OO1 F | QS4 F | QU2 F | QO2 F | QA4 F | QA6 F | QE4 M |
| QC1 M | QC3 M | QX3 M | QX4 M | QC4 M | | |
| QU1 M | QG3 F | QI1 M | QI2 M | QG5 F | | |
| QL2 F | QE2 M | QL3 F | QL4 M | QE3 F | | |

Immunizations were administered as follows:

| | Immunization (Days) |
|---|---|
| Group A (6 cats) | |
| Primary immunization: ALVAC-env (vCP242) | Day 0 |
| Secondary immunization: ALVAC-env | Day 28 |
| Tertiary immunization: ALVAC-env | Day 56 |
| Group B (6 cats) | |
| Primary immunization: ALVAC-env, gag/pro (vCP255) | Day 0 |
| Secondary immunization: ALVAC-env, gag/pro | Day 28 |
| Tertiary immunization: ALVAC-env, gag/pro | Day 56 |
| Group C (6 cats) | |
| Primary immunization: ALVAC-gag/pro (vCP253) | Day 0 |
| Secondary immunization: ALVAC-gag/pro | Day 28 |
| Tertiary immunization: ALVAC-gag/pro | Day 56 |
| Group D (6 cats) | |
| Primary immunization: ALVAC-97TM gag/pro (vCP329) | Day 0 |
| Secondary immunization: ALVAC-97TM gag/pro | Day 28 |
| Tertiary immunization: ALVAC-97TM gag/pro | Day 56 |
| Group E (6 cats/control) | |
| Primary immunization: ALVAC (CPpp) | Day 0 |
| Secondary immunization: ALVAC | Day 28 |
| Tertiary immunization: ALVAC | Day 56 |
| Group F (3 cats/boost) | |
| Primary immunization: ALVAC-env, gag/pro (vCP255) | Day 0 |
| Secondary immunization: ALVAC-env, gag/pro | Day 28 |
| Boost: Inactivated FIV cell vaccine (ICV) | Day 56 |
| Group G (3 cats/control) | |
| Primary immunization: ALVAC | Day 0 |
| Secondary immunization: ALVAC | Day 28 |
| Boost: Inactivated FIV cell vaccine | Day 56 |

All cats received $1 \times 10^8$ PFU of the respective ALVAC recombinant in 1 ml sterile PBS via the intramuscular route. The ICV boost consisted of $2.5 \times 10^7$ fixed allogenic FIV-Petaluma infected feline T-cells (Fl-4 cell line), mixed with 250 μg muramyl dipeptide (Hosie et al., 1995). The ICV boost was given subcutaneously.

Challenge: All cats were challenged via an intraperitoneal (IP) administration 4 weeks following final immunization with 50 $CID_{50}$ of FIV-Petaluma (cell free supernatant derived from PBMC cultures infected with FIV Petaloma strain).

The following assays were performed to determine the FIV-specific virological status of the challenged animals. This provided a direct measurement of the protective efficacy of the ALVAC-based FIV vaccine candidates.

1) Virus Isolation: Detection of Infectious FIV by RT Assay. Peripheral blood mononuclear cells (PBMCs), bone marrow (BM) cells, and lymph node (LN) cells were collected upon challenge for virus isolation (Yamamoto et al., 1991, 1993; Okada et al., 1994). Virus isolation was performed by monitoring reverse transcriptase (RT) activity of culture supernatants. Isolated cells were cultured in the presence of IL-2 for 4 weeks. One-ml aliquots by standard procedures for $Mg^{++}$-dependent RT activity (specific for lentiviruses).

2) FIV-specific PCR. Proviral sequence detection was performed on DNA extracted from PBMC, BM, and LN cells. As a means of increasing the sensitivity, four consensus primer sets were used to amplify either env- or gag-specific coding regions, respectively (Yamamoto et al., 1991; Okada et al., 1994).

Following the initial PCR amplification, 1/25th of the product was re-amplified with the nested primer pair.

The results of the virological assays for samples pre- and post-challenge are presented in Tables 3 and 4. None of the cats demonstrated FIV viremia prior to challenge assessed either by RT determination or by the FIV-specific PCR analysis (Table 3). By 8 weeks post-challenge 4 of the 6 cats immunized with three doses of the ALVAC parental virus developed a persistent FIV-specific viremia (Table 3). Infection of these cats was also demonstrable by virus isolation and PCR in tissue samples taken post-challenge and by apparent FIV-specific seroconversion post-challenge (Table 4 and 5). No clear indications of infection were observed in the other two cats (QA4 and QE3) in the control group. Further, in comparison to this control group, no significant differences in efficacy were observed in groups of cats receiving three inoculations ($10^8$ pfu/dose) of ALVAC-FIV env (vCP242), ALVAC-FIV env/gag-pr (vCP255), or ALVAC-FIV 97TMG (vCP329).

Significantly, three administrations of ALVAC-FIV qag-pr(vCP253) afforded complete protection against FIV challenge exposure. Protection from infection was clearly evident in six of six cats throughout the 29 week post-challenge observation period by virus isolation and FIV-specific PCR in the periphery and lymphoid tissue (Table 3 and 4). Further, these cats also did not seroconvert relative to FIV seroreactivity by Western blot or ELISA (Table 4 and 5). To further substantiate the efficacy of vCP253, cells (PBMCS, lymph node, and bone marrow) from two animals in this group were transferred to SPF kittens. These cats have thus far tested negative by virus isolation (RT and PCR) and FIV-specific Western blot, whereas an SPF cats receiving similar cells from an infected control cat (Py2) clearly was positive for infection by these criteria.

Collectively, these results show that the Gag-pr is sufficient to protect against a lentivirus challenge exposure. As shown in Table 6, these results are indeed statistically significant. The results also show that the presence of Env may actually interfere with the establishment of a protective immune response. Further, the data for the experimental arm where cats received vCP255 (2×) followed by ICV immunogen illustrated that any impairment of Env can be overcome by such a prime/boost regimen (Table 3 and 4). Clearly the priming activity contributed by vCP255 was useful for protection, since the cats in the group receiving 2 administrations of ALVAC parental virus followed by ICV were readily infected upon challenge exposure (Table 3 and 4).

In short, this data provides for the first time protection against FIV infection in cats using a subunit immunogen, including only the FIV Gag-pr. In fact, the presence of Env may have reduced efficacy.

The importance of such data is also apparent in general for lentivirus vaccine development. Protection using solely the a Gag-pr provides several important elements to vaccine and diagnostic design. First, one can readily employ existing Env-based assays to discriminate vaccinated versus infected individuals. Secondly, the Gag-pr appears less variable than the Env species between lentivirus isolates and thus may serve for provision of cross-protective responses.

TABLE 3

Virus isolation (Reverse Transcriptase assay and PCR on PBMC)

| Vaccine | Cat no. | Pre | | Post challenge | | | | | | | |
|---|---|---|---|---|---|---|---|---|---|---|---|
| | | | | 4 weeks | | 8 week | | 12 weeks | | 17 weeks | |
| | | RT | PCR | RT | PCR | RT | PCT | RT | PCT | RT | PCT |
| ALVAC-Env | QH4 | − | − | − | − | − | − | − | − | − | − |
| | PY1 | − | − | + | + | + | + | + | + | + | + |
| | QO1 | − | − | + | + | + | + | T | T | | |
| | QC1 | − | − | − | − | − | − | − | − | − | − |
| | QU1 | − | − | − | − | − | − | − | − | − | − |
| | QL2 | − | − | + | + | + | + | + | + | + | + |
| ALVAC-Eng, gag/prot | QH5 | − | − | − | − | − | − | − | − | − | − |
| | PY3 | − | − | − | − | − | − | − | − | − | − |
| | QS4 | − | − | + | + | + | + | + | + | + | + |
| | QC3 | − | − | − | − | − | − | − | − | − | − |
| | QG3 | − | − | − | − | − | − | − | − | − | − |
| | QE2 | − | − | − | − | − | − | + | + | − | + |
| ALVAC-gag/prot | QQ1 | − | − | − | − | − | − | − | − | − | − |
| | QA5 | − | − | − | − | − | − | − | − | − | − |
| | QU2 | − | − | − | − | − | − | − | − | − | − |
| | QX3 | − | − | − | − | − | − | − | − | − | − |
| | QI1 | − | − | − | − | − | − | − | − | − | − |
| | QL3 | − | − | − | − | − | − | − | − | − | − |
| ALVAC-97TM of gag/prot | QQ2 | − | − | − | − | − | − | − | − | − | − |
| | PY5 | − | − | − | − | − | − | − | − | − | − |
| | QO2 | − | − | + | + | + | + | T* | T* | | |
| | QX4 | − | − | + | + | + | + | + | + | − | − |
| | QI2 | − | − | − | + | + | + | + | + | + | + |
| | QL4 | − | − | − | − | − | − | − | − | − | − |
| ALVAC-control | QH2 | − | − | + | + | + | + | T* | | | |
| | PY2 | − | − | − | − | + | + | + | + | + | + |
| | QA4 | − | − | − | − | − | − | − | − | − | − |
| | QC4 | − | − | − | − | + | + | + | + | + | + |
| | QG5 | − | − | + | + | + | + | T* | | | |
| | QE3 | − | − | − | − | − | − | − | − | − | − |
| ALVAC-env, gag, prot & ICV | QH3 | − | − | − | − | − | − | − | − | − | − |
| | PY4 | − | − | − | − | − | − | − | − | − | − |
| | QA6 | − | − | − | − | − | − | − | − | − | − |
| ALVAC-control & ICV | QC5 | − | − | + | + | + | + | + | + | T* | |
| | QG4 | − | − | + | + | + | + | + | + | T* | |
| | QE4 | − | − | − | − | + | + | + | + | + | + |

*T: Animal was euthanized.
ND: Not Determined

TABLE 4

FINAL VIRUS ISOLATION ON PBMC and TISSUE SAMPLES

TISSUE SAMPLE

| Vaccine | Cat no. | PBL | | LN | | BM | | THY | | WB | Elisa | Tissues taken at x weeks post-chall. |
|---|---|---|---|---|---|---|---|---|---|---|---|---|
| | | RT | PCR | RT | PCR | RT | PCR | RT | PCR | | | |
| ALVAC-Env | QH4 | − | "+" | − | "+" | − | "+" | − | − | − | − | 27 |
| | PY1 | − | − | − | + | − | − | + | + | + | + | 24 |
| | QO1 | + | + | + | + | + | + | ND | ND | + | + | 10 |
| | QC1 | − | − | − | − | − | − | ND | ND | − | − | 28 |
| | QU1 | − | − | − | − | − | − | ND | ND | − | − | 28 |
| | QL2 | − | − | + | + | + | + | − | − | + | + | 24 |
| ALVAC-Env, gag/prot | QH5 | − | − | − | − | − | − | − | − | ND | − | 28 |
| | PY3 | − | − | − | − | − | − | ND | ND | − | − | 27 |
| | QS4 | − | − | + | + | − | + | − | − | + | + | 24 |
| | QC3 | − | − | − | − | − | − | − | − | − | − | 28 |
| | QG3 | − | − | − | − | − | − | − | − | − | − | 28 |
| | QE2 | − | "+" | − | + | − | + | − | "+" | + | + | 28 |
| ALVAC-gag/prot | QQ1 | − | − | − | − | − | − | ND | ND | − | − | 29 |
| | QA5 | − | − | − | − | − | − | ND | ND | − | − | 29 |
| | QU2 | − | − | − | − | − | − | ND | ND | − | − | 29 |
| | QX3 | − | − | − | − | − | − | ND | ND | − | − | 29 |

TABLE 4-continued

FINAL VIRUS ISOLATION ON PBMC and TISSUE SAMPLES

TISSUE SAMPLE

| Vaccine | Cat no. | PBL RT | PCR | LN RT | PCR | BM RT | PCR | THY RT | PCR | WB | Elisa | Tissues taken at x weeks post-chall. |
|---|---|---|---|---|---|---|---|---|---|---|---|---|
| | QI1 | − | − | − | − | − | − | ND | ND | − | − | 29 |
| | QL3 | − | − | − | − | − | − | ND | ND | − | − | 29 |
| ALVAC-97TM OF gag/prot | QQ2 | − | − | − | + | − | − | − | − | − | − | 27 |
| | PY5 | − | − | − | − | − | − | − | − | − | + | 28 |
| | QO2 | + | + | + | + | + | + | ND | ND | + | + | 10 |
| | QX4 | − | − | − | − | − | − | − | − | + | −/+ | 25 |
| | QI2 | − | − | − | − | − | − | − | − | + | − | 25 |
| | QL4 | − | − | − | − | − | − | − | − | ND | − | 27 |
| ALVAC control | QH2 | + | + | + | + | + | + | ND | ND | + | −/+ | 10 |
| | PY2 | + | + | − | − | − | + | ND | ND | + | − | 39 |
| | QA4 | − | − | − | − | − | − | − | − | − | − | 28 |
| | QC4 | + | + | + | + | + | + | + | + | + | + | 26 |
| | QG5 | − | + | + | + | − | + | ND | ND | + | + | 10 |
| | QE3 | − | − | − | − | − | − | − | − | − | − | 28 |
| ALVAC-Env/gag/ prot & ICV | QH3 | − | − | − | − | − | − | ND | ND | + | − | 36 |
| | PY4 | − | − | − | − | − | − | ND | ND | + | − | 36 |
| | QA6 | − | − | − | − | − | − | ND | ND | + | − | 36 |
| ALVAC-control & ICV | QC5 | + | + | + | + | − | − | ND | ND | + | + | 10 |
| | QG4 | − | + | + | + | − | + | ND | ND | + | + | 10 |
| | QE4 | + | + | ND | ND | + | + | ND | ND | + | + | 39 |

*T: Animal was euthanized.
ND: Not Determined
"+": Show only very faintly positive by PCR.
NOTE Westernblot: serum dilution 1:100
ELISA: serum dilution 1:200, Transmembrane peptide used: QELGCNQNQFFCK1

Example 8

ALVAC-FIV Recombinants Induce Protective Immunity Against Multiple Subtype FIV Challenge in Cats Materials and Methods Animals: Specific pathogen free (SPF), were purchased from Liberty Research, Inc.

Vaccine preparation: Canarypoxvirus (ALVAC)-FIV recombinants were generated as described above (vCP255). The ALVAC vCP255 vaccine was prepared from a serum free lysate of infected CEF. ALVAC vCP255 immunizations were given at $1\times10^8$ PFU intramuscularly. The inactivated cell vaccine (ICV) consisted of $2\times10^8$ paraformaldehyde inactivated Fl-4 cells (a feline lymphoid cell line chronically infected with FIV Petaluma) mixed with 250 µg SAF/MDP adjuvant (Hoise et al., 1995) and was given subcutaneously.

Grouping and immunization protocol: The challenge study involved 6 cats; the ALVAC-env,gag/pro/ICV immunized group (#PY4, #QH3, #QA6) which received the FIV Petaluma challenge described in Example 7 and a control group of three age matched SPF cats (#EJ2, #DH3, #GU5) which had received no immunizations prior to the FIV Bangston challenge. (See Tables 5).

Challenge: The second challenge inoculum consisted of 75 $ID_{50}$ cell free FIV Bangston (subtype B) and was given 8 months after the initial FIV Petaluma challenge (See Example 7).

Immunogenicity monitoring: The induction of FIV specific antibody responses were determined by Western blot ting (immunoblot). Viral neutralizing antibody responses (VNA) were determined using previously described assays (Yamamoto et al., 1991).

Viral infectivity monitoring: Viral infection was monitored by several methods. This included assessment of viral reverse transcriptase activity in PBMC, bone marrow and lymph node cells taken at various times post-challenge by previously described methods (Yamamoto et al., 1991). In addition, pro-viral DNA (latent infection) was monitored by polymerase chain reaction (PCR) using FIV-env primers on DNA extracted from PBMC, bone marrow and lymph node cells upon culturing for RT activity Yamamoto et al., 1991; Okada et al, 1994). Further, FIV reinfection was determined by monitoring and comparing the character of FIV-specific humoral responses and viral neutralizing (VN) antibody responses in serum taken before and after challenge.

Results and Discussion

The immunogenicity and the protective efficacy of ALVAC prime/boost protocols was evaluated against experimental challenge with a distinctly heterologous FIV isolate (Bangston strain). First, the protective efficacy of immunizing with ALVAC-env,gag/pol alone was compared to priming with ALVAC-env,gag/pol followed by boosting with inactivated FIV-infected cell vaccine (ICV). All cats received a total of three immunizations and were challenged 4 weeks after the final immunization with cell free 50 $ID_{50}$ of FIV Petaluma (See Example 7). The FIV Petaluma isolate, like the FIV Villefranche isolate used to generate the ALVAC-FIV recombinant vaccine, is classified as a subtype A virus and differs from FIV Villefranche 3% in the Env and 1% in the Gag amino-acid coding region.

It was then evaluated whether the ALVAC-env,gag/pro/ICV immunized cats (#QA6, #QH3, #PY4) which resisted the FIV Petaluma challenge described in Example 7, could be protected from a second challenge with a distinctly heterologous FIV isolate of another subtype. The second challenge consisted of 75 $ID_{50}$ cell free FIV Bangston (PBMC derived) and was given at eight months after the initial challenge without any intervening booster. FIV Bangston is a subtype B late and differs from FIV Petaluma (subtype A) by 21% in the envelope glycoprotein amino acid coding region. Three age matched SPF cats (#EJ2, #GU5, #DH3) served as control cats for the FIV Bangston challenge. As presented in Table 7, all control cats became readily infected upon challenge. In contrast, ALVAC-env, gag/pro/ICV immunized cats #QH3 and #QA6 remained virus negative as determined by virus isolation (RT) and PCR of peripheral blood up to three months post-challenge. Cat #PY4 remained virus negative as determined by virus isolation (RT) of peripheral blood but tested positive by PCR at three months post-challenge. Nucleotide sequence analysis of the PCR product revealed FIV Bangston specific sequences. Thus ALVAC-env,gag/pro/ICV immunized cats were partially protected from a heterologous subtype FIV challenge. It is clear that these cats demonstrated, at least, a delay in infection as all control cats became viremic by 6 weeks post-challenge and only one of three ALVAC-env, gag/pol/ICV immunized cats became positive based on PCR analysis at 12 weeks post-challenge. This shows a potential utility for recombinants expressing Env.

In summary, prime/boost protocols involving priming with ALVAC recombinants followed by boosting with inactivated FIV-infected cell vaccines can elicit protective immunity against experimental challenge with heterologous FIV strains. This immunity is long lasting and also provides partial protection against distinctly heterologous FIV-strains of other subtypes. The data supports a role for cell mediated rather than viral neutralizing antibody responses and FIV-specific antibody responses. These findings are relevant not only to the development of multiple subtype FIV-vaccines but also to the development of effective multiple subtype HIV vaccines (as well as multiple subtype vaccines for other lentiviruses and other retroviruses) as new subtypes continue to arise and existing subtypes increasingly spread to new geographical areas.

A Fisher's exact test was performed. This is a modification of the Chi square test. This test should be used when comparing two sets of discontinuous, quantal (all or none) data. The analysis was set up as follows:

|  | Vaccinated | Unvaccinated |
|---|---|---|
| Infected | A | B |
| Uninfected | C | D |

For a single tailed probability the P value is calculated as:

$$P(\text{probability}) = (A+B)!(C+D)!(A+C)!(B+D)! / N!A!B!C!D!$$

Each group was compared to the ALVAC-control group (n=6) and to the ALVAC-control group +ALVAC-control&ICV group (n=9). A P value equal or less than 0.05 was considered significant.

TABLE 5

Viral neutralizing antibody titers upon immunization.

| | | | | VN titer | |
|---|---|---|---|---|---|
| | | | | | post-challenge |
| Vaccine | Cat ID# | pre- | post-immunizations | 3 mo. | 12 mo. |
| Alvac-env | QU1 | <5 | <5 | <5 | |
| | PY1 | <5 | <5 | >100 | |
| Alvac-gag/prot | QX3 | <5 | <5 | <5 | <5 |
| | QQ1 | <5 | <5 | <5 | <5 |
| | QI1 | <5 | <5 | <5 | <5 |
| | QL3 | <5 | <5 | <5 | <5 |
| Alvac-env, gag/prot | QS4 | <5 | <5 | >100 | |
| | PY3 | <5 | <5 | <5 | |
| Alvac-env, gag/prot &ICV | QH3 | <5 | <5 | 5–20 | <5 |
| | QA3 | <5 | <5 | 5–20 | <5 |
| | PY4 | <5 | <5 | 5–20 | 5–20 |
| ALVAC-control | QC4 | <5 | <5 | >100 | ND[a] |
| | PY4 | <5 | <5 | >100 | |
| | QA4 | in prep | | | |
| | QE3 | in prep | | | |
| ALVAC-control &ICV | QG4 | <5 | <5 | >100 | ND |
| | QC5 | <5 | <5 | >100 | |
| | QE4 | <5 | <5 | >100 | |

[a]ND—Not Determined

TABLE 6

Statistical significance of efficacy data.

| | viral status | | | |
|---|---|---|---|---|
| vaccine | vaccine group +/− | control group +/− (control) | P value (Single-tailed) | significant |
| Alvac-env | 3/3 | 4/2 | 0.5 | no |
| | | 7/2 | 0.28 | no |
| Alvac-gag/prot | 0/6 | 4/2 | 0.0303 | yes |
| | | 7/2 | 0.00914 | yes |
| Alvac-env, gag/prot | 2/4 | 4/2 | 0.28 | no |
| | | 7/2 | 0.118 | no |
| Alvac-97TMG | 3/3 | 4/2 | 0.5 | no |
| | | 7/2 | 0.28 | no |
| Alvac-env, gag/prot IWC | 0/3 | 3/0 | 0.05 | yes |
| | 0/3 | 7/2 | 0.00914 | yes |
| All groups combined | 8/19 | 7/2 | 0.0158 | yes |

TABLE 7

Parameters pre- and post-secondary challenge (FIV Bangston)

| | pre 2nd challenge WB titer | VN pre 2nd challenge[a] | | VN post 2nd challenge[b] | | post 2nd challenge[b] | | Protection Rate |
|---|---|---|---|---|---|---|---|---|
| | | FIVpet titer | FIVbang titer | FIVpet titer | FIVbang titer | WB titer | virus status RT/PCR | |
| QA6 | + (4–5) | <5 | ND | >5 | ND | + (3–4) | –/– | |
| QH3 | + (4) | <5 | ND | >5 | ND | + (3) | –/– | 2/3 |
| PY4 | + (4–5) | 5–20 | ND | >5 | ND | + (3–4) | –/+ | |
| GU5 | 0 (<2) | <5 | <5 | ND | ND | + (4–5) | +/+ | |
| DH3 | 0 (<2) | <5 | <5 | ND | ND | + (5) | +/+ | 0/3 |
| EJ2 | 0 (<2) | <5 | <5 | ND | ND | + (4) | +/+ | |

[a]Serum sample taken 8 months post challenge, at the day of 2nd challenge.
[b]Serum taken 4 months post 2nd-challenge.
[c]ND—Not Determined.

Example 9

Generation of Additional NYVAC & TROVAC Recombinants

Using the strategies outlined above for generating FIV coding DNA linked to a promoter, flanking DNA for NYVAC and TROVAC for insertion into regions of these vectors, analogous to embodiments in U.S. Pat. No. 5,494,807 and U.S. Ser. No. 08/417,210, are employed to generate NYVAC and TROVAC FIV recombinants. Analysis demonstrates incorporation into the vectors of the exogenous DNA and of expression thereof. Such additional recombinants are useful in the same manner as the above-described ALVAC embodiments.

Example 10

Generation of Additional Lentivirus and Additional Vector System Recombinants Using the strategies analogous to those outlined above for generating FIV coding DNA linked to a promoter and the strategies for generating alternative poxvirus, baculovirus, adenovirus, herpesvirus, alphavirus, poliovirus, Epstein-Barr, bacterial, and DNA-based systems in the documents cited herein and the knowledge of coding DNA from lentiviruses, retroviruses or immunodeficiency viruses, e.g., EIAV, FIV, BIV, HIV, or SIV, from the documents cited herein, alternative poxvirus, baculovirus, adenovirus, herpesvirus, alphavirus, poliovirus, Epstein-Barr, bacterial, and DNA-based recombinants containing and expressing DNA from lentiviruses, retroviruses or immunodeficiency viruses, e.g., EIAV, FIV, BIV, HIV, or SIV, such as Env, Gag and protease and Gag and protease, recombinants are generated. Analysis demonstrates incorporation into the vectors of the exogenous DNA and of expression thereof. Such additional recombinants are useful in the same manner as the above-described ALVAC embodiments.

Having thus described in detail preferred embodiments of the present invention, it is to be understood that the invention defined by the appended claims is not to be limited by particular details set forth in the above description as many apparent variations thereof are possible without departing from the spirit or scope thereof.

REFERENCES

1. Abimiku, A., Franchini, G., Tartaglia, J., Aldrich, K., Myagkikh, M., Markham, P. D., Chong, P., Klein, M., Kieny, M. P., Paoletti, E., Gallo, R. C., and Guroff, M. R., Nature Medicine 1, 321–329 (1995).
2. Altenburger, W., C-P. Suter and J. Altenburger, Archives Virol. 105, 15–27 (1989).
3. Behbehani, A. M., Microbiological Reviews 47, 455–509 (1983).
4. Bergoin, M., and Dales, S., In Comparative Virology, eds. K. Maramorosch and E. Kurstak, (Academic Press, NY) pp. 169–205 (1971).
5. Berman, P., Gregory, T., Riddle, L., Nakamura, G., Champe, M., Porter, J., Wurm, F., Hershberg, R., Cobb, E. and Eichberg, J., Nature 345, 622–625 (1990).
6. Bocchia, M. et al., Blood 85, 2680–2684.
7. Buller, R. M. L., G. L. Smith, Cremer, K., Notkins, A. L., and Moss, B., Nature 317, 813–815 (1985).
8. Cadoz, M., A. Strady, B. Meignier, J. Taylor, J. Tartaglia, E. Paoletti and S. Plotkin, The Lancet, 339, 1429–1432 (1992).
9. Child, S. J., Palumbo, G. J., Buller, R. M. L., and Hruby, D. E. Virology 174, 625–629 (1990).
10. Clements, M. L., Weinhold, K., Siliciano, R., Schwartz, D., Matthews, T., Graham, B., Keefer, M., McElrath, J., Gorse, G., Hsieh, R., Duliege, A. M., Excler, J., Meignier, B., Tartaglia, J., and Paoletti, E., HIV immunity induced by canarypox (ALVAC)-MN gl160, -SF-2, rgp120 or both. XI International Conference on AIDS/Vancouver 1996/Mo.A.281 (1996).
11. Clewell, D. B. and D. R. Helinski, Proc. Natl. Acad. Sci. USA 62, 1159–1166 (1969).
12. Clewell, D. B., J. Bacteriol 110, 667–676 (1972).
13. Cox, W. I., Tartaglia, J., and E. Paoletti. Virology 195, 845–850 (1993).
14. Daniel, M. D., Kirchhoff, F., Czajak, S. C., Sehgal, P. K., and Descssers, R., Science 258, 1938–1941 (1992).
15. Drillien et al., Virology 111, 488–499 (1981)
16. Edbauer, C., R. Weinberg, J. Taylor, A. Rey-Senelonge, J. F. Bouquet, P. Desmettre, and E. Paoletti, Virology 179, 901–904 (1990).
17. Eldridge, J. H., et al., Current Topics in Microbiology and Immunology, 146:59–66 (1989).
18. Emini, E., Schleif, W., Nunberg, J., Conley, A., Eda, Y., Tokiyoshi, S., Putney, S., Matsushita, S., Cobb, K., Jett, C., Eichberg, J., and K. Murthy, Nature 355, 728–730 (1992).

19. Engelke, D. R., Hoener, P. A., and Collins, F. S., Proc. Natl. Acad. Sci. USA 85, 544–548 (1988).
20. Englehard, V. H., Ann. Rev. Immunol. 12:181 (1994).
21. Franchini, G., Tartaglia, J., Markham, P., Benson, J., Fullen, J., Wills, M., Arp, J., Dekaban, G., Paoletti, E., and Gallo, R. C., AIDS Res. Hum. Retroviruses 11, 307–313 (1995).
22. Francini, G. Guroff, M. R., Tartaglia, J., Aggarwal, A., Abimiku, A., Benson, J., Markham, P., Limbach, K., Hurteau, G., Fullen, J., Aldrich, K., Miller, N., Sadoff, J., Paoletti, E., and Gallo, R. C., AIDS Res. Hum. Retroviruses 11, 909–920 (1995).
23. Fries et al., 32nd Interscience Conference on Antimicrobial Agents and Chemotherapy, Anaheim, Calif. (October 1992).
24. Fries, L. F., Tartaglia, J., Taylor, J., Kauffman, E. K., Meignier, B., Paoletti, E., and Plotkin, S., Vaccine 14, 428–434 (1996).
25. Fultz, P., Nara, P., Barre-Sinoussi, F., Chaput, A., Greenberg, M., Muchmore, E., Kieny, M.-P. and Girard, M. Science 256, 1687–1689 (1992).
26. Funahashi, S., T. Sato and H. Shida, J. Gen. Virol. 69, 35–47 (1988).
27. Gillard, S., Spehner, D., Drillien, R., and Kirn, A., Proc. Natl. Acad. Sci. USA 83, 5573–5577 (1986).
28. Girard, M., Kieny, M.-P., Pinter, A., Barre-Sinoussi, F., Nara, P., Kolbe, H., Kusui, K., Chaput, A., Reinhart, T., Muchmore, E., Ronco, J., Kaczorek, M., Gomard, E., Gluckman, J.-C. and Fultz, P., Proc. Natl. Acad. Sci. USA 88, 542–546 (1991).
29. Goebel, S. J., G. P. Johnson, M. E. Perkus, S. W. Davis, J. P. Winslow and E. Paoletti, Virology 179, 517–563 (1990b).
30. Goebel, S. J., Johnson, G. P., Perkus, M. E., Davis, S. W., Winslow, J. P., Paoletti, E., Virology 179, 247–266 (1990a).
31. Goldstein, D. J. and S. K. Weller, Virology 166, 41–51 (1988).
32. Goodman-Snitkoff et al., J. Immunol. 147:410–415 (1991).
33. Guo, P., Goebel, S., Davis, S., Perkus, M. E., Languet, B., Desmettre, P., Allen, G., and Paoletti, E., J. Virol. 63, 4189–4198 (1989).
34. Guo et al., J. Virol. 64, 2399–2406 (1990).
35. Hardy, Jr., W. D. in Retrovirus Biology and Human Disease, Gallo, R. C. and Wong-Staal, eds., Marcel Dekker, New York, pp. 33–86, 1990.
36. Heeney, J. L., Holterman, L., ten Hoaft, P., et al., AIDS Res. Human. Retrovir. 10 Suppl. 2, S117–S121 (1994).
37. Hoise, M. J., Osborne, R. Yamamoto, J. K., Neil, J. C., and Jarrett, O. J. Virol. 69, 1253–1255 (1995).
38. Hruby, D. E. and L. A. Ball, J. Virol. 43, 403–409 (1982).
39. Hruby, D. E., R. A. Maki, D. B. Miller and L. A. Ball, Proc. Natl. Acad. Sci. USA 80, 3411–3415 (1983).
40. Hu, S.-L., Polacino, P., Klaniecki, J., Travis, B., Wrey, T., Pennathur, S., Stallard, V., Kornas, H., Langlois, A. J., and Benveniste, R. E. (1995) AIDS Research and Human Retroviruses 11:5136.
41. Hu, S.-L., Polacino, P. Stallard, V., Klaniecki, J., Pennathur, S., Travis, B. M., Misher, L., Kornas, H., Langlois, A. J., Morton, W. R., and Benveniste, R. Retroviruses of Human AIDS and Related Animal Diseases Nuviéme Colloque des Cent Gardeś; pg. 275–281, (1994).
42. Hu, S.-L., Abrams, K., Barber, G., Morn, P., Zarling, J., Langlois, A., Kuller, L., Morton, W. and Benveniste, R., Science 255, 456–459 (1992).
43. Ichihashi, Y. and Dales, S., Virology 46, 533–543 (1971).
44. Issel, C. J., Horohov, D. W., Lea, D. F. et al., J. Virology 66, 3398–3408 (1992).
45. Itamura, S., H. Iinuma, H. Shida, Y. Morikawa, K. Nerome and A. Oya, J. Gen. Virol. 71, 2859–2865 (1990).
46. Jacobson, J. G., D. A. Leib, D. J. Goldstein, C. L. Bogard, P. A. Schaffer, S. K. Weller and D. M. Coen, Virology 173, 276–283 (1989).
47. Jamieson, A. T., G. A. Gentry and J. H. Subak-Sharpe, J. Gen. Virol. 24, 465–480 (1974).
48. Johnson, C. A., Torres, B. A., Koyama, H., and Yamamoto, J. K AIDS Res. and Human. Retrovir. 10, 225–228 (1994).
49. Kato, S., M. Takahashi, S. Kameyama and J. Kamahora, Biken's 2, 353–363 (1959).
50. Kendrew, In The Encyclopedia of Molecular Biology (Blackwell Science Ltd.) (1995).
51. Konishi et al., Virology 190, 454–458 (1992).
52. Kotwal, G. J. and B. Moss, Virology 167, 524–537 (1988b).
53. Kotwal, G. J. and Moss, B., Nature (Lond.) 335, 176–178 (1988a).
54. Kotwal, G. J., S. N. Isaacs, R. McKenzie, M. M. Frank and B. Moss, Science 250, 827–830 (1990).
55. Kotwal, G. J., A. W. Hugin and B. Moss, Virology 171, 579–587 (1989a).
56. Kotwal, G. J. and B. Moss, J. Virol. 63, 600–606 (1989b).
57. Kreuter, J., In Microcapsules and Nanoparticles in Medicine and Pharmacology, M. Donbrow, ed. (CRC Press) p. 125–148.
58. Kuby, Janis, Immunology, pp. 79–81 (1992).
59. Lai et al., Virus Res. 12, 239–250 (1989)
60. Lawrence, C., Weinhold, K., McElrath, J., Excler, J. L. Duliege, A. M., Clements, M. L., Belche, R., Dolin, R., and Graham, B., AVUE 022: safety and immunogenicity of live recombinant canarypox vector containing the envelope, gag and protease genes of HIV-1 in seronegative adult volunteers. XI International Conference on AIDS/Vancouver 1996/Mo.A.282 (1996).
61. Mandecki, W., Proc. Natl. Acad. Sci. USA 83, 7177–7182 (1986).
62. Maniatis, T., Fritsch, E. F., and Sambrook, J. In Molecular cloning: a laboratory manual, (Cold Spring Harbor Laboratory, Cold Spring Harbor, N.Y.) (1982).
63. Matthews, R. E. F., Intervirology 17, 42–44 (1982).
64. Miller et al., J. Exp. Med. 176, 1739–1744 (1992).
65. Milstein, C., Scientific American 243, 66, 70 (1980).
66. Morgan, A. J., M. Mackett, S. Finerty, J. R. Arrand, F. T. Scullion and M. A. Epstein, J. Med. Virol. 25, 189–195 (1988).
67. Morikawa, S. and Bishop, D., Virol. 186, 389–397 (1992).
68. Moss, B., E. Winters and J. A. Cooper, J. Virol. 40, 387–395 (1981).
69. Nabel et al., Tibtech, May, 11, 211–215 (1993).
70. Okada, S. Ruiyu, P., Young, E., Stoffs, W. V., and Yamamoto, J. K., AIDS Res. and Human Retrovir. 10, 1739–1746 (1994).
71. Paez et al., PNAS USA 82, 3365–3369 (1985); see also Paez et al., Virology 169, 418–426 (1985).
72. Palumbo, G. J., Pickup, D. J., Fredrickson, T. N., Mcintyre, L. J., and Buller, R. M. L., Virology 172, 262–273 (1989).
73. Panicali, D., Davis, S. W., Mercer, S. R., and Paoletti, E., J. Virol. 37, 1000–1010 (1981).
74. Panicali, D. and E. Paoletti, Proc. Natl. Acad. Sci. USA 79, 4927–4931 (1982).

75. Patel, D. D. and Pickup, D. J., EMBO 6, 3787–3794 (1987).
76. Patel, D. D., Ray, C. A., Drucker, R. P., and Pickup, D. J., Proc. Natl. Acad. Sci. USA 85, 9431–9435 (1988).
77. Pedersen, N. C., Ho, E. W., Brown, M. L., and Yamamoto, J. K., Science 235, 790–793 (1987).
78. Perkus, M. E., S. J. Goebel, S. W. Davis, G. P. Johnson, E. K. Norton and E. Paoletti, Virology 180, 406–410 (1991).
79. Perkus, M. E., Goebel, S. J., Davis, S. W., Johnson, G. P., Limbach, K., Norton, E. K., and Paoletti, E., Virology 179, 276–286 (1990).
80. Perkus, M. E., A. Piccini, B. R. Lipinskas and E. Paoletti, Science 229, 981–984 (1985).
81. Perkus, M. E., Limbach, K., and Paoletti, E., J. Virol. 63, 3829–3836 (1989).
82. Perkus, M. E., D. Panicali, S. Mercer and E. Paoletti, Virology 152, 285–297 (1986).
83. Pialoux et al., Aids Research and Human Retroviruses, 11(3):373–81 (1995).
84. Piccini, A., M. E. Perkus, and E. Paoletti, Methods in Enzymology 153, 545–563 (1987).
85. Pickup, D. J., B. S. Ink, B. L. Parsons, W. Hu and W. K. Joklik, Proc. Natl. Acad. Sci. USA 81, 6817–6821 (1984).
86. Pickup, D. J., B. S. Ink, W. Hu, C. A. Ray and W. K. Joklik, Proc. Natl. Acad. Sci. USA 83, 7698–7702 (1986).
87. Sadora, D. L., Shapaer, E. G., Kitchell, B. E., Dow, S. W., Hoover, E. A., and Mullins, J. I., J. Virol. 68 (1994).
88. Sanger, F., Nickel, S. Coulson, A. R., Proc. Natl. Acad. Sci. 74, 5463–5467 (1977).
89. Schmidtt, J. F. C. and H. G. Stunnenberg, J. Virol. 62, 1889–1897 (1988).
90. Shida, H., Virology 150, 451–462 (1986).
91. Shida, H., T. Tochikura, T. Sato, T. Konno, K. Hirayoshi, M. Seki, Y. Ito, M. Hatanaka, Y. Hinuma, M. Sugimoto, F. Takahashi-Nishimaki, T. Maruyama, K. Miki, K. Suzuki, M. Morita, H. Sashiyama and M. Hayami, EMBO 6, 3379–3384 (1987).
92. Shida, H., Hinuma, Y., Hatanaka, M., Morita, M., Kidokoro, M., Suzuki, K., Maruyzam, T., Takahashi-Nishimaki, F., Sugimoto, M., Kitamura, R., Miyazawa, T., and Hayami, M., J. Virol. 62, 4474–4480 (1988).
93. Slabaugh, M., N. Roseman, R. Davis and C. Mathews, J. Virol. 62, 519–527 (1988).
94. Song, W., Collison, E. W., Bilingsley, P., and Brown, W. C. J. Virol. 66, 5409–5417 (1992).
95. Stanberry, L. R., S. Kit and M. G. Myers, J. Virol. 55, 322–328 (1985).
96. Tabor, S. and C. C. Richardson, Proc. Natl. Acad. Sci. USA 84, 4767–4771 (1987).
97. Tartaglia, J., Jarrett, O., Desmettre, P., Paoletti, E., J. Virol. 67, 2370–2375 (1993b).
98. Tartaglia, J., Perkus, M. E., Taylor, J., Norton, E. K., Audonnet, J.-C., Cox, W. I., Davis, S. W., Van Der Hoeven, J., Meignier, B., Riviere, M., Languet, B., Paoletti, E., Virology 188, 217–232 (1992).
99. Tartaglia, J., Pincus, S., Paoletti, E., Critical Reviews in Immunology 10, 13–30 (1990a).
100. Tartaglia, J., J. Taylor, W. I. Cox, J.-C. Audonnet, M. E. Perkus, A. Radaelli, C. de Giuli Morghen, B. Meignier, M. Riviere, K. Weinhold & E. Paoletti, In AIDS Research Reviews, W. Koff, F. Wong-Staal & R. C. Kenedy, Eds., Vol. 3, Marcel Dekker, NY, pp. 361–378 (1993a).
101. Tartaglia, J. & E. Paoletti, In Immunochemistry of Viruses, II. The Basis for Serodiagnosis and Vaccines. M. H. V. van Regenmortel & A. R. Neurath, Eds. 125–151. Elsevier Science Publishers, Amsterdam (1990b).
102. Taylor, J., R. Weinberg, J. Tartaglia, C. Richardson, G. Alkhatib, D. Briedis, M. Appel, E. Norton & E. Paoletti, Virology 187, 321–328 (1992).
103. Taylor, J., Edbauer, C., Rey-Senelonge, A., Bouquet, J.-F., Norton, E., Goebel, S., Desmettre, P., Paoletti, E., J. Virol. 64, 1441–1450 (1990).
104. Taylor, J., Weinberg, R., Kawaoka, Y., Webster, R. G., and Paoletti, E., Vaccine 6, 504–508 (1988a).
105. Taylor, J., R. Weinberg, B. Lanquet, P. Desmettre, and E. Paoletti, Vaccine 6, 497–503 (1988b).
106. Taylor, G., E. J. Stott, G. Wertz and A. Ball, J. Gen. Virol. 72, 125–130 (1991a).
107. Taylor, J., C. Trimarchi, R. Weinberg, B. Languet, F. Guillemin, P. Desmettre and E. Paoletti, Vaccine 9, 190–193 (1991b).
108. Van der Ryst, E., Fultz, P. N., Tartaglia, J., Barre-Sinnousi, F., Paoletti, E., Nara, P., Meignier, B., Blondeau, C., Muchmore, E., and Girard, M., Protection from HIV-1 challenge in chimpanzees by immunization with a canarypox virus recombinant. XI International conference on AIDS/Vancouver/1996, We.A.280 (1996).
109. Verschoor, E. J., Willlemse, M. J., Stam, J. G., van Vliet, A. L. W., Pouwels, H., Chalmers, S. K., Horzinek, M. C., Sandermeijer, P. J. A., Hesselink, W., and de Ronde, A., Vaccine 14, 285–289 (1996).
110. Vos, J. and Stunnenberg, H., EMBO J. 7, 3487–3492 (1988).
111. Wang, R-F and Mullins, J. I., Gene 153, 197–202 (1995).
112. Webster et al., Vaccine, 12(16), 1495–1498 (1994).
113. Weir, J. P. and B. Moss, J. Virol. 46, 530–537 (1983).
114. Yamamoto, J. K., Hohdatsu, T., Olmstead, R. A., Pu, R., Lowe, H. Zochlinski, H., Acevedo, V., Johnson, H. M., Soulds, G. A., and Gardner, M. B., J. Virol. 67, 601–605 (1993).
115. Yamamoto, J. K., Okuda, T., Ackley, C. D., Lowe, H. Zochlinkski, H., Pembroke, E., and Gardner, M. B., AIDS Res. Human Retrovir. 7, 911–922 (1991).
116. Yuen, L., and Moss, B., Proc. Natl. Acad. Sci. USA 84, 6417–6421 (1987).
117. Zhou, J., L. Crawford, L. McLean, X. Sun, M. Stanley, N. Almond and G. L. Smith, J. Gen. Virol. 71, 2185–2190 (1990).

What is claimed is:

1. A vaccine that induces a protective immune response in a feline against homologous and heterologous feline immunodeficiency virus, comprising a carrier and an ALVAC recombinant poxvirus that consists essentially of, and expresses in vivo in a feline, nucleic acid molecules encoding FIV Gag and protease.

2. A method for inducing a protective immune response against FIV in a feline comprising administering to the feline the vaccine of claim 1.

* * * * *

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
        (A) LENGTH: 2571 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

```
ATGGCAGAAG GATTTGCAGC CAATAGACAA TGGATAGGAC CAGAAGAAGC TGAAGAGTTA     60
TTAGATTTTG ATATAGCAAC ACAAATGAGT GAAGAAGGAC CACTAAATCC AGGAGTAAAC    120
CCATTTAGGG TACCTGGAAT AACAGAAAAA GAAAAGCAAA ACTACTGTAA CATATTACAA    180
CCTAAGTTAC AAGATCTAAG GAACGAAATT CAAGAGGTAA AACTGGAAGA AGGAAATGCA    240
GGTAAGTTTA GAAGAGCAAG ATTTTTAAGG TATTCTGATG AACAAGTATT GTCCCTGGTT    300
CATGCGTTCA TAGGATATTG TATATATTTA GGTAATCGAA ATAAGTTAGG ATCTTTAAGA    360
CATGACATTG ATATAGAAGC ACCCCAAGAA GAGTGTTATA ATAATAGAGA AGGGGTACA    420
ACTGACAATA TAAAATATGG TAGACGATGT TGCCTAGGAA CGGTGACTTT GTACCTGATT    480
TTATTTATAG GATTAATAAT ATATTCACAG ACAACCAACG CTCAGGTAGT ATGGAGACTT    540
CCACCATTAG TAGTCCCAGT AGAAGAATCA GAAATAATTT TTTGGGACTG TTGGGCACCA    600
GAAGAACCCG CCTGTCAGGA CTTTCTTGGG GCAATGATAC ATCTAAAAGC TAAGACAAAT    660
ATAAGTATAC GAGAGGGACC TACCTTGGGG AATTGGACTA GAGAAATATG GCAACATTA    720
TTCAAAAAGG CTACTAGACA ATGTAGAAGA GGCAGAATAT GGAAAAGATG GAATGAGACT    780
ATAACAGGAC CATCAGGATG TGCTAATAAC ACATGTTATA ATGTTTCAGT AATAGTACCT    840
GATTATCAGT GTTATTTAGA TAGAGTAGAT ACTTGGTTAC AAGGGAAAAT AAATATATCA    900
TTATGTCTAA CAGGAGGAAA AATGTTGTAC AATAAAGTTA CAAAACAATT AAGCTATTGT    960
ACAGACCCAT TACAAATCCC ACTGATCAAT TATACATTTG GACCTAATCA AACATGTATG   1020
TGGAATACTT CACAAATTCA GGACCCTGAA ATACCAAAAT GTGGATGGTG GAATCAAATG   1080
GCCTATTATA ACAGTTGTAA ATGGGAAGAG GCAAAGGTAA AGTTTCATTG TCAAAGAACA   1140
CAGAGTCAGC CTGGATCATG GCGTAGAGCA ATCTCGTCAT GGAAACAAAG AAATAGATGG   1200
GAGTGGAGAC CAGATTTTGG AAGTAAAAAG GTGAAAATAT CTCTACAGTG CAATAGCACA   1260
AAAAACCTAA CCTTTGCAAT GAGAAGTTCA GGAGATTATG GAGAAGTAAC GGGAGCTTGG   1320
ATAGAGTTTG GATGTCATAG AAATAAATCA AAACATCATT CTGAAGCAAG GTTTAGAATT   1380
AGATGTAGAT GGAATGTAGG ATCCGATACC TCGCTCATTG ATACATGTGG AAACACTCGA   1440
GATGTTTCAG GTGCGAATCC TGTAGATTGT ACCATGTATT CAAATAAAAT GTACAATTGT   1500
TCTTTACAAA ATGGGTTTAC TATGAAGGTA GATGACCTTA TTGTGCATTT CAATATGACA   1560
AAAGCTGTAG AAATGTATAA TATTGCTGGA AATTGGTCTT GTACATCGA CTTGCCATCG   1620
TCATGGGGGT ATATGAATTG TAATTGTACA AATAGTAGTA GTAGTTATAG TGGTACTAAA   1680
ATGGCATGTC CTAGCAATCG AGGCATCTTA AGGAATTGGT ATAACCCAGT AGCAGGATTA   1740
CGACAATCCT TAGAACAGTA TCAAGTTGTA AAACAACCAG ATTACTTAGT GGTCCCAGAG   1800
GAAGTCATGG AATATAAACC TAGAAGGAAA AGGGCAGCTA TTCATGTTAT GTTGGCTCTT   1860
GCAACAGTAT TATCTATTGT CGGTGCAGGG ACGGGGCTA CTGCTATAGG GATGGTAACA   1920
CAATACCACC AAGTTCTGGC AACCCATCAA GAAGCTATAG AAAAGGTGAC TGAAGCCTTA   1980
AAGATAAACA ACTTAAGATT AGTTACATTA GAGCATCAAG TACTAGTAAT AGGATTAAAA   2040
```

-continued

```
GTAGAAGCTA TGGAAAAATT TTTATATACA GCTTTCGCTA TGCAAGAATT AGGATGTAAT      2100

CAAAATCAAT TTTTCTGCAA AATCCCTCCT GGGTTGTGGA CAAGGTATAA TATGACTATA      2160

AATCAAACAA TATGGAATCA TGGAAATATA ACTTTGGGGG CATGGTATAA CCAAACAAAA      2220

GATTTACAAC AAAAGTTTTA TGAAATAATA ATGGACATAG AACAAAATAA TGTACAAGGG      2280

AAAACAGGGA TACAACAATT ACAAAAGTGG GAAGATTGGG TAGGATGGAT GGGAAATATT      2340

CCACAATATT TAAAGGGACT ATTGGGAGGT ATCTTGGGAA TAGGATTAGG AGTGTTATTA      2400

TTGATTTTAT GTTACCTAC ATTGGTTGAT TGTATAAGAA ATTGTATCCA CAAGATACTA       2460

GGATACACAG TAATTGCAAT GCCTGAAGTA GAAGGAGAAG AAATACAACC ACAAATGGAA      2520

TTGAGGAGAA ATGGTAGGCA ATGTGGCATG TCTGAAAAAG AGGAGGAATG A               2571

(2) INFORMATION FOR SEQ ID NO:2:

(i) SEQUENCE CHARACTERISTICS:
        (A) LENGTH: 4616 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

ATGGGGAATG GACAGGGGCG AGATTGGAAA ATGGCCATTA AGAGATGTAG TAATGTTGCT        60

GTAGGAGTAG GGGGGAAGAG TAAAAAATTT GGAGAAGGGA ATTTCAGATG GCCATTAGA       120

ATGGCTAATG TATCTACAGG ACGAGAACCT GGTGATATAC CAGAGACTTT AGATCAACTA      180

AGGTTGGTTA TTTGCGATTT ACAAGAAAGA AGAGAAAAAT TTGGATCTAG CAAAGAAATT      240

GATATGGCAA TTGTGACATT AAAAGTCTTT GCGGTAGCAG GACTTTTGAA TATGACGGTG      300

TCTACTGCTG CTGCAGCTGA AAATATGTAT TCTCAAATGG GATTAGACAC TAGGCCATCT      360

ATGAAAGAAG CAGGTGGAAA AGAGGAAGGC CCTCCACAGG CATATCCTAT TCAAACAGTA      420

AATGGAGTAC CACAATATGT AGCACTTGAC CCAAAAATGG TGTCCATTTT TATGGAAAAG      480

GCAAGAGAAG GACTAGGAGG GGAGGAAGTT CAACTATGGT TTACTGCCTT CTCTGCAAAT      540

TTAACACCTA CTGACATGGC CACATTAATA ATGGCCCGAC CAGGGTGCGC TGCAGATAAA      600

GAAATATTGG ATGAAAGCTT AAAGCAACTG ACAGCAGAAT ATGATCGCAC ACATCCCCCT      660

GATGCTCCCA GACCATTACC CTATTTTACT GCAGCAGAAA TTATGGGTAT AGGATTAACT      720

CAAGAACAAC AAGCAGAAGC AAGATTTGCA CCAGCTAGGA TGCAGTGTAG AGCATGGTAT      780

CTCGAGGCAT TAGGAAAATT GGCTGCCATA AAAGCTAAGT CTCCTCGAGC TGTGCAGTTA      840

AGACAAGGAG CTAAGGAAGA TTATTCATCC TTTATAGACA GATTGTTTGC CCAAATAGAT      900

CAAGAACAAA ATACAGCTGA AGTTAAGTTA TATTTAAAAC AGTCATTAAG CATAGCTAAT      960

GCTAATGCAG ACTGTAAAAA GGCAATGAGC CACCTTAAGC CAGAAAGTAC CCTAGAAGAA     1020

AAGTTGAGAG CTTGTCAAGA AATAGGCTCA CCAGGATATA AATGCAACT CTTGGCAGAA      1080

GCTCTTACAA AAGTTCAAGT AGTGCAATCA AAAGGATCAG GACCAGTGTG TTTTAATTGT     1140

AAAAAACCAG GACATCTAGC AAGACAATGT AGAGAAGTGA AAAAATGTAA TAAATGTGGA     1200

AAACCTGGTC ATCTAGCTGC CAAATGTTGG CAAGGAAATA GAAAGAATTC GGGAAACTGG     1260

AAGGCGGGGC GAGCTGCAGC CCCAGTGAAT CAAATGCAGC AAGCAGTAAT GCCATCTGCA     1320

CCTCCAATGG AGGAGAAACT ATTGGATTTA TAAATTATAA TAAAGTAGGT ACGACTACAA     1380

CATTAGAAAA GAGGCCAGAA ATACTTATAT TTGTAAATGG ATATCCTATA AAATTTTTAT     1440
```

```
TAGATACAGG AGCAGATATA ACAATTTTAA ATAGGAGAGA TTTTCAAGTA AAAAATTCTA    1500

TAGAAAATGG AAGGCAAAAT ATGATTGGAG TAGGAGGAGG AAAGAGAGGA ACAAATTATA    1560

TTAATGTACA TTTAGAGATT AGAGATGAAA ATTATAAGAC ACAATGTATA TTTGGTAATG    1620

TTTGTGTCTT AGAAGATAAC TCATTAATAC AACCATTATT GGGGAGAGAT AATATGATTA    1680

AATTCAATAT TAGGTTAGTA ATGGCTCAAA TTTCTGATAA GATTCCAGTA GTAAAAGTAA    1740

AAATGAAGGA TCCTAATAAA GGACCTCAAA TAAAACAATG GCCATTAACA AATGAAAAAA    1800

TTGAAGCCTT AACAGAAATA GTAGAAAGAC TAGAAAGAGA AGGGAAAGTA AAAAGAGCAG    1860

ATCCAAATAA TCCATGGAAT ACACCAGTAT TTGCTATAAA AAAGAAAAGT GGAAAATGGA    1920

GAATGCTCAT AGATTTTAGA GAATTAAACA AACTAACTGA GAAAGGAGCA GAGGTCCAGT    1980

TGGGACTACC TCATCCTGCT GGGTTACAAA TAAAAAAACA AGTAACAGTA TTAGATATAG    2040

GGATGCATA TTTCACCATT CCTCTTGATC CAGATTATGC TCCTTATACA GCATTTACTT    2100

TACCTAGGAA AAATAATGCG GGACCAGGAA GGAGATTTGT GTGGTGTAGT CTACCACAAG    2160

GCTGGATTTT AAGTCCATTG ATATATCAAA GTACATTAGA TAATATAATA CAACCTTTTA    2220

TTAGACAAAA TCCTCAATTA GATATTTACC AATATATGGA TGACATTTAT ATAGGATCAA    2280

ATTTAAGTAA AAAGGAGCAT AAAGAAAAGG TAGAAGAATT AAGAAAATTA CTATTATGGT    2340

GGGGATTTGA AACTCCAGAA GATAAAATTAC AGGAAGAACC CCCATATACA TGGATGGGTT    2400

ATGAATTACA TCCATTAACA TGGACAAATAC AACAGAAACA GTTAGACATT CCAGAACAGC    2460

CCACTCTAAA TGAGTTGCAA AAATTAGCAG GAAAAATTAA TTGGGCTAGC CAAGCTATTC    2520

CAGACTTGAG TATAAAAGCA TTAACTAACA TGATGAGAGG AAATCAAAAC CTAAATTCAA    2580

CAAGACAATG GACTAAAGAA GCTCGACTGG AAGTACAAAA GGCAAAAAAG CTATAGAAG    2640

AACAAGTACA ACTAGGATAC TATGACCCCA GTAAGGAGTT ATATGCTAAA TTAAGTTTGG    2700

TGGGACCACA TCAAATAAGT TATCGAGTAT ATCAGAAGGA TCAAGAAAAG ATACTATGGT    2760

ATGGAAAAAT GAGTAGACAA AAGAAAAAGG CAGAAAATAC ATGTGATATA GCCTTAAGAG    2820

CATGCTATAA GATAAGAGAA GAGTCTATTA TAAGAATAGG AAAAGAACCA AGATATGAAA    2880

TACCTACTTC TAGAGAAGCC TGGGAATCAA ATCTAATTAA TTCACCATAT CTTAAGGCCC    2940

CACCTCCTGA GGTAGAATAT ATCCATGCTG CTTTGAATAT AAAGAGAGCG TTAAGTATGA    3000

TAAAAGATGC TCCAATACCA GGAGCAGAAA CATGGTATAT AGATGGAGGT AGAAAACTAG    3060

GAAAAGCAGC AAAAGCAGCC TATTGGACAG ATACAGGAAA GTGGAAAGTG ATGGAATTAG    3120

AAGGCAGTAA TCAGAAGGCA GAAATACAAG CATTATTATT GGCATTAAAA GCAGGATCAG    3180

AGGAGATGAA TATTATAACA GATTCACAAT ATGCTATAAA TATTATTCTT CAACAACCAG    3240

ATATGATGGA GGGAATCTGG CAAGAAGTTT TAGAAGAATT GGAGAAGAAA ACAGCAATAT    3300

TTATAGATTG GGTCCCAGGA CATAAAGGTA TTCCAGGAAA TGAGGAAGTA GATAAGCTTT    3360

GTCAAACAAT GATGATAATA GAAGGGGATG GGATATTAGA CAAAAGGTCA GAAGATGCAG    3420

GATATGATTT ATTAGCTGCA AAAGAAATAC ATTTATTGCC AGGAGAGGTA AAAGTAATAC    3480

CAACAGGGGT AAAGCTAATG CTGCCTAAAG GACATTGGGG ATTAATAATC GGAAAAAGCT    3540

CGATGGGGAG TAAAGGATTG GATGTATTAG GAGGAGTAAT AGATGAAGGA TATCGAGGTG    3600

AAATTGGAGT AATAATGATT AATGTATCAA GAAAATCAAT CACCTTAATG GAACGACAAA    3660

AGATAGCACA ATTAATAATA CTGCCTTGTA AACATGAAGT ATTAGAACAA GGAAAAGTAG    3720

TAAGGGATTC AGAGAGAGGA GGCAATGGTT ATGGGTCAAC AGGAGTATTC TCCTCTTGGG    3780
```

-continued

| | |
|---|---|
| TTGACAGAAT TGAGGAAGCA GAAATAAATC ATGAAAAATT TCACTCAGAT CCACAGTACT | 3840 |
| TAAGGACTGA ATTTAATTTA CCTAAAATGG TAGCAGAAGA GATAAGACGA AAATGCCCAG | 3900 |
| TATGCAGAAT CAGAGGAGAA CAAGTGGGAG GACAATTGAA AATAGGGCCT GGTATCTGGC | 3960 |
| AAATGGATTG CACACACTTT GATGGCAAAA TAATTCTTGT GGGTATACAT GTGGAATCAG | 4020 |
| GATATATATG GCACAAATA ATTTCTCAAG AAACTGCTGA CTGTACAGTT AAAGCTGTTT | 4080 |
| TACAATTGTT GAGTGCTCAT AATGTTACTG AATTACAAAC AGATAATGGA CCAAATTTTA | 4140 |
| AAAATCAAAA GATGGAAGGA GTACTCAATT ACATGGGTGT GAAACATAAG TTTGGTATCC | 4200 |
| CAGGGAACCC ACAGTCACAA GCATTAGTTG AAAATGTAAA TCATACATTA AAAGTTTGGA | 4260 |
| TTCGGAAATT TTTGCCTGAA ACAACCTCCT TGGATAATGC CTTATCTCTC GCTGTACATA | 4320 |
| GTCTCAATTT TAAAAGAAGA GGTAGGATAG GAGGGATGGC CCCTTATGAA TTATTAGCAC | 4380 |
| AACAAGAATC CTTAAGAATA CAAGATTATT TTTCTGCAAT ACCACAAAAA TTGCAAGCAC | 4440 |
| AGTGGATTTA TTATAAAGAT CAAAAGATA AGAAATGGAA AGGACCAATG AGAGTAGAAT | 4500 |
| ACTGGGGACA GGGATCAGTA TTATTAAAGG ATGAAGAGAA GGGATATTTT CTTATACCTA | 4560 |
| GGAGACACAT AAGGAGAGTT CCAGAACCCT GCGCTCTTCC TGAAGGGGAT GAGTGA | 4616 |

(2) INFORMATION FOR SEQ ID NO:3:

(i) SEQUENCE CHARACTERISTICS:
        (A) LENGTH: 1615 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

| | |
|---|---|
| GAGCTCGCGG CCGCCTATCA AAAGTCTTAA TGAGTTAGGT GTAGATAGTA TAGATATTAC | 60 |
| TACAAAGGTA TTCATATTTC CTATCAATTC TAAAGTAGAT GATATTAATA ACTCAAAGAT | 120 |
| GATGATAGTA GATAATAGAT ACGCTCATAT AATGACTGCA AATTTGGACG TTCACATTT | 180 |
| TAATCATCAC GCGTTCATAA GTTTCAACTG CATAGATCAA AATCTCACTA AAAGATAGC | 240 |
| CGATGTATTT GAGAGAGATT GGACATCTAA CTACGCTAAA GAAATTACAG TTATAAATAA | 300 |
| TACATAATGG ATTTTGTTAT CATCAGTTAT ATTTAACATA AGTACAATAA AAGTATTAA | 360 |
| ATAAAAATAC TTACTTACGA AAAAATGACT AATTAGCTAT AAAAACCCGG GCTGCAGCTC | 420 |
| GAGGAATTCT TTTTATTGAT TAACTAGTCA AATGAGTATA TAATTGAA AAAGTAAAAT | 480 |
| ATAAATCATA TAATAATGAA ACGAAATATC AGTAATAGAC AGGAACTGGC AGATTCTTCT | 540 |
| TCTAATGAAG TAAGTACTGC TAAATCTCCA AAATTAGATA AAAATGATAC AGCAAATACA | 600 |
| GCTTCATTCA ACGAATTACC TTTTAATTTT TTCAGACACA CCTTATTACA AACTAACTAA | 660 |
| GTCAGATGAT GAGAAAGTAA ATATAAATTT AACTTATGGG TATAATATAA TAAAGATTCA | 720 |
| TGATATTAAT AATTTACTTA ACGATGTTAA TAGACTTATT CCATCAACCC CTTCAAACCT | 780 |
| TTCTGGATAT TATAAAATAC CAGTTAATGA TATTAAAATA GATTGTTTAA GAGATGTAAA | 840 |
| TAATTATTTG GAGGTAAAGG ATATAAAATT AGTCTATCTT TCACATGGAA ATGAATTACC | 900 |
| TAATATTAAT AATTATGATA GGAATTTTTT AGGATTTACA GCTGTTATAT GTATCAACAA | 960 |
| TACAGGCAGA TCTATGGTTA TGGTAAAACA CTGTAACGGG AAGCAGCATT CTATGGTAAC | 1020 |
| TGGCCTATGT TTAATAGCCA GATCATTTTA CTCTATAAAC ATTTTACCAC AAATAATAGG | 1080 |
| ATCCTCTAGA TATTTAATAT TATATCTAAC AACAACAAAA AAATTTAACG ATGTATGGCC | 1140 |

-continued

```
AGAAGTATTT TCTACTAATA AAGATAAAGA TAGTCTATCT TATCTACAAG ATATGAAAGA      1200

AGATAATCAT TTAGTAGTAG CTACTAATAT GGAAAGAAAT GTATACAAAA ACGTGGAAGC      1260

TTTTATATTA AATAGCATAT TACTAGAAGA TTTAAAATCT AGACTTAGTA TAACAAAACA      1320

GTTAAATGCC AATATCGATT CTATATTTCA TCATAACAGT AGTACATTAA TCAGTGATAT      1380

ACTGAAACGA TCTACAGACT CAACTATGCA AGGAATAAGC AATATGCCAA TTATGTCTAA      1440

TATTTTAACT TTAGAACTAA AACGTTCTAC CAATACTAAA AATAGGATAC GTGATAGGCT      1500

GTTAAAAGCT GCAATAAATA GTAAGGATGT AGAAGAAATA CTTTGTTCTA TACCTTCGGA      1560

GGAAAGAACT TTAGAACAAC TTAAGTTTAA TCAAACTTGT ATTTATGAAG GTACC          1615
```

(2) INFORMATION FOR SEQ ID NO:4:

(i) SEQUENCE CHARACTERISTICS:
        (A) LENGTH: 2879 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
TTAAATAAAA ATACTTACTT ACGAAAAATG ACTAATTAGC TATAAAAACC CGGGTTCTTT        60

ATTCTATACT TAAAAAGTGA AAATAAATAC AAAGGTTCTT GAGGGTTGTG TTAAATTGAA       120

AGCGAGAAAT AATCATAAAT TATTTCATTA TCGCGATATC CGTTAAGTTT GTATCGTAAT       180

GGCAGAAGGA TTTGCAGCCA ATAGACAATG GATAGGACCA GAAGAAGCTG AAGAGTTATT       240

AGATTTTGAT ATAGCAACAC AAATGAGTGA AGAAGGACCA CTAAATCCAG GAGTAAACCC       300

ATTTAGGGTA CCTGGAATAA CAGAAAAAGA AAAGCAAAAC TACTGTAACA TATTACAACC       360

TAAGTTACAA GATCTAAGGA ACGAAATTCA AGAGGTAAAA CTGGAAGAAG GAAATGCAGG       420

TAAGTTTAGA AGAGCAAGAT TTTTAAGGTA TTCTGATGAA CAAGTATTGT CCCTGGTTCA       480

TGCGTTCATA GGATATTGTA TATATTTAGG TAATCGAAAT AAGTTAGGAT CTTTAAGACA       540

TGACATTGAT ATAGAAGCAC CCCAAGAAGA GTGTTATAAT AATAGAGAGA AGGGTACAAC       600

TGACAATATA AAATATGGTA GACGATGTTG CCTAGGAACG GTGACTTTGT ACCTGATTTT       660

ATTTATAGGA TTAATAATAT ATTCACAGAC AACCAACGCT CAGGTAGTAT GGAGACTTCC       720

ACCATTAGTA GTCCCAGTAG AAGAATCAGA ATAATTTTTT TGGGACTGTT GGGCACCAGA       780

AGAACCCGCC TGTCAGGACT TTCTTGGGGC AATGATACAT CTAAAAGCTA AGACAAATAT       840

AAGTATACGA GAGGGACCTA CCTTGGGGAA TTGGACTAGA GAAATATGGG CAACATTATT       900

CAAAAAGGCT ACTAGACAAT GTAGAAGAGG CAGAATATGG AAAAGATGGA ATGAGACTAT       960

AACAGGACCA TCAGGATGTG CTAATAACAC ATGTTATAAT GTTTCAGTAA TAGTACCTGA      1020

TTATCAGTGT TATTTAGATA GAGTAGATAC TTGGTTACAA GGGAAAATAA ATATATCATT      1080

ATGTCTAACA GGAGGAAAAA TGTTGTACAA TAAAGTTACA AAACAATTAA GCTATTGTAC      1140

AGACCCATTA CAAATCCCAC TGATCAATTA TACATTTGGA CCTAATCAAA CATGTATGTG      1200

GAATACTTCA CAAATTCAGG ACCCTGAAAT ACCAAAATGT GGATGGTGGA ATCAAATGGC      1260

CTATTATAAC AGTTGTAAAT GGGAAGAGGC AAAGGTAAAG TTTCATTGTC AAAGAACACA      1320

GAGTCAGCCT GGATCATGGC GTAGAGCAAT CTCGTCATGG AAACAAAGAA ATAGATGGGA      1380

GTGGAGACCA GATTTGGAAA GTAAAAAGGT GAAAATATCT CTACAGTGCA ATAGCACAAA      1440

AAACCTAACC TTTGCAATGA GAAGTTCAGG AGATTATGGA GAAGTAACGG GAGCTTGGAT      1500
```

```
AGAGTTTGGA TGTCATAGAA ATAAATCAAA ACATCATTCT GAAGCAAGGT TTAGAATTAG      1560

ATGTAGATGG AATGTAGGAT CCGATACCTC GCTCATTGAT ACATGTGGAA ACACTCGAGA      1620

TGTTTCAGGT GCGAATCCTG TAGATTGTAC CATGTATTCA AATAAAATGT ACAATTGTTC      1680

TTTACAAAAT GGGTTTACTA TGAAGGTAGA TGACCTTATT GTGCATTTCA ATATGACAAA      1740

AGCTGTAGAA ATGTATAATA TTGCTGGAAA TTGGTCTTGT ACATCTGACT TGCCATCGTC      1800

ATGGGGTAT ATGAATTGTA ATTGTACAAA TAGTAGTAGT AGTTATAGTG GTACTAAAAT       1860

GGCATGTCCT AGCAATCGAG GCATCTTAAG GAATTGGTAT AACCCAGTAG CAGGATTACG     1920

ACAATCCTTA GAACAGTATC AAGTTGTAAA ACAACCAGAT TACTTAGTGG TCCCAGAGGA     1980

AGTCATGGAA TATAAACCTA GAAGGAAAAG GGCAGCTATT CATGTTATGT TGGCTCTTGC    2040

AACAGTATTA TCTATTGTCG GTGCAGGGAC GGGGGCTACT GCTATAGGGA TGGTAACCCA    2100

ATACCACCAA GTTCTGGCAA CCCATCAAGA AGCTATAGAA AAGGTGACTG AAGCCTTAAA    2160

GATAAACAAC TTAAGATTAG TTACATTAGA GCATCAAGTA CTAGTAATAG GATTAAAAGT   2220

AGAAGCTATG GAAAAATTCT TATATACAGC TTTCGCTATG CAAGAATTAG GATGTAATCA    2280

AAATCAATTC TTCTGCAAAA TCCCTCCTGG GTTGTGGACA AGGTATAATA TGACTATAAA    2340

TCAAACAATA TGGAATCATG GAAATATAAC TTTGGGGGAA TGGTATAACC AAACAAAAGA    2400

TTTACAACAA AAGTTTTATG AAATAATAAT GGACATAGAA CAAAATAATG TACAAGGGAA    2460

AACAGGGATA CAACAATTAC AAAAGTGGGA AGATTGGGTA GGATGGATGG GAAATATTCC    2520

ACAATATTTA AAGGGACTAT TGGGAGGTAT CTTGGGAATA GGATTAGGAG TGTTATTATT    2580

GATTTTATGT TTACCTACAT TGGTTGATTG TATAAGAAAT TGTATCCACA AGATACTAGG    2640

ATACACAGTA ATTGCAATGC CTGAAGTAGA AGGAGAAGAA ATACAACCAC AAATGGAATT    2700

GAGGAGAAAT GGTAGGCAAT GTGGCATGTC TGAAAAAGAG GAGGAATGAT GAAGTATCTC   2760

AGAATTCCTG CAGCCCGGGG GATCCTTAAT TAATTAGTTA TTAGACAAGG TGAAAACGAA    2820

ACTATTTGTA GCTTAATTAA TTAGCTGCAG GAATTCTTTT TATTGATTAA CTAGTCAAA    2879

(2) INFORMATION FOR SEQ ID NO:5:

(i) SEQUENCE CHARACTERISTICS:
        (A) LENGTH: 2032 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

TTAATCAATA AAAAGAATTC CTGCAGCCCT GCAGCTAATT AATTAAGCTA CAAATAGTTT       60

CGTTTTCACC TTGTCTAATA ACTAATTAAT TAAGGATCCC CCGTACCGGG CCCCCCCTCG     120

AGGTCGACAT CGATACATCA TGCAGTGGTT AAACAAAAAC ATTTTTATTC TCAAATGAGA     180

TAAAGTGAAA ATATATATCA TTATATTACA AAGTACAATT ATTTAGGTTT AATCATGGGG     240

AATGGACAGG GGCGAGATTG GAAAATGGCC ATTAAGAGAT GTAGTAATGT TGCTGTAGGA     300

GTAGGGGGA AGAGTAAAAA ATTTGGAGAA GGGAATTTCA GATGGGCCAT TAGAATGGCT      360

AATGTATCTA CAGGACGAGA ACCTGGTGAT ATACCAGAGA CTTTAGATCA ACTAAGGTTG    420

GTTATTTGCG ATTTACAAGA AAGAAGAGAA AAATTTGGAT CTAGCAAAGA AATTGATATG    480

GCAATTGTGA CATTAAAAGT CTTTGCGGTA GCAGGACTTT TGAATATGAC GGTGTCTACT    540

GCTGCTGCAG CTGAAAATAT GTATTCTCAA ATGGGATTAG ACACTAGGCC ATCTATGAAA   600
```

-continued

```
GAAGCAGGTG GAAAAGAGGA AGGCCCTCCA CAGGCATATC CTATTCAAAC AGTAAATGGA      660

GTACCACAAT ATGTAGCACT TGACCCAAAA ATGGTGTCCA TTTTCATGGA AAAGGCAAGA      720

GAAGGACTAG GAGGGGAGGA AGTTCAACTA TGGTTTACTG CCTTCTCTGC AAATTTAACA      780

CCTACTGACA TGGCCACATT AATAATGGCC GCACCAGGGT GCGCTGCAGA TAAAGAAATA      840

TTGGATGAAA GCTTAAAGCA ACTGACAGCA GAATATGATC GCACACATCC CCCTGATGCT      900

CCCAGACCAT TACCCTATTT TACTGCAGCA GAAATTATGG GTATAGGATT AACTCAAGAA      960

CAACAAGCAG AAGCAAGATT TGCACCAGCT AGGATGCAGT GTAGAGCATG GTATCTCGAG     1020

GCATTAGGAA AATTGGCTGC CATAAAAGCT AAGTCTCCTC GAGCTGTGCA GTTAAGACAA     1080

GGAGCTAAGG AAGATTATTC ATCCTTTATA GACAGATTGT TTGCCCAAAT AGATCAAGAA     1140

CAAAATACAG CTGAAGTTAA GTTATATTTA AACAGTCAT TAAGCATAGC TAATGCTAAT     1200

GCAGACTGTA AAAGGCAAT GAGCCACCTT AAGCCAGAAA GTACCCTAGA AGAAAGTTG     1260

AGAGCTTGTC AAGAAATAGG CTCACCAGGA TATAAAATGC AACTCTTGGC AGAAGCTCTT     1320

ACAAAAGTTC AAGTAGTGCA ATCAAAAGGA TCAGGACCAG TGTGTTTTAA TTGTAAAAAA     1380

CCAGGACATC TAGCAAGACA ATGTAGAGAA GTGAAAAAAT GTAATAAATG TGGAAAACCT     1440

GGTCATCTAG CTGCCAAATG TTGGCAAGGA AATAGAAAGA ATTCGGGAAA CTGGAAGGCG     1500

GGGCGAGCTG CAGCCCCAGT GAATCAAATG CAGCAAGCAG TAATGCCATC TGCACCTCCA     1560

ATGGAGGAGA AACTATTGGA TTTATAAATT ATAATAAAGT AGGTACGACT ACAACATTAG     1620

AAAAGAGGCC AGAAATACTT ATATTTGTAA ATGGATATCC TATAAAATTT TTATTAGATA     1680

CAGGAGCAGA TATAACAATT TTAAATAGGA GAGATTTTCA GTAAAAAAT TCTATAGAAA     1740

ATGGAAGGCA AAATATGATT GGAGTAGGAG GAGGAAAGAG AGGAACAAAT TATATTAATG     1800

TACATTTAGA GATTAGAGAT GAAAATTATA AGACACAATG TATATTTGGT AATGTTTGTG     1860

TCTTAGAAGA TAACTCATTA ATACAACCAT TATTGGGGAG AGATAATATG ATTAAATTCA     1920

ATATTAGGTT AGTAATGGCT CAATAATTTT ATCCCGGGTT TTTATAGCTA ATTAGTCATT     1980

TTTCGTAAGT AAGTATTTTT ATTTAATACT TTTTATTGTA CTTATGTTAA AT           2032
```

(2) INFORMATION FOR SEQ ID NO:6:

(i) SEQUENCE CHARACTERISTICS:
        (A) LENGTH: 4727 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
TTAATCAATA AAAGAATTC CTGCAGCCCT GCAGCTAATT AATTAAGCTA CAAATAGTTT       60

CGTTTTCACC TTGTCTAATA ACTAATTAAT TAAGGATCCC CCGTACCGGG CCCCCCCTCG      120

AGGTCGACTT CTTTATTCTA TACTTAAAAA GTGAAAATAA ATACAAAGGT TCTTGAGGGT      180

TGTGTTAAAT TGAAAGCGAG AAATAATCAT AAATTATTTC ATTATCGCGA TATCCGTTAA      240

GTTTGTATCG TAATGGCAGA AGGATTTGCA GCCAATAGAC AATGGATAGG ACCAGAAGAA      300

GCTGAAGAGT TATTAGATTT TGATATAGCA ACACAAATGA GTGAAGAAGG ACCACTAAAT      360

CCAGGAGTAA ACCCATTTAG GGTACCTGGA ATAACAGAAA AAGAAAAGCA AAACTACTGT      420

AACATATTAC AACCTAAGGT TACAAGATCT AAGGAACGAA TTCAAGAGGT AAAACTGGAA      480

GAAGGAAATG CAGGTAAGTT TAGAAGAGCA AGATTTTTAA GGTATTCTGA TGAACAAGTA      540
```

```
TTGTCCCTGG TTCATGCGTT CATAGGATAT TGTATATATT TAGGTAATCG AAATAAGTTA      600

GGATCTTTAA GACATGACAT TGATATAGAA GCACCCCAAG AAGAGTGTTA TAATAATAGA      660

GAGAAGGGTA CAACTGACAA TATAAAATAT GGTAGACGAT GTTGCCTAGG AACGGTGACT      720

TTGTACCTGA TTTTATTTAT AGGATTAATA ATATATTCAC AGACAACCAA CGCTCAGGTA      780

GTATGGAGAC TTCCACCATT AGTAGTCCCA GTAGAAGAAT CAGAAATAAT TTTTTGGGAC      840

TGTTGGGCAC CAGAAGAACC CGCCTGTCAG GACTTTCTTG GGGCAATGAT ACATCTAAAA      900

GCTAAGACAA ATATAAGTAT ACGAGAGGGA CCTACCTTGG GGAATTGGAC TAGAGAAATA      960

TGGGCAACAT TATTCAAAAA GGCTACTAGA CAATGTAGAA GAGGCAGAAT ATGGAAAAGA     1020

TGGAATGAGA CTATAACAGG ACCATCAGGA TGTGCTAATA ACACATGTTA TAATGTTTCA     1080

GTAATAGTAC CTGATTATCA GTGTTATTTA GATAGAGTAG ATACTTGGTT ACAAGGGAAA     1140

ATAAATATAT CATTATGTCT AACAGGAGGA AAAATGTTGT ACAATAAAGT TACAAAACAA     1200

TTAAGCTATT GTACAGACCC ATTACAAATC CCACTGATCA ATTATACATT TGGACCTAAT     1260

CAAACATGTA TGTGGAATAC TTCACAAATT CAGGACCCTG AAATACCAAA ATGTGGATGG     1320

TGGAATCAAA TGGCCTATTA TAACAGTTGT AAATGGGAAG AGGCAAAGGT AAAGTTTCAT     1380

TGTCAAAGAA CACAGAGTCA GCCTGGATCA TGGCGTAGAG CAATCTCGTC ATGGAAACAA     1440

AGAAATAGAT GGGAGTGGAG ACCAGATTTG GAAAGTAAAA AGGTGAAAAT ATCTCTACAG     1500

TGCAATAGCA CAAAAAACCT AACCTTTGCA ATGAGAAGTT CAGGAGATTA TGGAGAAGTA     1560

ACGGGAGCTT GGATAGAGTT TGGATGTCAT AGAAATAAAT CAAACATCA TTCTGAAGCA      1620

AGGTTTAGAA TTAGATGTAG ATGGAATGTA GGATCCGATA CCTCGCTCAT TGATACATGT     1680

GGAAACACTC GAGATGTTTC AGGTGCGAAT CCTGTAGATT GTACCATGTA TTCAAATAAA     1740

ATGTACAATT GTTCTTTACA AAATGGGTTT ACTATGAAGG TAGATGACCT TATTGTGCAT     1800

TTCAATATGA CAAAAGCTGT AGAAATGTAT AATATTGCTG GAAATTGGTC TTGTACATCT     1860

GACTTGCCAT CGTCATGGGG GTATATGAAT TGTAATTGTA CAAATAGTAG TAGTAGTTAT     1920

AGTGGTACTA AAATGGCATG TCCTAGCAAT CGAGGCATCT TAAGGAATTG GTATAACCCA     1980

GTAGCAGGAT TACGACAATC CTTAGAACAG TATCAAGTTG TAAAACAACC AGATTACTTA     2040

GTGGTCCCAG AGGAAGTCAT GGAATATAAA CCTAGAAGGA AAAGGGCAGC TATTCATGTT     2100

ATGTTGGCTC TTGCAACAGT ATTATCTATT GTCGGTGCAG GGACGGGGGC TACTGCTATA     2160

GGGATGGTAA CCCAATACCA CCAAGTTCTG GCAACCCATC AAGAAGCTAT AGAAAAGGTG     2220

ACTGAAGCCT AAAGATAAA CAACTTAAGA TTAGTTACAT TAGAGCATCA AGTACTAGTA      2280

ATAGGATTAA AAGTAGAAGC TATGGAAAAA TTCTTATATA CAGCTTTCGC TATGCAAGAA     2340

TTAGGATGTA ATCAAAATCA ATTCTTCTGC AAAATCCCTC CTGGGTTGTG GACAAGGTAT     2400

AATATGACTA TAAATCAAAC AATATGGAAT CATGGAAATA TAACTTTGGG GAATGGTAT     2460

AACCAAACAA AAGATTTACA ACAAAAGTTT TATGAAATAA TAATGGACAT AGAACAAAAT     2520

AATGTACAAG GGAAAACAGG GATACAACAA TTACAAAAGT GGGAAGATTG GGTAGGATGG     2580

ATGGGAAATA TTCCACAATA TTTAAAGGGA CTATTGGGAG GTATCTTGGG AATAGGATTA     2640

GGAGTGTTAT TATTTGATTTT ATGTTTACCT ACATTGGTTG ATTGTATAAG AAATTGTATC    2700

CACAAGATAC TAGGATACAC AGTAATTGCA ATGCCTGAAG TAGAAGGAGA AGAAATACAA     2760

CCACAAATGG AATTGAGGAG AAATGGTAGG CAATGTGGCA TGTCTGAAAA AGAGGAGGAA     2820

TGAATCGATA CATCATGCAG TGGTTAAACA AAAACATTTT TATTCTCAAA TGAGATAAAG     2880

TGAAAATATA TATCATTATA TTACAAAGTA CAATTATTTA GGTTTAATCA TGGGGAATGG     2940
```

```
ACAGGGGCGA GATTGGAAAA TGGCCATTAA GAGATGTAGT AATGTTGCTG TAGGAGTAGG      3000

GGGGAAGAGT AAAAAATTTG GAGAAGGGAA TTTCAGATGG GCCATTAGAA TGGCTAATGT      3060

ATCTACAGGA CGAGAACCTG GTGATATACC AGAGACTTTA GATCAACTAA GGTTGGTTAT      3120

TTGCGATTTA CAAGAAAGAA GAGAAAAATT TGGATCTAGC AAAGAAATTG ATATGGCAAT      3180

TGTGACATTA AAAGTCTTTG CGGTAGCAGG ACTTTTGAAT ATGACGGTGT CTACTGCTGC      3240

TGCAGCTGAA AATATGTATT CTCAAATGGG ATTAGACACT AGGCCATCTA TGAAAGAAGC      3300

AGGTGGAAAA GAGGAAGGCC CTCCACAGGC ATATCCTATT CAAACAGTAA ATGGAGTACC      3360

ACAATATGTA GCACTTGACC CAAAAATGGT GTCCATTTTC ATGGAAAAGG CAAGAGAAGG      3420

ACTAGGAGGG GAGGAAGTTC AACTATGGTT TACTGCCTTC TCTGCAAATT TAACACCTAC      3480

TGACATGGCC ACATTAATAA TGGCCGCACC AGGGTGCGCT GCAGATAAAG AAATATTGGA      3540

TGAAAGCTTA AAGCAACTGA CAGCAGAATA TGATCGCACA CATCCCCCTG ATGCTCCCAG      3600

ACCATTACCC TATTTTACTG CAGCAGAAAT TATGGGTATA GGATTAACTC AAGAACAACA      3660

AGCAGAAGCA AGATTTGCAC CAGCTAGGAT GCAGTGTAGA GCATGGTATC TCGAGGCATT      3720

AGGAAAATTG GCTGCCATAA AAGCTAAGTC TCCTCGAGCT GTGCAGTTAA GACAAGGAGC      3780

TAAGGAAGAT TATTCATCCT TTATAGACAG ATTGTTTGCC CAAATAGATC AAGAACAAAA      3840

TACAGCTGAA GTTAAGTTAT ATTTAAAACA GTCATTAAGC ATAGCTAATG CTAATGCAGA      3900

CTGTAAAAAG GCAATGAGCC ACCTTAAGCC AGAAAGTACC CTAGAAGAAA AGTTGAGAGC      3960

TTGTCAAGAA ATAGGCTCAC CAGGATATAA AATGCAACTC TTGGCAGAAG CTCTTACAAA      4020

AGTTCAAGTA GTGCAATCAA AAGGATCAGG ACCAGTGTGT TTTAATTGTA AAAAACCAGG      4080

ACATCTAGCA AGACAATGTA GAGAAGTGAA AAAATGTAAT AAATGTGGAA AACCTGGTCA      4140

TCTAGCTGCC AAATGTTGGC AAGGAAATAG AAAGAATTCG GGAAACTGGA AGGCGGGGCG      4200

AGCTGCAGCC CCAGTGAATC AAATGCAGCA AGCAGTAATG CCATCTGCAC CTCCAATGGA      4260

GGAGAAACTA TTGGATTTAT AAATTATAAT AAAGTAGGTA CGACTACAAC ATTAGAAAAG      4320

AGGCCAGAAA TACTTATATT TGTAAATGGA TATCCTATAA AATTTTTATT AGATACAGGA      4380

GCAGATATAA CAATTTTAAA TAGGAGAGAT TTTCAAGTAA AAAATTCTAT AGAAAATGGA      4440

AGGCAAAATA TGATTGGAGT AGGAGGAGGA AAGAGAGGAA CAAATTATAT TAATGTACAT      4500

TTAGAGATTA GAGATGAAAA TTATAAGACA CAATGTATAT TTGGTAATGT TTGTGTCTTA      4560

GAAGATAACT CATTAATACA ACCATTATTG GGGAGAGATA ATATGATTAA ATTCAATATT      4620

AGGTTAGTAA TGGCTCAATA ATTTTATCCC GGGTTTTTAT AGCTAATTAG TCATTTTTCG      4680

TAAGTAAGTA TTTTTATTTA ATACTTTTTA TTGTACTTAT GTTAAAT                   4727

(2) INFORMATION FOR SEQ ID NO:7:

(i) SEQUENCE CHARACTERISTICS:
        (A) LENGTH: 4150 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TTAATCAATA AAAAGAATTC CTGCAGGAAT TCATAAAAAT CATTCTTCTC CTTCTACTTC        60

AGGCATTGCA ATTACTGTGT ATCCTAGTAT CTTGTGGATA CAATTTCTTA TACAATCAAC       120

CAATGTAGGT AAACATAAAA TCAATAATAA CACTCCTAAT CCTATTCCCA AGATACCTCC       180
```

```
CAATAGTCCC CTTTTCCTTC TAGGTTTATA TTCCATGACT TCCTCTGGGA CCACTAAGTA    240

ATCTGGTTGT TTTACAACTT GATACTGTTC TAAGGATTGT CGTAATCCTG CTACTGGGTT    300

ATACCAATTC CTTAAGATGC CTCGATTGCT AGGACATGCC ATTTTAGTAC CACTATAACT    360

ACTACTACTA TTTGTACAAT TACAATTCAT ATACCCCCAT GACGATGGCA AGTCAGATGT    420

ACAAGACCAA TTTCCAGCAA TATTATACAT TTCTACAGCT TTTGTCATAT TGAAATGCAC    480

AATAAGGTCA TCTACCTTCA TAGTAAACCC ATTTTGTAAA GAACAATTGT ACATTTTATT    540

TGAATACATG GTACAATCTA CAGGATTCGC ACCTGAAACA TCTCGAGTGT TTCCACATGT    600

ATCAATGAGC GAGGTATCGG ATCCTACATT CCATCTACAT CTAATTCTAA ACCTTGCTTC    660

AGAATGATGT TTTGATTTAT TTCTATGACA TCCAAACTCT ATCCAAGCTC CCGTTACTTC    720

TCCATAATCT CCTGAACTTC TCATTGCAAA GGTTAGGTTT TTTGTGCTAT TGCACTGTAG    780

AGATATTTTC ACCTTTTTAC TTTCCAAATC TGGTCTCCAC TCCCATCTAT TTCTTTGTTT    840

CCATGACGAG ATTGCTCTAC GCCATGATCC AGGCTGACTC TGTGTTCTTT GACAATGAAA    900

CTTTACCTTT GCCTCTTCCC ATTTACAACT GTTATAATAG GCCATTTGAT TCCACCATCC    960

ACATTTGGT ATTTCAGGGT CCTGAATTTG TGAAGTATTC CACATACATG TTTGATTAGG   1020

TCCAAATGTA TAATTGATCA GTGGGATTTG TAATGGGTCT GTACAATAGC TTAATTGTTT   1080

TGTAACTTTA TTGTACAACA TTTTTCCTCC TGTTAGACAT AATGATATAT TTATTTTCCC   1140

TTGTAACCAA GTATCTACTC TATCTAAATA ACACTGATAA TCAGGTACTA TTACTGAAAC   1200

ATTATAACAT GTGTTATTAG CACATCCTGA TGGTCCTGTT ATAGTCTCAT TCCATCTTTT   1260

CCATATTCTG CCTCTTCTAC ATTGTCTAGT AGCCTTTTTG AATAATGTTG CCCATATTTC   1320

TCTAGTCCAA TTCCCCAAGG TAGGTCCCTC TCGTATACTT ATATTTGTCT TAGCTTTTAG   1380

ATGTATCATT GCCCCAAGAA AGTCCTGACA GGCGGGTTCT TCTGGTGCCC AACAGTCCCA   1440

AAAAATTATT TCTGATTCTT CTACTGGGAC TACTAATGGT GGAAGTCTCC ATACTACCTG   1500

AGCGTTGGTT GTCTGTGAAT ATATTATTAA TCCTATAAAT AAAATCAGGT ACAAAGTCAC   1560

CGTTCCTAGG CAACATCGTC TACCATATTT TATATTGTCA GTTGTACCCT TCTCTCTATT   1620

ATTATAACAC TCTTCTTGGG GTGCTTCTAT ATCAATGTCA TGTCTTAAAG ATCCTAACTT   1680

ATTTCGATTA CCTAAATATA TACAATATCC TATGAACGCA TGAACCAGGG ACAATACTTG   1740

TTCATCAGAA TACCTTAAAA ATCTTGCTCT TCTAAACTTA CCTGCATTTC CTTCTTCCAG   1800

TTTTACCTCT TGAATTTCGT TCCTTAGATC TTGTAACTTA GGTTGTAATA TGTTACAGTA   1860

GTTTTGCTTT TCTTTTTCTG TTATTCCAGG TACCCTAAAT GGGTTTACTC CTGGATTTAG   1920

TGGTCCTTCT TCACTCATTT GTGTTGCTAT ATCAAAATCT AATAACTCTT CAGCTTCTTC   1980

TGGTCCTATC CATTGTCTAT TGGCTGCAAA TCCTTCTGCC ATTACGATAC AAACTTAACG   2040

GATATCGCGA TAATGAAATA ATTTATGATT ATTTCTCGCT TTCAATTTAA CACAACCCTC   2100

AAGAACCTTT GTATTTATTT TCACTTTTTA AGTATAGAAT AAAGAACTGC AGCTAATTAA   2160

TTAAGCTACA AATAGTTTCG TTTTCACCTT GTCTAATAAC TAATTAATTA AGGATCCCCC   2220

GTACCGGGCC CCCCCTCGAG GTCGACATCG ATACATCATG CAGTGGTTAA ACAAAAACAT   2280

TTTTATTCTC AAATGAGATA AAGTGAAAAT ATATATCATT ATATTACAAA GTACAATTAT   2340

TTAGGTTTAA TCATGGGGAA TGGACAGGGG CGAGATTGGA AAATGGCCAT TAAGAGATGT   2400

AGTAATGTTG CTGTAGGAGT AGGGGGGAAG AGTAAAAAAT TTGGAGAAGG GAATTTCAGA   2460

TGGGCCATTA GAATGGCTAA TGTATCTACA GGACGAGAAC CTGGTGATAT ACCAGAGACT   2520
```

```
TTAGATCAAC TAAGGTTGGT TATTTGCGAT TTACAAGAAA GAAGAGAAAA ATTTGGATCT        2580

AGCAAAGAAA TTGATATGGC AATTGTGACA TTAAAAGTCT TTGCGGTAGC AGGACTTTTG        2640

AATATGACGG TGTCTACTGC TGCTGCAGCT GAAAATATGT ATTCTCAAAT GGGATTAGAC        2700

ACTAGGCCAT CTATGAAAGA AGCAGGTGGA AAAGAGGAAG CCCTCCACA GGCATATCCT         2760

ATTCAAACAG TAAATGGAGT ACCACAATAT GTAGCACTTG ACCCAAAAAT GGTGTCCATT        2820

TTCATGGAAA AGGCAAGAGA AGGACTAGGA GGGGAGGAAG TTCAACTATG GTTTACTGCC        2880

TTCTCTGCAA ATTTAACACC TACTGACATG GCCACATTAA TAATGGCCGC ACCAGGGTGC        2940

GCTGCAGATA AAGAAATATT GGATGAAAGC TTAAAGCAAC TGACAGCAGA ATATGATCGC        3000

ACACATCCCC CTGATGCTCC CAGACCATTA CCCTATTTTA CTGCAGCAGA AATTATGGGT        3060

ATAGGATTAA CTCAAGAACA ACAAGCAGAA GCAAGATTTG CACCAGCTAG GATGCAGTGT        3120

AGAGCATGGT ATCTCGAGGC ATTAGGAAAA TTGGCTGCCA TAAAAGCTAA GTCTCCTCGA        3180

GCTGTGCAGT TAAGACAAGG AGCTAAGGAA GATTATTCAT CCTTTATAGA CAGATTGTTT        3240

GCCCAAATAG ATCAAGAACA AAATACAGCT GAAGTTAAGT TATATTTAAA ACAGTCATTA        3300

AGCATAGCTA ATGCTAATGC AGACTGTAAA AAGGCAATGA GCCACCTTAA GCCAGAAAGT        3360

ACCCTAGAAG AAAAGTTGAG AGCTTGTCAA GAAATAGGCT CACCAGGATA TAAAATGCAA        3420

CTCTTGGCAG AAGCTCTTAC AAAAGTTCAA GTAGTGCAAT CAAAAGGATC AGGACCAGTG        3480

TGTTTTAATT GTAAAAAACC AGGACATCTA GCAAGACAAT GTAGAGAAGT GAAAAAATGT        3540

AATAAATGTG GAAAACCTGG TCATCTAGCT GCCAAATGTT GGCAAGGAAA TAGAAAGAAT        3600

TCGGGAAACT GGAAGGCGGG GCGAGCTGCA GCCCCAGTGA ATCAAATGCA GCAAGCAGTA        3660

ATGCCATCTG CACCTCCAAT GGAGGAGAAA CTATTGGATT TATAAATTAT AATAAAGTAG        3720

GTACGACTAC AACATTAGAA AAGAGGCCAG AAATACTTAT ATTTGTAAAT GGATATCCTA        3780

TAAAATTTTT ATTAGATACA GGAGCAGATA TAACAATTTT AAATAGGAGA GATTTTCAAG        3840

TAAAAAATTC TATAGAAAAT GGAAGGCAAA ATATGATTGG AGTAGGAGGA GGAAAGAGAG        3900

GAACAAATTA TATTAATGTA CATTTAGAGA TTAGAGATGA AAATTATAAG ACACAATGTA        3960

TATTTGGTAA TGTTTGTGTC TTAGAAGATA ACTCATTAAT ACAACCATTA TTGGGGAGAG        4020

ATAATATGAT TAAATTCAAT ATTAGGTTAG TAATGGCTCA ATAATTTTAT CCCGGGTTTT        4080

TATAGCTAAT TAGTCATTTT TCGTAAGTAA GTATTTTTAT TTAATACTTT TTATTGTACT        4140

TATGTTAAAT                                                              4150

(2) INFORMATION FOR SEQ ID NO:8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

ATCATCAAGC TTCTGCAGTT CTTTATTCTA TACTTA                                  36

(2) INFORMATION FOR SEQ ID NO:9:

(i) SEQUENCE CHARACTERISTICS:
        (A) LENGTH: 79 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO:9:

AAATTCTTAT ATACAGCTTT CGCTATGCAA GAATTAGGAT GTAATCAAAA TCAATTCTTC        60

TGCAAAATCC CTCCTGGGT        79

(2) INFORMATION FOR SEQ ID NO:10:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:10:

CCCATCGAGT GCGGCTAC        18

(2) INFORMATION FOR SEQ ID NO:11:

(i) SEQUENCE CHARACTERISTICS:
            (A) LENGTH: 75 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:11:

GCAGAAGAAT TGATTTTGAT TACATCCTAA TTCTTGCATA GCGAAAGCTG TATATAAGAA        60

TTTTTCCATA GCTTC        75

(2) INFORMATION FOR SEQ ID NO:12:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:12:

AAGTTCTGGC AACCCATC        18

(2) INFORMATION FOR SEQ ID NO:13:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:13:

ATCATCCTGC AGAAGCTTCC CGGGTTCTTT ATTCTATACT T        41

(2) INFORMATION FOR SEQ ID NO:14:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:14:

CTGCAAATCC TTCTGCCATT ACGATACAAA CTTAAC                                36

(2) INFORMATION FOR SEQ ID NO:15:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

CGTTAAGTTT GTATCGTAAT GGCAGAAGGA TTTGCAGCC                             39

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

CCTCTTGAAT TTCGTTCC                                                    18

(2) INFORMATION FOR SEQ ID NO:17:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

ATCATCGAGC TCGCGGCCGC CTATCAAAAG TCTTAATGAG TT                         42

(2) INFORMATION FOR SEQ ID NO:18:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

GAATTCCTCG AGCTGCAGCC CGGGTTTTTA TAGCTAATTA GTCATTTTTT CGTAAGTAAG      60

TATTTTTATT TAA                                                        73

(2) INFORMATION FOR SEQ ID NO:19:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

CCCGGGCTGC AGCTCGAGGA ATTCTTTTTA TTGATTAACT AGTCAAATGA GTATATATAA        60

TTGAAAAAGT AA        72

(2) INFORMATION FOR SEQ ID NO:20:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GATGATGGTA CCTTCATAAA TACAAGTTTG ATTAAACTTA AGTTG        45

(2) INFORMATION FOR SEQ ID NO:21:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

GGGGGATCCT TAATTAATTA GTTATTAGAC AAGGTGAAAA CGAAACTATT TGTAGCTTAA        60

TTAATTAGCT GCAGGAATTC        80

(2) INFORMATION FOR SEQ ID NO:22:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

CAAAAATGGT GTCCATTTTC ATGGAAAAGG CAAGAGAAGG AC        42

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

CTGCTGCAGT AAAATAGG        18

(2) INFORMATION FOR SEQ ID NO:24:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

CTTCTCTTGC CTTTTCCATG AAAATGGACA CCATTTTTGG GTC    43

(2) INFORMATION FOR SEQ ID NO:25:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

CAATTATTTA GGTTTAATCA TGGGGAATGG ACAGGGGC    38

(2) INFORMATION FOR SEQ ID NO:26:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

CGCCCCTGTC CATTCCCCAT GATTAAACCT AAATAATTGT AC    42

(2) INFORMATION FOR SEQ ID NO:27:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

ATCATCGTCG ACATCGATAC ATCATGCAGT GGTTAAAC    38

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

CAGGACATCT AGCAAGAC    18

(2) INFORMATION FOR SEQ ID NO:29:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

GATGATCCCG GGATAAAAAT TATTGAGCCA TTACTAACCT    40

(2) INFORMATION FOR SEQ ID NO:30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

TATGAATTGT AATTGTAC                                                                       18

(2) INFORMATION FOR SEQ ID NO:31:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

GTAGCATAAG GTTACCGCGG CCGCTAAGCT TAGGTTACCA TCCCTATAGC AGTA       54

(2) INFORMATION FOR SEQ ID NO:32:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

GTAGCATAAG GTAACCTAAG CTTAGCGGCC GCGGTAACCC AATACCACCA AGTTCTGGC     59

(2) INFORMATION FOR SEQ ID NO:33:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

ATTAACCCTC ACTAAAG                                                                       17

(2) INFORMATION FOR SEQ ID NO:34:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

ACTTGCCATC GTCATGGGGG                                                       20

(2) INFORMATION FOR SEQ ID NO:35:

```
    (i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

GATACCTCCC AATAGTCCCC TTTTCCTTCT AGGTTTATAT TC                42

(2) INFORMATION FOR SEQ ID NO:36:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

GAATATAAAC CTAGAAGGAA AAGGGGACTA TTGGGAGGTA TC                42

(2) INFORMATION FOR SEQ ID NO:37:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

ATCATCGAAT TCATAAAAAT CATTCTTCTC CTTCTACTTC                   40
```